(12) United States Patent
McDevitt et al.

(10) Patent No.: US 8,257,967 B2
(45) Date of Patent: Sep. 4, 2012

(54) METHOD AND SYSTEM FOR THE DETECTION OF CARDIAC RISK FACTORS

(75) Inventors: John T. McDevitt, Austin, TX (US); Eric V. Anslyn, Austin, TX (US); Jason B. Shear, Austin, TX (US); Dean P. Neikirk, Austin, TX (US); Nick J. Christodoulides, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 851 days.

(21) Appl. No.: 10/427,744

(22) Filed: Apr. 28, 2003

(65) Prior Publication Data

US 2004/0029259 A1   Feb. 12, 2004

Related U.S. Application Data

(60) Provisional application No. 60/375,775, filed on Apr. 26, 2002.

(51) Int. Cl.
*C12M 1/34* (2006.01)
(52) U.S. Cl. .............. 435/288.7; 435/287.1; 435/287.2; 436/518; 436/164
(58) Field of Classification Search .................. 422/68.1, 422/81–82.09; 435/286–287.1, 288.4–288.7; 436/518, 524, 531
See application file for complete search history.

(56) References Cited

U.S. PATENT DOCUMENTS

| | | | |
|---|---|---|---|
| 3,696,932 A | 10/1972 | Rosenberg | |
| 3,701,433 A | 10/1972 | Krakauer et al. | |
| 3,709,868 A | 1/1973 | Spector | |
| 3,843,696 A | 10/1974 | Wagner et al. | |
| 3,856,469 A | 12/1974 | Schneider et al. | |
| 3,876,504 A | 4/1975 | Koffler | |
| 3,954,623 A | 5/1976 | Hammer et al. | |
| 3,964,974 A | 6/1976 | Banauch et al. | |

(Continued)

FOREIGN PATENT DOCUMENTS

DE   19736641   3/1999

(Continued)

OTHER PUBLICATIONS

Dickinson et al., "Convergent, Self-Encoded Bead Sensor Arrays in the Design of an Artificial Nose", Anal. Chem., Jun. 1, 1999, vol. 71, No. 11, pp. 2192-2198.

(Continued)

*Primary Examiner* — N. C. Yang
(74) *Attorney, Agent, or Firm* — Plumsea Law Group, LLC

(57) ABSTRACT

A system for the rapid characterization of multi-cardiovascular risk factor analyte fluids, in one embodiment, includes a light source, a sensor array, and a detector. The sensor array is formed from a supporting member, in which a plurality of cavities may be formed. A series of chemically sensitive particles, in one embodiment, are positioned within the cavities. The particles may produce a signal when a receptor, coupled to the particle, interacts with the cardiovascular risk factor analyte and the particle-analyte complex is visualized using a visualization reagent. Using pattern recognition techniques, the analytes within a multi-analyte fluid may be characterized. In an embodiment, each cavity of the plurality of cavities is designed to capture and contain a specific size particle. Flexible projections may be positioned over each of the cavities to provide retention of the particles in the cavities.

30 Claims, 43 Drawing Sheets

U.S. PATENT DOCUMENTS

| | | | |
|---|---|---|---|
| 4,036,946 A | 7/1977 | Kleinerman | |
| 4,050,898 A | 9/1977 | Goffe et al. | |
| 4,069,017 A | 1/1978 | Wu et al. | |
| 4,115,277 A | 9/1978 | Swank | |
| 4,189,382 A | 2/1980 | Zine, Jr. | |
| 4,200,613 A | 4/1980 | Alfrey et al. | |
| 4,245,041 A | 1/1981 | Denney | |
| 4,246,107 A | 1/1981 | Takenaka et al. | |
| 4,294,817 A | 10/1981 | Burgett et al. | |
| 4,344,743 A | 8/1982 | Bessman et al. | |
| 4,360,611 A | 11/1982 | Wakimoto et al. | |
| 4,378,429 A | 3/1983 | Modrovich | |
| 4,477,575 A | 10/1984 | Vogel et al. | |
| 4,493,815 A * | 1/1985 | Fernwood et al. ............ 422/101 | |
| 4,567,149 A | 1/1986 | Sell et al. | |
| 4,596,657 A | 6/1986 | Wisdom | |
| 4,623,461 A | 11/1986 | Hossom et al. | |
| 4,661,445 A | 4/1987 | Saxinger et al. | |
| 4,672,028 A | 6/1987 | Olson | |
| 4,681,742 A | 7/1987 | Johnson et al. | |
| 4,683,195 A | 7/1987 | Mullis et al. | |
| 4,683,202 A | 7/1987 | Mullis | |
| 4,734,372 A | 3/1988 | Rotman | |
| 4,753,776 A | 6/1988 | Hillman et al. | |
| 4,795,698 A | 1/1989 | Owen et al. | |
| 4,810,378 A | 3/1989 | Carmen et al. | |
| 4,813,277 A | 3/1989 | Miller et al. | |
| 4,828,386 A | 5/1989 | Matkovich et al. | |
| 4,855,225 A | 8/1989 | Fung et al. | |
| 4,874,499 A | 10/1989 | Smith et al. | |
| 4,908,112 A | 3/1990 | Pace | |
| 4,925,800 A | 5/1990 | Kovacs et al. | |
| 4,938,742 A | 7/1990 | Smits | |
| 4,965,188 A | 10/1990 | Mullis et al. | |
| 4,988,618 A | 1/1991 | Li et al. | |
| 4,997,577 A | 3/1991 | Stewart | |
| 5,053,197 A | 10/1991 | Bowen | |
| 5,071,076 A | 12/1991 | Chagnon et al. | |
| 5,096,807 A | 3/1992 | Leaback | |
| 5,108,933 A | 4/1992 | Liberti et al. | |
| 5,126,276 A | 6/1992 | Fish et al. | |
| 5,130,238 A | 7/1992 | Malek et al. | |
| 5,137,031 A | 8/1992 | Guirgui | |
| 5,137,833 A | 8/1992 | Russell | |
| 5,143,853 A | 9/1992 | Walt | |
| 5,147,606 A | 9/1992 | Charlton et al. | |
| 5,156,810 A | 10/1992 | Ribi | |
| 5,156,972 A | 10/1992 | Issachar | |
| 5,162,863 A | 11/1992 | Ito | |
| 5,168,044 A | 12/1992 | Joyce et al. | |
| 5,182,366 A | 1/1993 | Huebner et al. | |
| 5,188,934 A | 2/1993 | Menchen et al. | |
| 5,209,904 A | 5/1993 | Forney et al. | |
| 5,211,850 A | 5/1993 | Shettigar et al. | |
| 5,219,763 A | 6/1993 | Van Hoegaerden | |
| 5,223,393 A | 6/1993 | Khanna et al. | |
| 5,235,028 A | 8/1993 | Barany et al. | |
| 5,240,640 A | 8/1993 | Siiman et al. | |
| 5,244,636 A | 9/1993 | Walt et al. | |
| 5,244,813 A | 9/1993 | Walt et al. | |
| 5,248,742 A | 9/1993 | McGarry et al. | |
| 5,250,264 A | 10/1993 | Walt et al. | |
| 5,252,294 A | 10/1993 | Kroy et al. | |
| 5,252,494 A | 10/1993 | Walt | |
| 5,262,127 A | 11/1993 | Wise | |
| 5,278,303 A | 1/1994 | Krepinsky et al. | |
| 5,288,214 A | 2/1994 | Fukuda et al. | |
| 5,307,144 A | 4/1994 | Hiroshi et al. | |
| 5,366,860 A | 11/1994 | Bergot et al. | |
| 5,374,530 A | 12/1994 | Nuzzolo et al. | |
| 5,382,512 A | 1/1995 | Smethers et al. | |
| 5,385,709 A | 1/1995 | Wise et al. | |
| 5,391,272 A | 2/1995 | ODaly et al. | |
| 5,405,784 A | 4/1995 | Van Hoegaerden | |
| 5,480,723 A | 1/1996 | Klainer et al. | |
| 5,491,097 A | 2/1996 | Ribi et al. | |
| 5,499,909 A | 3/1996 | Yamada et al. | |
| 5,503,985 A | 4/1996 | Cathey et al. | |
| 5,512,490 A | 4/1996 | Walt et al. | |
| 5,518,887 A | 5/1996 | Parsons et al. | |
| 5,541,057 A | 7/1996 | Bogart et al. | |
| 5,547,682 A | 8/1996 | Chagnon et al. | |
| 5,550,373 A | 8/1996 | Cole et al. | |
| 5,563,042 A | 10/1996 | Phillips et al. | |
| 5,567,627 A | 10/1996 | Lehnen | |
| 5,583,054 A | 12/1996 | Ito et al. | |
| 5,587,128 A | 12/1996 | Wilding et al. | |
| 5,597,531 A | 1/1997 | Liberti et al. | |
| 5,611,676 A | 3/1997 | Ooumi et al. | |
| 5,616,698 A | 4/1997 | Krepinsky et al. | |
| 5,616,790 A | 4/1997 | Arnold et al. | |
| 5,631,130 A | 5/1997 | Leckie et al. | |
| 5,632,876 A | 5/1997 | Zanzucchi et al. | |
| 5,637,469 A | 6/1997 | Wilding et al. | |
| 5,653,939 A | 8/1997 | Hollis et al. | |
| 5,654,497 A | 8/1997 | Hoffheins et al. | |
| 5,677,195 A | 10/1997 | Winkler et al. | |
| 5,677,196 A | 10/1997 | Herron et al. | |
| 5,681,484 A | 10/1997 | Zanzucchi et al. | |
| 5,690,807 A | 11/1997 | Clark, Jr. et al. | |
| 5,698,089 A | 12/1997 | Lewis et al. | |
| 5,698,271 A | 12/1997 | Liberti et al. | |
| 5,700,897 A | 12/1997 | Klainer et al. | |
| 5,705,018 A | 1/1998 | Hartley | |
| 5,707,502 A | 1/1998 | McCaffrey et al. | |
| 5,714,122 A | 2/1998 | Bretscher et al. | |
| 5,747,349 A | 5/1998 | Van Den Engh et al. | |
| 5,748,091 A | 5/1998 | Kim | |
| 5,755,942 A | 5/1998 | Zanzucchi et al. | |
| 5,756,291 A | 5/1998 | Griffin et al. | |
| 5,759,015 A | 6/1998 | Van Lintel et al. | |
| 5,770,370 A | 6/1998 | Kumar | |
| 5,770,416 A | 6/1998 | Lihme et al. | |
| 5,773,307 A | 6/1998 | Colin et al. | |
| 5,779,907 A | 7/1998 | Yu | |
| 5,788,814 A | 8/1998 | Sun et al. | |
| 5,797,898 A | 8/1998 | Santini, Jr. et al. | |
| 5,814,524 A | 9/1998 | Walt et al. | |
| 5,827,748 A | 10/1998 | Golden | |
| 5,834,318 A | 11/1998 | Buettner | |
| 5,837,552 A | 11/1998 | Cotton et al. | |
| 5,840,256 A | 11/1998 | Demers et al. | |
| 5,843,655 A | 12/1998 | McGall | |
| 5,843,767 A | 12/1998 | Beattie | |
| 5,846,396 A | 12/1998 | Zanzucchi et al. | |
| 5,846,708 A | 12/1998 | Hollis et al. | |
| 5,854,141 A | 12/1998 | Cronin et al. | |
| 5,854,684 A | 12/1998 | Stabile et al. | |
| 5,856,174 A | 1/1999 | Lipshutz et al. | |
| 5,858,804 A | 1/1999 | Zanzucchi et al. | |
| 5,863,957 A | 1/1999 | Li et al. | |
| 5,866,099 A | 2/1999 | Owen et al. | |
| 5,866,430 A | 2/1999 | Grow | |
| 5,869,241 A | 2/1999 | Edwards et al. | |
| 5,872,170 A | 2/1999 | Mine et al. | |
| 5,872,623 A | 2/1999 | Stabile et al. | |
| 5,876,605 A | 3/1999 | Kitajima et al. | |
| 5,891,656 A | 4/1999 | Zarling et al. | |
| 5,914,042 A | 6/1999 | Ball et al. | |
| 5,922,617 A * | 7/1999 | Wang et al. ................... 436/518 | |
| 5,942,443 A | 8/1999 | Parce et al. | |
| 5,945,334 A | 8/1999 | Besemer et al. | |
| 5,965,590 A | 10/1999 | Rossignol | |
| 5,965,695 A | 10/1999 | Simon et al. | |
| 5,980,704 A | 11/1999 | Cherukuri et al. | |
| 5,981,297 A | 11/1999 | Baselt | |
| 5,985,120 A | 11/1999 | Cholli et al. | |
| 5,992,820 A | 11/1999 | Fare et al. | |
| 6,008,031 A | 12/1999 | Modrich et al. | |
| 6,013,440 A | 1/2000 | Lipshutz et al. | |
| 6,023,540 A | 2/2000 | Walt et al. | |
| 6,037,137 A | 3/2000 | Komoriya et al. | |
| 6,048,732 A | 4/2000 | Anslyn et al. | |
| 6,063,581 A | 5/2000 | Sundrehagen | |
| 6,074,616 A | 6/2000 | Buechler et al. | |
| 6,083,761 A | 7/2000 | Kedar et al. | |
| 6,083,763 A | 7/2000 | Balch | |

| | | |
|---|---|---|
| 6,103,479 A | 8/2000 | Taylor |
| 6,127,139 A | 10/2000 | Te Koppele et al. |
| 6,133,047 A | 10/2000 | Elaissari et al. |
| 6,151,973 A | 11/2000 | Geysen et al. |
| 6,168,948 B1 | 1/2001 | Anderson et al. |
| 6,171,489 B1 | 1/2001 | Ballard et al. |
| 6,171,780 B1 | 1/2001 | Pham et al. |
| 6,210,910 B1 | 4/2001 | Walt et al. |
| 6,232,066 B1 | 5/2001 | Felder et al. |
| 6,243,486 B1 | 6/2001 | Weiss |
| 6,245,296 B1 | 6/2001 | Ligler et al. |
| 6,248,597 B1 * | 6/2001 | Eda et al. ............... 436/518 |
| 6,254,830 B1 | 7/2001 | Pivarnik et al. |
| 6,258,229 B1 | 7/2001 | Winarta et al. |
| 6,268,222 B1 | 7/2001 | Chandler et al. |
| 6,288,220 B1 | 9/2001 | Kambara et al. |
| 6,309,889 B1 | 10/2001 | Cutler et al. |
| 6,331,441 B1 | 12/2001 | Balch et al. |
| 6,355,431 B1 | 3/2002 | Chee et al. |
| 6,355,491 B1 | 3/2002 | Zhou et al. |
| 6,406,920 B1 | 6/2002 | Davis et al. |
| 6,413,786 B1 | 7/2002 | Hansen et al. |
| 6,482,593 B2 | 11/2002 | Walt et al. |
| 6,485,690 B1 * | 11/2002 | Pfost et al. ............... 422/102 |
| 6,488,872 B1 | 12/2002 | Beebe et al. |
| 6,488,897 B2 | 12/2002 | Dunbrow et al. |
| 6,514,415 B2 | 2/2003 | Hatch |
| 6,529,271 B1 | 3/2003 | Engelhardt |
| 6,577,777 B1 | 6/2003 | Yoshino et al. |
| 6,589,779 B1 | 7/2003 | McDevitt et al. |
| 6,591,124 B2 | 7/2003 | Sherman |
| 6,602,702 B1 | 8/2003 | McDevitt et al. |
| 6,618,140 B2 | 9/2003 | Frost et al. |
| 6,630,307 B2 | 10/2003 | Bruchez et al. |
| 6,632,613 B1 | 10/2003 | Wei et al. |
| 6,638,621 B2 | 10/2003 | Anderson |
| 6,649,403 B1 | 11/2003 | McDevitt et al. |
| 6,654,505 B2 | 11/2003 | Bridgham et al. |
| 6,665,439 B1 | 12/2003 | Takahashi |
| 6,667,177 B1 | 12/2003 | Yabusaki |
| 6,680,206 B1 | 1/2004 | McDevitt et al. |
| 6,682,649 B1 | 1/2004 | Peterson et al. |
| 6,686,170 B1 | 2/2004 | Flanders et al. |
| 6,692,696 B1 | 2/2004 | Alberte |
| 6,713,298 B2 | 3/2004 | McDevitt et al. |
| 6,716,629 B2 | 4/2004 | Hess et al. |
| 6,727,058 B2 | 4/2004 | Bushman et al. |
| 6,743,640 B2 | 6/2004 | Whitten et al. |
| 6,773,928 B1 | 8/2004 | Yin et al. |
| 6,828,158 B2 | 12/2004 | Eda et al. |
| 6,846,629 B2 | 1/2005 | Sigal et al. |
| 6,855,490 B2 | 2/2005 | Sompuram et al. |
| 6,869,570 B2 | 3/2005 | Wardlaw |
| 6,890,742 B2 | 5/2005 | Ammann et al. |
| 6,908,770 B1 | 6/2005 | McDevitt et al. |
| 7,022,517 B1 * | 4/2006 | McDevitt et al. ......... 435/288.5 |
| 2001/0002984 A1 | 6/2001 | Vetter |
| 2002/0115088 A1 * | 8/2002 | Kurn ............... 435/6 |
| 2002/0160363 A1 | 10/2002 | McDevitt et al. |
| 2002/0182600 A1 * | 12/2002 | Smith ............... 435/6 |
| 2002/0197622 A1 | 12/2002 | McDevitt et al. |
| 2003/0064422 A1 | 4/2003 | McDevitt et al. |
| 2003/0100603 A1 * | 5/2003 | Beinlich et al. ............ 514/458 |
| 2003/0186228 A1 | 10/2003 | McDevitt et al. |
| 2004/0006218 A1 * | 1/2004 | Griffais et al. ............ 536/23.1 |
| 2004/0029259 A1 | 2/2004 | McDevitt et al. |
| 2004/0053322 A1 | 3/2004 | McDevitt et al. |
| 2005/0136548 A1 | 6/2005 | McDevitt et al. |
| 2005/0164320 A1 | 7/2005 | McDevitt et al. |
| 2005/0191620 A1 | 9/2005 | McDevitt et al. |
| 2005/0214863 A1 | 9/2005 | McDevitt et al. |
| 2006/0257854 A1 * | 11/2006 | McDevitt et al. ............ 435/5 |
| 2006/0257993 A1 * | 11/2006 | McDevitt et al. ......... 435/287.2 |

FOREIGN PATENT DOCUMENTS

| | | |
|---|---|---|
| EP | 0 246 760 | 11/1987 |
| EP | 339 623 | 11/1989 |
| EP | 0 518 557 A2 | 12/1992 |
| EP | 439182 | 4/1996 |
| GB | 2 300 258 | 10/1996 |
| GB | 2 315 131 A | 1/1998 |
| JP | 10-332593 | 12/1998 |
| WO | 90/01069 | 2/1990 |
| WO | 92/00880 | 1/1992 |
| WO | 94/19690 | 9/1994 |
| WO | 98/17383 A1 | 4/1998 |
| WO | 98/25701 | 6/1998 |
| WO | 98/40726 | 9/1998 |
| WO | 98/53300 | 11/1998 |
| WO | 99/17139 | 4/1999 |
| WO | 99/18434 | 4/1999 |
| WO | 99/67024 | 12/1999 |
| WO | 00/04372 | 1/2000 |
| WO | 00/4372 | 1/2000 |
| WO | 00/20117 | 4/2000 |
| WO | 01/06239 | 1/2001 |
| WO | 01/11338 | 2/2001 |
| WO | 01/28681 | 4/2001 |
| WO | 01/55701 | 8/2001 |
| WO | 01/55703 | 8/2001 |

OTHER PUBLICATIONS

Written Opinion, Application No. PCT/US99/16162, mailed May 2, 2000.
International Preliminary Examination Report, Application No. PCT/US99/16162, mailed Oct. 12, 2000.
International Preliminary Examination Report, Application No. PCT/US00/19302, mailed Oct. 12, 2001.
International Preliminary Examination Report, Application No. PCT/US00/19351, mailed Aug. 14, 2001.
International Preliminary Examination Report, Application No. PCT/US00/19350, mailed Aug. 14, 2001.
Examiner's Report, Australian Application No. 53165/99, mailed May 2, 2002.
Examiner's Report, Australian Application No. 53165/99, mailed May 5, 2003.
International Search Report Application No. PCT/US01/03316, mailed May 7, 2001.
Written Opinion, Application No. PCT/US01/03240, mailed Jan. 22, 2002.
International Preliminary Examination Report Application No. PCT/US01/03240, mailed Jun. 6, 2002.
Office Communication, European Application No. 00975164.5, mailed Jun. 4, 2003.
Office Communication, European Application No. 00975164.5, mailed Feb. 11, 2004.
Examiner's Report, Australian Application No. 13255/01, mailed Sep. 3, 2003.
Office Communication, European Application No. 01905306.5, mailed Jan. 23, 2003.
Office Communication, European Application No. 01905306.5, mailed Feb. 16, 2004.
European Search Report, Application No. 02713535.9-2404-US0203275, mailed Feb. 18, 2004.
Written Opinion, Application No. PCT/US03/23131, mailed Feb. 24, 2004.
International Preliminary Examination Report, Application No. PCT/US03/23131, mailed May 18, 2004.
Office Action for U.S. Appl. No. 09/287,248 mailed May 9, 2001.
Office Action for U.S. Appl. No. 09/287,248 mailed Jan. 2, 2002.
Office Action for U.S. Appl. No. 09/287,248 mailed May 2, 2002.
Office Action for U.S. Appl. No. 09/287,248 mailed Aug. 12, 2002.
Office Action for U.S. Appl. No. 09/287,248 mailed Mar. 11, 2003.
Office Action for U.S. Appl. No. 09/287,248 mailed Aug. 18, 2003.
Office Action for U.S. Appl. No. 09/287,248 mailed Feb. 24, 2004.
Office Action for U.S. Appl. No. 09/354,882 mailed Oct. 3, 2001.
Office Action for U.S. Appl. No. 09/354,882 mailed May 8, 2002.
Office Action for U.S. Appl. No. 09/354,882 mailed Jan. 17, 2003.
Office Action for U.S. Appl. No. 09/616,355 mailed Mar. 15, 2002.
Office Action for U.S. Appl. No. 09/616,355 mailed Aug. 13, 2002.
Office Action for U.S. Appl. No. 09/616,482 mailed Oct. 3, 2001.
Office Action for U.S. Appl. No. 09/616,482 mailed Mar. 27, 2002.
Office Action for U.S. Appl. No. 09/616,482 mailed Aug. 1, 2002.

Office Action for U.S. Appl. No. 09/616,731 mailed Jun. 28, 2004.
Office Action for U.S. Appl. No. 09/775,342 mailed Oct. 2, 2002.
Office Action for U.S. Appl. No. 09/775,342 mailed Feb. 14, 2003.
Office Action for U.S. Appl. No. 09/775,342 mailed Aug. 13, 2002.
Office Action for U.S. Appl. No. 09/775,340 mailed Jul. 29, 2002.
Office Action for U.S. Appl. No. 09/775,340 mailed Oct. 25, 2002.
Office Action for U.S. Appl. No. 09/775,340 mailed Apr. 22, 2003.
Office Action for U.S. Appl. No. 09/775,344 mailed Apr. 16, 2004.
Office Action for U.S. Appl. No. 09/775,353 mailed Feb. 5, 2002.
Office Action for U.S. Appl. No. 09/775,353 mailed Oct. 2, 2002.
Office Action for U.S. Appl. No. 09/775,048 mailed Feb. 6, 2002.
Office Action for U.S. Appl. No. 09/775,048 mailed Sep. 17, 2002.
Office Action for U.S. Appl. No. 09/775,048 mailed Feb. 5, 2003.
Office Action for U.S. Appl. No. 09/775,343 mailed May 10, 2004.
Michael et al., "Making Sensors out of Disarray: Optical Sensor Microarray", SPIE, 1998, vol. 3270, pp. 34-41.
International Search Report for PCT/US99/16162 mailed Nov. 26, 1999.
International Search Report for PCT/US00/19302 mailed Feb. 22, 2001.
International Search Report for PCT/US00/19351 mailed Feb. 22, 2001.
International Search Report for PCT/US00/19350 mailed Feb. 22, 2001.
International Search Report for PCT/US01/03141 mailed Oct. 19, 2001.
International Search Report for PCT/US01/03139 mailed May 7, 2001.
International Search Report for PCT/US01/03240 May 7, 2001.
International Search Report for PCT/US01/03241 mailed May 7, 2001.
International Search Report for PCT/US02/3277 mailed Feb. 13, 2003.
International Search Report for PCT/US02/3275 mailed May 7, 2003.
International Search Report for PCT/US03/12951 mailed Oct. 14, 2003.
International Search Report for PCT/US03/23131 mailed Dec. 12, 2003.
International Search Report, Application No. PCT/US02/03275, mailed May 7, 2003.
"Biosensors respond with colored light," Science News, vol. 152, Nov. 15, 1997, p. 317.
Adler, M; Nicholson, J.D.; Hackley, B.E., Jr. "Efficacy of a novel metalloprotease inhibitor on botulinum neurotoxin B activity" FEBS Lett., 1998, 429, 234-238.
Barany, F. PCR Methods and Applications, 1991, 1, 5-16.
Barany, F., Proc. Natl. Acad. Sci. USA, 1991, 88, 189-193.
Deng, G.; James, T.D.; Shinkai, S.J. Am. Chem. Soc. 1994, 116, 4567-4572.
Förster, Th. Transfer Mechanisms of Electronic Excitation;, Discuss. Faraday Soc., 1959, 27, 7-17.
Goldrick, M.M.; Kimball, G.R.; Liu, Q.: Martin, L.A.; Sommer, S.S.: Tseng, J.Y.H.; "Nirca™—A Rapid Robust Method for Screening for Unknown Point Mutations", BioTechniques, 1996, 21, 106-112.
Grate et al., "Hydrogen Bond Acidic Polymers for Surface Acoustic Wave Vapor Sensors and Arrays," Analytical Chemistry, vol. 71, No. 5, Mar. 1, 1999, pp. 1033-1040.
Guatelli, et al., Proc. Natl. Acad, Sci., 1990, USA, 87, 1874-1878.
Hamasaki, K.; Ikeda, H.; Nakamura, A.; Ueno, A.; Toda, F.: Suzuki, I.; Osa, T. "Fluorescent Sensors of Molecular Recognition. Modified Cyclodextrins Capable of Exhibiting Guest-Responsive Twisted Intramolecular Charge Transfer Fluorescence", J. Am. Chem. Soc., 1993, 115, 5035-5040.
Han et al, "Deflection behavior of Fabry-Perot pressure sensors having planar and corrugated diaphragms," Microelectronics Research Center and Department of Electrical and Computer Engineering, Feb. 4, 1997.
Han et al., "Fabrication and characterization of a Fabry-Perot based chemical sensor," Microelectronics Research Center and Department of Electrical and Computer Engineering, Feb. 7, 1997.
Harrison, 1991, Nature, 353, 715-719.
Healey et al., "Fast Temporal Response Fiber-Optic Chemical Sensors Based on the Photodeposition of Micrometer-Scale Polymer Arrays," Analytical Chemistry, vol. 69, No. 11, Jun. 1, 1997, pp. 2213-2216.
Holtz et al., "Intelligent Polymerized Crystalline Colloidal Arrays: Novel Chemical Sensor Materials," Analytical Chemistry,.vol. 70, No. 4, Feb. 15, 1998, pp. 780-791.
Hsu, I.C.; Yang, Q.P.; Kahng, M.W.; Xu, J.F.; "Detection of DNA Point Mutations with DNA Mismatch Repair Enzymes", Carcinogenesis, 1994, 15, 1657-1662.
James T. D.; Murata, K.; Harada, T.; Ueda, K.; Shinkai, S.Chem. Lett. 1994, 273-276.
James T.D.; Sandanayake, K.R.A.S.; Shinkai, S. Nature, 1995, 374, 345-347.
James T.D.; Sandanayake, K.R.A.S.; Shinkai, S.,Angew. Chem., Int. Ed. Eng. 1994, 33, 2207-2209.
James, T.D.; Sandanayake, K.R.A.S.; Iguchi, R.; Shinkai, S.J. Am. Chem. Soc. 1995, 117, 8982-8987.
James, T.D.; Harada, T.; Shinkai, S.J. Chem. Soc. Chem. Commun. 1993, 857-860.
James, T.D.; Sandanayake, K.R.A.S.; Shinkai, S.,J. Chem. Soc., Chem. Commun. 1994, 477-478.
Johnson et al., "Identification of Multiple Analytes Using an Optical Sensor Array and Pattern Recognition Neural Networks," Analytical Chemistry, vol. 69, No. 22, Nov. 15, 1997, pp. 4641-4648.
Kaiser, E.; Colescott, R.L.; Bossinger, C.D.; Cook, P.I.; "Color Test for Detection of Free Terminal Amino Groups in the Solid-Phase Synthesis of Peptides", Anal. Biochem., 1970, 34, 595-598.
Khanna, P.L., Ullman, E.F. "4', 5'—Dimethoxyl-6-carboxyfluorescein; A novel dipole-dipole coupled fluorescence energy transfer acceptor useful for fluorescence immunoassays", Anal. Biochem. 1980, 108, 156-161.
Klug A., Gene 1993, 135-83-92.
Kondo, K.; Shiomi, Y.; Saisho, M.; Harada, T.; Shinkai, S. Tetrahedron. 1992, 48, 8239-8252.
Kwoh, et al., Proc. Natl. Acad. Sci., USA, 1989, 86, 1173-1177.
Lavigne et al., "Solution-Based Analysis of Multiple Analytes by a Sensor Array: Toward the Development of an Electronic Tongue," J. Am. Chem. Soc., vol. 120, No. 25, Jul. 1, 1998, pp. 6429-6430.
Ludwig, R.; Harada, T.; Ueda, K.; James, T.D.; Shinkai, S.J., Chem. Soc. Perkin Trans 2. 1994, 697-702.
Morrison, L.E. "Time resolved Detection of Energy Transfer: Theory and Application to Immunoassays", Anal. Biochem. 1988, 174, 101-120.
Mullis K.B.; and Faloona, F.A., Methods Enzymol., 1987, 155, 335-350.
Mullis, et al., Cold Springs Harbor Symp. Quant. Biol., 1986, 51, 263-273.
Murakami, H.; Nagasaki, T.; Hamachi, I.; Shinkai, S., J. Chem. Soc. Perkin Trans 2. 1994, 975-981.
Murukami, H.; Nagasaki, T.; Hamachi, I.; Shinkai, S. Tetrahedron Lett., 1993, 34, 6273-6276.
Nagasaki, T.; Shinmori, H.; Shinkai, S. Tetraliedron Lett. 1994, 35, 2201-2204.
Nakashima, K.; Shinkai, S,.Chem. Lett. 1994, 1267-1270.
Niikura, K.; Metzger, A.; Anslyn, E.V., "A Sensing Ensemble with Selectivity for Iositol Triphosphate", J. Am. Chem. Soc., 1998, 120, 8533-8534.
Pabo and Sauer, 1992, Annu. Rev. Biochem, 61, 1053-1095.
Potyrailo et al., "Optical Time-of-Flight Chemical Detection: Absorption-Modulated Fluorescence for Spatially Resolved Analyte Mapping in a Bidirectional Distributed Fiber-Optic Sensor," Analytical Chemistry, vol. 70, No. 16, Aug. 15, 1998, pp. 3407-3412.
Ricco et al, "Surface Acoustic Wave Chemical Sensor Arrays: New Chemically Sensitive Interfaces Combined with Novel Cluster Analysis to Detect Volatile Organic Compounds and Mixtures," Accounts of Chemical Research, vol. 31, No. 5, 1998, pp. 289-296.
Saiki, et al., Science, 1985, 230, 1350-1354.
Sandanayake, K.R.A.S.; Nakashima, K.; Shinkai, S.J., Chem. Soc.,Chem. Commun. 1994, 1621-1622.
Sandanayake, K.R.A.S; Shinkai, S.J. Chem. Soc., Chem. Commun. 1994, 1083-1084.

Schmidt, J.J.; Stafford, R.G.; Bostian, K.A.; "Type A botulinum neurotoxin proteolytic activity: development of competitive inhibitors and implications for substrate specificity at the $S_1'$ binding subsite", FEBS Lett., 1998, 435, 61-64.
Shinkai, S.; Tsukagohsi, K.; Ishikawa, Y.; Kunitake, T.J. Chem. Soc. Chem. Commun. 1991, 1039-1041.
Shiomi, Y.; Saisho, M.; Tsukagoshi, K.; Shinkai, S.J. Chem. Soc. Perkin Trans I 1993, 2111-2117.
Shone, C.C.; Roberts, A.K., "Peptide substrate specificity and properties of the zinc endopetidase activity of botulinum type B neurotoxin", Eur. J. Biochem., 1994, 225, 263-270.
Soleihac, J.-M.; Cornille, F.; Martin, L.; Lenoir, C.; Fournie-Zaluski, M.-C.; Rogues, B.P. A sensitive and rapid fluorescence-based assay for determination of tetanus toxin peptidase activity: Anal. Biochem., 1996, 241, 120-127.
Stanley, "UT scientists engineer a tiny arbiter of taste," Austin American Statesman, Jul. 26, 1998.
Stimpson, D.I.; Hoijer, J.V.; Hsieh, W.T.; Jou, C.; Gordon, J.; Theriault, T.; Gamble, R.; Baldeschwieler, J.D.; Proc. Natl. Acad. Sci. USA 1995, 92, 6379-6383.
White et al., "Rapid Analyte Recognition in a Device Based on Optical Sensors and the Olfactory System," Analytical Chemistry, vol. 68, No. 13, Jul. 1, 1996, pp. 2191-2202.
Wu D.Y.; Wallace, R.B., Genomics, 1989, 4:560-569.
Youil R; Kemper, B; Cotton, RGH, "Detection of 81 of 81 Known Mouse Beta-Globin Promoter Mutations with T4 Endonuclease-VII—The EMC Method", Genomics, 1996, 32, 431-5.
Cho et al., "An Unnatural Biopolymer," *Science*, 1993, 261, p. 1303-1305.
Schutz et al., "Direct Observation of Ligand Colocalization on Individual Receptor Molecules," *Biophysical Journal*, 1998, 74.
Lauritzen et al., "Peptide Dot Immunoassay and Iimmunoblotting: Electroblotting from Aluminum Thin-layer Chromatography Plates and Isoelectric Focusing Gels to Activated Nitrocellulose," *Electrophoresis*, 1993, 14, p. 852-859.
"Examiner's first report on patent application No. 2003228711 by Board of Regents, The University of Texas System," issued in Australian patent application No. 203228711, dated Sep. 26, 2007.
Savoy et al., "Solution-Based Analysis of Multiple Analytes by a Sensor Array: Toward the Development of an "Electronic Tongue,"" *SPIE Conference on Chemical Microsensors and Applications*, SPIE vol. 3539, Boston, MA, Nov. 4, 1998.
Office Communication, issued in European Application No. 03726746.9, dated Jun. 19, 2008.
Keavney, "Plasma C-reactive protein (CRP), a novel cardiovascular risk factor, shows high heritability but no association with the -174 G/C polymorphism of the interleukin-6 (IL-6) gene in human families," *Abstracts from the American Heart Association Scientific Sessions 2000*, 102:329, 2000.
Meier-Ewert et al., "Absence of diurnal variation of C-reactive protein concentrations in healthy human subjects," *Clinical Chemistry*, 47:426-430, 2001.
Ridker et al., "C-reactive protein and other markers of inflammation in the prediction of cardiovascular disease in women," *The New England Journal of Medicine*, 342(12):836-843, 2000.
Rosano, "Increased C-reactive protein levels in women at increased cardiovascular risk predict one-year events only when associated with increased Interleukin-6 levels," *Journal of The American College of Cardiology*, Supplement A, 39:273A, 2002.
Vickers et al., "Genotype at a promoter polymorphism of the interleukin-6 gene is associated with baseline levels of plasma C-reactive protein," *Cardiovascular Research*, 53:1029-1034, 2002.

McDevitt, "Electronic Taste Chip Research" presented in Bethesda, MD, Nov. 12, 2001, 14 pages.
Meathrel et al., "The effects of hydrophilic adhesives on sample flow," IVD Technology, 2001, 14 pages.
International Preliminary Examination Report for International Application No. PCT/US03/23131 mailed May 18, 2004, 12 pages.
International Search Report and Written Opinion for International Application No. PCT/US04/03751 mailed Aug. 20, 2004, 9 pages.
International Search Report for International Application No. PCT/US04/03610 mailed Jan. 25, 2005, 3 pages.
Written Opinion for International Application No. PCT/US04/03610 mailed Jan. 25, 2005, 7 pages.
International Search Report and Written Opinion for International Application No. PCT/US2005/006077 mailed Jul. 26, 2005, 8 pages.
Invitation to Pay Additional Fees for International Application No. PCT/US2004/041633 mailed Jun. 17, 2005, 6 pages.
Invitation to Pay Additional Fees for International Application No. PCT/US2005/006074 mailed Aug. 3, 2005, 6 pages.
Office communication for U.S. Appl. No. 09/775,342 mailed Feb. 14, 2003, 14 pages.
Office communication for U.S. Appl. No. 09/775,342 mailed Aug. 13, 2002, 12 pages.
Office communication for U.S. Appl. No. 09/775,340 mailed Oct. 25, 2002, 9 pages.
Office communication for U.S. Appl. No. 09/775,340 mailed Apr. 22, 2003, 13 pages.
Office communication for U.S. Appl. No. 09/775,344 mailed Apr. 16, 2004, 13 pages.
Office communication for U.S. Appl. No. 09/775,344 mailed Sep. 10, 2004, 33 pages.
Office communication for U.S. Appl. No. 09/775,048 mailed Feb. 6, 2002, 13 pages.
Office communication for U.S. Appl. No. 09/775,048 mailed Sep. 17, 2002, 12 pages.
Office communication for U.S. Appl. No. 09/775,343 mailed May 10, 2004, 18 pages.
Office communication for U.S. Appl. No. 09/775,343 mailed Nov. 22, 2004, 12 pages.
Office communication for U.S. Appl. No. 09/775,344 mailed Apr. 5, 2005, 25 pages.
European communication for European Application No. 02 713 535.9 mailed Oct. 6, 2005, 4 pages.
Office communication for U.S. Appl. No. 10/072,800 mailed Jun. 28, 2005, 10 pages.
Office communication for U.S. Appl. No. 11/039,054 mailed Oct. 18, 2005, 13 pages.
Office Action for U.S. Appl. No. 09/616,731 mailed Apr. 19, 2005, 15 pages.
International Search Report and Written Opinion for International Application No. PCT/US2004/041633 mailed Nov. 14, 2005.
European Patent Office "Communication pursuant to Article 96(2) EPC" for EP Application No. 00975164.5 mailed Nov. 11, 2005, 2 pages.
Office communication for U.S. Appl. No. 11/010,816 mailed Nov. 7, 2005, 17 pages.
Co-Pending U.S. Appl. No. 10/470,646, filed Jan. 24, 2005.
Co-Pending U.S. Appl. No. 10/522,499, filed Jan. 24, 2005.
Co-Pending U.S. Appl. No. 10/552,926, filed Jan. 24, 2005.
Co-Pending U.S. Appl. No. 11/022,176, filed Dec. 22, 2004.
Co-Pending U.S. Appl. No. 11/020,442, filed Dec. 22, 2004.
Co-Pending U.S. Appl. No. 11/022,365, filed Dec. 22, 2004.
Co-Pending U.S. Appl. No. 11/021,219, filed Dec. 22, 2004.

* cited by examiner

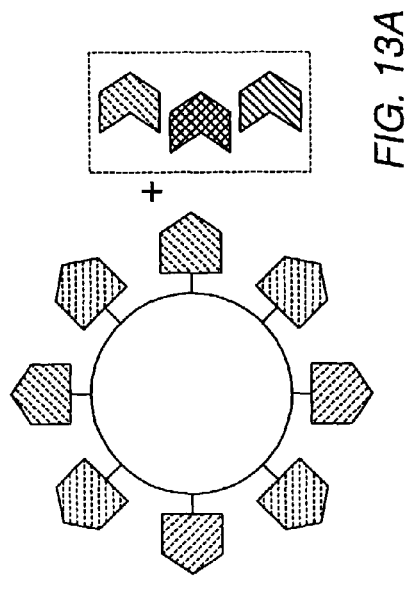
FIG. 13A
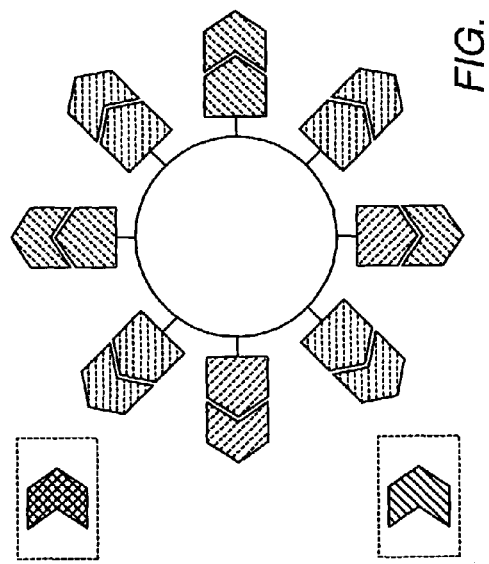
FIG. 13B
FIG. 13C
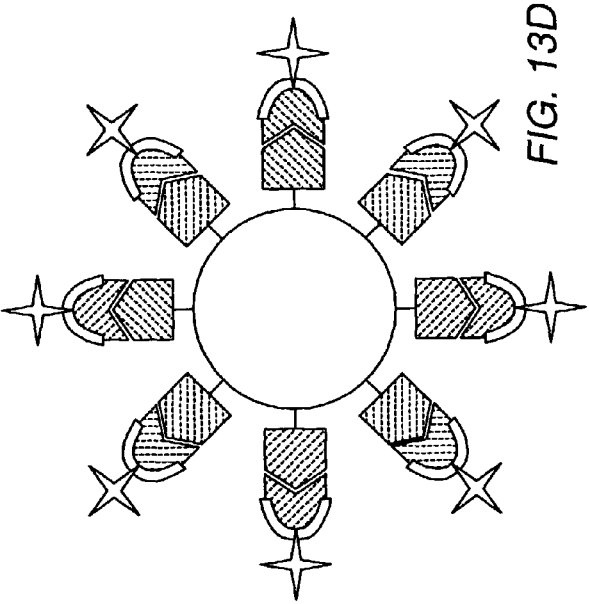
FIG. 13D

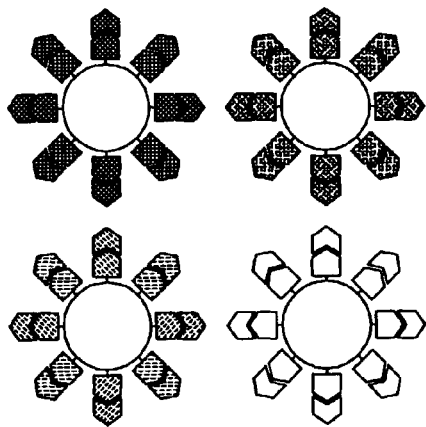
FIG. 14A
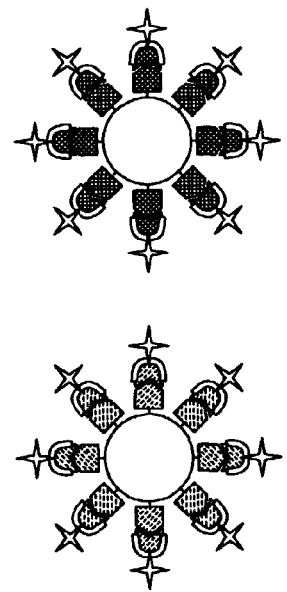
FIG. 14B
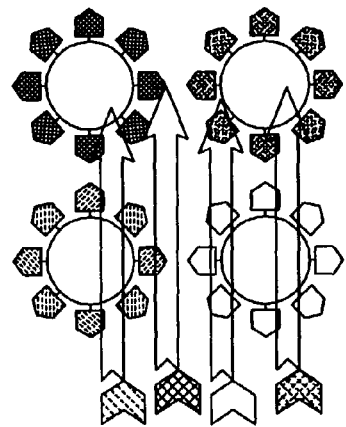
FIG. 14C
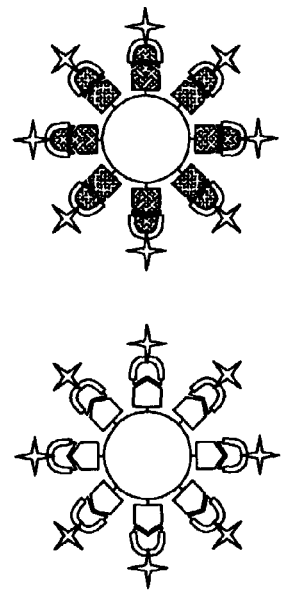
FIG. 14D
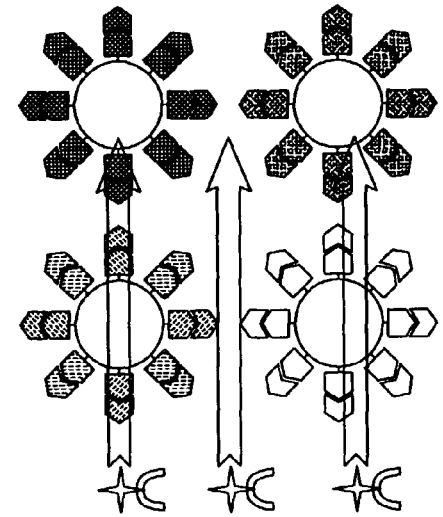

METHOD AND SYSTEM FOR THE DETECTION OF CARDIAC RISK FACTORS

PRIORITY CLAIM

This application claims priority to Provisional Patent Application No. 60/375,775 entitled "METHOD AND SYSTEM FOR THE DETECTION OF CARDIAC RISK FACTORS" filed on Apr. 26, 2002.

This invention was made with government support under GM057306 awarded by the National Institutes of Health; and under 9631394 awarded by the National Science Foundation. The government has certain rights in the invention.

BACKGROUND OF THE INVENTION

1. Field of the Invention

The present invention relates to a method and device for the detection of analytes in a fluid. More particularly, the invention relates to the development of a sensor array system capable of discriminating mixtures of cardiovascular risk factor analytes for the prediction of coronary heart disease.

2. Brief Description of the Related Art

Coronary heart disease (CHD) is the leading cause of death in developed countries. In the United States alone, more than half a million people die each year from sudden cardiac arrest or from the consequences of chronic heart disease. The etiology of this common and often fatal disease is complex and multi-factorial. Current screening and management strategies for the prevention of CHD target some of the plasma-based factors as predictors of cardiovascular risk. The typical analytical methods used for their measurement, however, are rather inefficient. These tests typically require long assay times, sophisticated instrumentation and significant amounts of expensive reagents. Furthermore, these analytical methods are generally limited to measuring just one analyte at a time. A more efficient, rapid and inexpensive analytical system that targets numerous risk factors concurrently and one that may be customized for specific clinical settings would likely allow for a comprehensive and, thus, more reliable risk assessment for CH). Therefore, the development of such a system could have a profound influence on the treatment and prevention of this important disease.

Indeed, the areas of multianalyte immunoassays and immunosensors recently have become the focus of active research aiming for the use of smaller sample volumes, shorter assay times, simpler assay protocols, reduced cost per test and larger information acquisition. For example, multi-analyte array methods based both on dye labels and spatial resolution have been reported. These array themes, however, have yet to be employed specifically to the cardiac theme.

SUMMARY OF THE INVENTION

Herein we describe systems and methods for the analysis of a fluid containing one or more cardiac risk factor analytes. The system, in some embodiments, may generate patterns that are diagnostic for both individual analytes and mixtures of analytes. The system, in some embodiments, includes a plurality of chemically sensitive particles, formed in an ordered array, capable of simultaneously detecting many different kinds of analytes rapidly. An aspect of the system may be forming the array using microfabrication processing, thus allowing the system to be manufactured in an inexpensive manner.

In an embodiment of a system for detecting analytes, the system, in some embodiments, includes a light source, a sensor array, and a detector. The sensor array, in some embodiments, is formed of a supporting member formed to hold a variety of chemically sensitive particles (herein referred to as "particles") in an ordered array. The particles are, in some embodiments, elements, which will create a detectable signal in the presence of an analyte. The particles may produce optical (e.g., absorbance or reflectance) or fluorescence/phosphorescent signals upon exposure to an analyte. A detector (e.g., a charge-coupled device, "CCD"), in one embodiment, is positioned below the sensor array to allow for data acquisition. In another embodiment, the detector may be positioned above the sensor array to allow for data acquisition from reflectance of light off particles.

Light originating from the light source may pass through the sensor array and out through the bottom side of the sensor array. Light modulated by the particles may pass through the sensor array and onto the proximally spaced detector. Evaluation of the optical changes may be completed by visual inspection or by use of a CCD detector by itself or in combination with an optical microscope. A microprocessor may be coupled to the CCD detector or the microscope. A fluid delivery system may be coupled to the supporting member of the sensor array. The fluid delivery system, in some embodiments, introduces samples into and out of the sensor array.

In an embodiment, a sensor array system includes an array of particles. The particles may include a receptor molecule coupled to a polymeric bead. The receptors, in some embodiments, are chosen for interacting with analytes. This interaction may take the form of a binding/association of the receptors with the analytes. The supporting member may be made of any material capable of supporting the particles. The supporting member may allow the passage of the appropriate wavelengths of light. Light may pass through all of or portion of the supporting member. The supporting member may include a plurality of cavities. The cavities may be formed such that at least one particle is substantially contained within the cavity.

In an embodiment, an optical detector may be integrated within the bottom of the supporting member, rather than using a separate detecting device. The optical detectors may be coupled to a microprocessor to allow evaluation of fluids without the use of separate detecting components. Additionally, a fluid delivery system may also be incorporated into the supporting member. Integration of detectors and a fluid delivery system into the supporting member may allow the formation of a compact and portable analyte sensing system.

A high sensitivity CCD array may be used to measure changes in optical characteristics, which occur upon binding of biological/chemical agents. The CCD arrays may be interfaced with filters, light sources, fluid delivery, and/or micro-machined particle receptacles to create a functional sensor array. Data acquisition and handling may be performed with existing CCD technology. CCD detectors may be used to measure white light, ultraviolet light or fluorescence. Other detectors such as photomultiplier tubes, charge induction devices, photo diodes, photodiode arrays, and microchannel plates may also be used.

In an embodiment, the sensor array system includes an array of particles. The particles may include a receptor molecule coupled to a polymeric bead. The receptors, in some embodiments, are chosen for interacting with analytes. This interaction may take the form of a binding/association of the receptors with the analytes. The supporting member may be made of any material capable of supporting the particles. The supporting member may allow the passage of the appropriate wavelengths of light. Light may pass through all of or portions of the supporting member. The supporting member may include a plurality of cavities. The cavities may be formed such that at least one particle is substantially contained within the cavity. A vacuum may be coupled to the cavities. The vacuum may be applied to the entire sensor array. Alternatively, a vacuum apparatus may be coupled to the cavities to provide a vacuum to the cavities. A vacuum apparatus is any device capable of creating a pressure differential to cause fluid movement. The vacuum apparatus may apply a pulling force to any fluids within the cavity. The vacuum apparatus may pull the fluid through the cavity. Examples of vacuum apparatuses include a pre-sealed vacuum chamber, vacuum pumps, vacuum lines, or aspirator type pumps.

A particle, in some embodiments, may possess both the ability to bind the analyte of interest and to create a modulated signal. The particle may include receptor molecules which posses the ability to bind the analyte of interest and to create a modulated signal. Alternatively, the particle may include receptor molecules and indicators. The receptor molecule may posses the ability to bind to an analyte of interest. Upon binding the analyte of interest, the receptor molecule may cause the indicator molecule to produce the modulated signal.

A variety of natural and synthetic receptors may be used. The receptor molecules may be naturally occurring or synthetic receptors formed by rational design or combinatorial methods. Some examples of natural receptors include, but are not limited to, DNA, RNA, proteins, enzymes, oligopeptides, antigens, and antibodies. In one embodiment, a naturally occurring or synthetic receptor is bound to a polymeric bead in order to create the particle. The particle, in some embodiments, is capable of both binding the analyte(s) of interest and creating a detectable signal. In some embodiments, the particle will create an optical signal when bound to an analyte of interest. Either natural or synthetic receptors may be chosen for their ability to bind to the analyte molecules in a specific manner.

The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers. Polynucleotides are relatively small fragments of DNA, which may be derived by sequentially building the DNA sequence. Peptides may include natural peptides, such as antibodies or enzymes or synthesized from amino acids. Unnatural biopolymers are chemical structures which are based on natural biopolymers, but which are built from unnatural linking units. For example, polythioureas and polyguanidiniums may be synthesized from diamines (i.e., compounds that include at least two amine functional groups) rather than amino acids and have a structure similar to peptides. Synthetic receptors are designed organic or inorganic structures capable of binding various analytes.

In an embodiment, a large number of chemical/biological agents of interest to the military and civilian communities may be sensed readily by the described array sensors. Bacteria may also be detected using a similar system. To detect, sense, and identify intact bacteria, the cell surface of one bacterium may be differentiated from other bacteria, or genomic material may be detected using oligonucleic receptors. One method of accomplishing this differentiation is to target cell surface oligosaccharides (i.e., sugar residues). Synthetic receptors, which are specific for oligosaccharides, may be used to determine the presence of specific bacteria by analyzing for cell surface oligosaccharides.

In one embodiment, a receptor may be coupled to a polymeric resin. The receptor may undergo a chemical reaction in the presence of an analyte such that a signal is produced. Indicators may be coupled to the receptor or the polymeric bead. The chemical reaction of the analyte with the receptor may cause a change in the local microenvironment of the indicator to alter the spectroscopic properties of the indicator. The signal may be produced using a variety of signaling protocols. Such protocols may include absorbance, fluorescence resonance energy transfer, and/or fluorescence quenching. Receptor-analyte combinations may include, but are not limited to, peptides-proteases, polynucleotides-nucleases, and oligosaccharides- oligosaccharide cleaving agents.

In one embodiment, a receptor and an indicator may be coupled to a polymeric resin. The receptor may undergo a conformational change in the presence of an analyte such that a change in the local microenvironment of the indicator occurs. This change may alter the spectroscopic properties of the indicator. The interaction of the receptor with the indicator may be produce a variety of different signals depending on the signaling protocol used. Such protocols may include absorbance, fluorescence resonance energy transfer, and/or fluorescence quenching.

In an embodiment, a receptor may be coupled to a polymeric resin. The receptor may interact with the analyte to form a particle-analyte complex. A visualization reagent may be applied to the particle-analyte complex, which may produce a variety of different signals depending on the signaling protocol used. The visualization of the complex may include addition of dyes, stains or may include fluorescence resonance energy transfer, absorbance, and/or fluorescence quenching.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 13A-D depicts a general scheme for the testing of an antibody analyte of an embodiment of a sensor array system;

FIG. 14A-D depicts a general scheme for the detection of antibodies, of an embodiment of a sensor array composed of four individual beads;

DETAILED DESCRIPTION OF EMBODIMENTS

Herein we describe a system and method for the simultaneous analysis of a fluid containing multiple analytes. The system may generate patterns that are diagnostic for both individual analytes and mixtures of the analytes. The system, in some embodiments, is made of a combination of chemically sensitive particles, formed in an ordered array, capable of simultaneously detecting many different kinds of cardiovascular risk factor analytes rapidly. An aspect of the system is that the array may be formed using a microfabrication process, thus allowing the system to be manufactured in an inexpensive manner.

System for Analytes

Various systems for detecting analytes in a fluid and gases have been described in U.S. Pat. No. 6,045,579, U.S. Patent Application Publication No. US 2002/0197622 and in U.S. patent applications Ser. Nos. 09/287,248; 09/354,882; 09/775,340; 09/775,344; 09/775,353; 09/775,048; and 09/775,343 all of which are incorporated by reference as if fully set forth herein.

Figure 1:
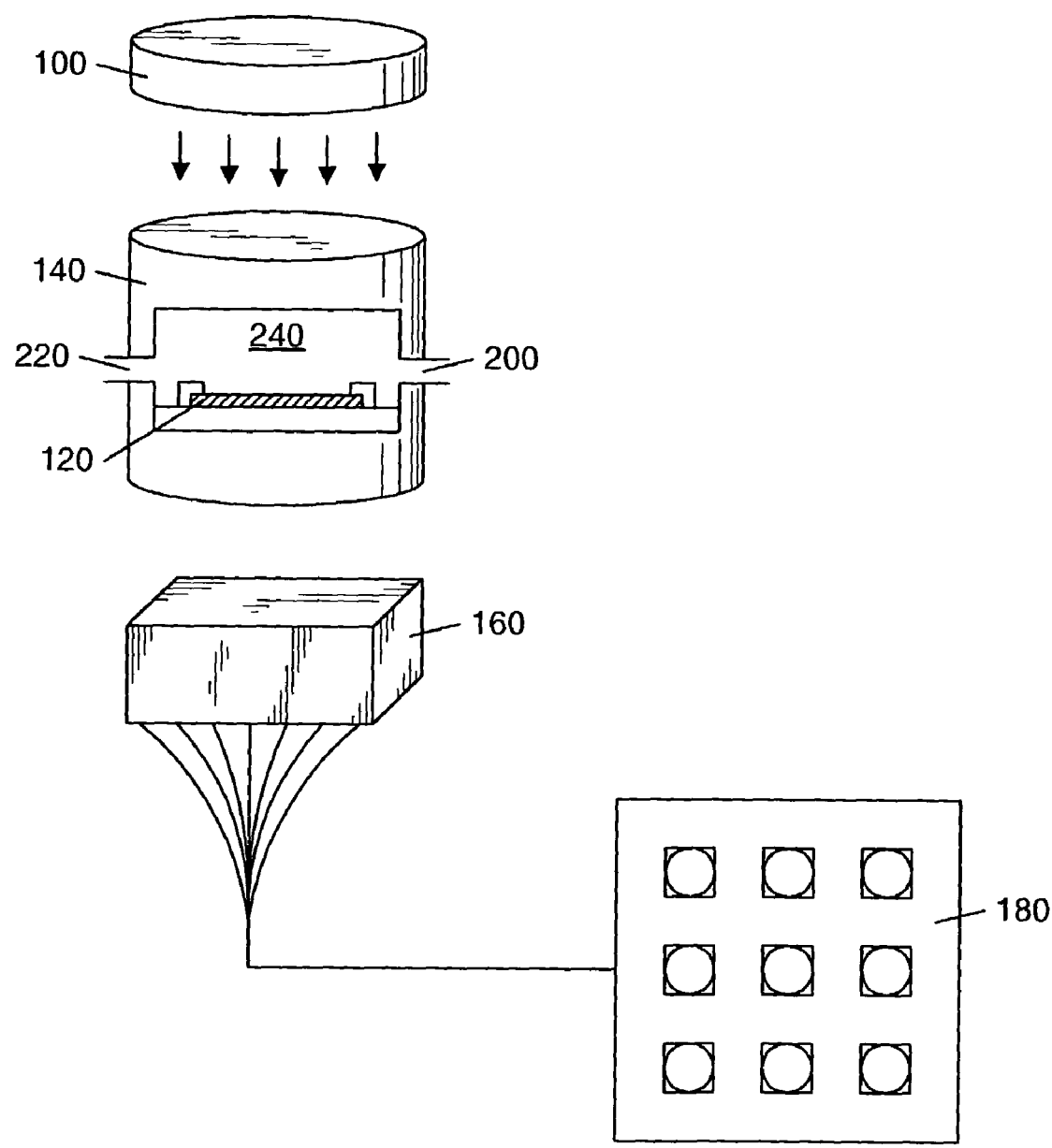
FIG. 1 depicts an embodiment of an analyte detection system, which includes a sensor array disposed within a chamber.

Shown in FIG. 1 is an embodiment of a system for detecting analytes in a fluid. In one embodiment, the system includes light source 100, sensor array 120, chamber 140 for supporting the sensor array, and detector 160. Sensor array 120 may include a supporting member, which is formed to hold a variety of particles. In one embodiment, light originating from light source 100 passes through sensor array 120 and out through the bottom side of the sensor array. Light modulated by the particles may be detected by proximally spaced detector 160. While depicted as being positioned below the sensor array, it should be understood that the detector might be positioned above the sensor array for reflectance measurements. Evaluation of the optical changes may be completed by visual inspection (e.g., by eye, or with the aid of a microscope) or by use of microprocessor 180 coupled to the detector.

In this embodiment, sensor array 120 is positioned within chamber 140. Chamber 140, may allow a fluid stream to pass through the chamber such that the fluid stream interacts with sensor array 120. The chamber may be constructed of glass (e.g., borosilicate glass or quartz) or a plastic material transparent to a portion of the light from the light source. The material should also be substantially unreactive toward the fluid. Examples of plastic materials which may be used to form the chamber include, but are not limited to, acrylic resins, polycarbonates, polyester resins, polyethylenes, polyimides, polyvinyl polymers (e.g., polyvinyl chloride, polyvinyl acetate, polyvinyl dichloride, polyvinyl fluoride, etc.), polystyrenes, polypropylenes, polytetrafluoroethylenes, and polyurethanes. An example of such a chamber is a Sykes-Moore chamber, which is commercially available from Bellco Glass, Inc., NJ.

Chamber 140, in one embodiment, includes fluid inlet port 200 and fluid outlet port 220. Fluid inlet 200 and outlet 220 ports allow a fluid stream to pass into interior 240 of the chamber during use. The inlet and outlet ports may allow facile placement of a conduit for transferring the fluid to the chamber. In one embodiment, the ports are hollow conduits. The hollow conduits may have an outer diameter substantially equal to the inner diameter of a tube for transferring the fluid to or away from the chamber. For example, if a plastic or rubber tube is used for the transfer of the fluid, the internal diameter of the plastic tube is substantially equal to the outer diameter of the inlet and outlet ports.

In another embodiment, the inlet and outlet ports may be Luer lock style connectors. The inlet and outlet ports may be female Luer lock connectors. The use of female Luer lock connectors will allow a fluid to be introduced via a syringe. Typically, syringes include a male Luer lock connector at the dispensing end of the syringe. For the introduction of liquid samples, the use of Luer lock connectors may allow samples to be transferred directly from a syringe to chamber 140. Luer lock connectors may also allow plastic or rubber tubing to be connected to the chamber using Luer lock tubing connectors.

The chamber may substantially confine the fluid passage to interior 240 of the chamber. By confining the fluid to a small interior volume, the amount of fluid required for an analysis may be minimized. The interior volume may be specifically modified for a desired application. For example, for the analysis of small volumes of fluid samples, the chamber may be designed to have a small interior chamber, thus reducing the amount of fluid needed to fill the chamber. For larger samples, a larger interior chamber may be used. Larger chambers may allow a faster throughput of the fluid during use.

Figure 2:
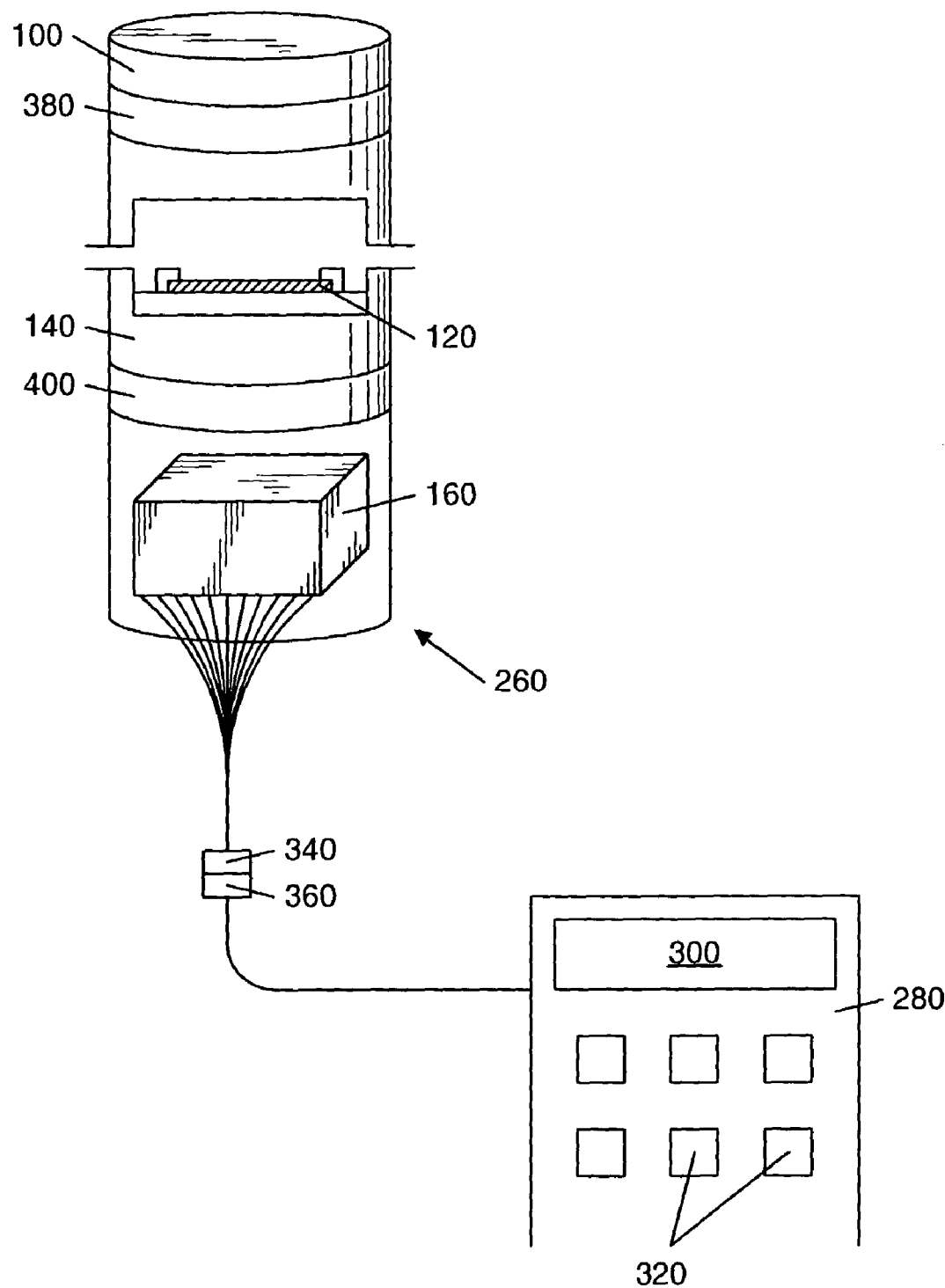
FIG. 2 depicts an embodiment of an integrated analyte detection system.

In another embodiment, depicted in FIG. 2, a system for detecting analytes in a fluid includes light source 100, sensor array 120, chamber 140 for supporting the sensor array, and detector 160, all enclosed within detection system enclosure 260. As described above, sensor array 120 may be formed of a supporting member to hold a variety of particles. Thus, in a single enclosure, all of the components of the analyte detection system may be included.

The formation of an analyte detection system in a single enclosure may allow the formation of a portable detection system. For example, controller 280 may be coupled to the analyte detection system. Controller 280 may interact with the detector and display the results from the analysis. In one embodiment, the controller includes display device 300 for displaying information to a user. The controller may also include input devices 320 (e.g., buttons) to allow the user to control the operation of the analyte detection system. The controller may control operation of light source 100 and operation of detector 160.

Detection system enclosure 260 may be interchangeable with the controller. Coupling members 340 and 360 may be used to remove detection system enclosure 260 from controller 280. A second detection system enclosure may be readily coupled to the controller using coupling members 340 and 360. In this manner, a variety of different types of analytes may be detecting using a variety of different detection system enclosures. Each of the detection system enclosures may include different sensor arrays mounted within their chambers. Instead of having to exchange the sensor array for different types of analysis, the entire detection system enclosure may be exchanged. This may prove advantageous when a variety of detection schemes is used.

For example, a first detection system enclosure may be used for white light applications. The first detection system enclosure may include a white light source, a sensor that includes particles that produce a visible light response in the presence of an analyte, and a detector sensitive to white light. A second detection system enclosure may be used for fluorescent applications, including a fluorescent light source, a sensor array that includes particles, which produce a fluorescent response in the presence of an analyte, and a fluorescent detector. The second detection system enclosure may also include other components necessary for the detection system. For example, the second detection system may also include a filter for preventing short wavelength excitation from producing "false" signals in the optical detection system during fluorescence measurements. A user need only select the proper detection system enclosure for detection of the desired analyte. Since each detection system enclosure includes many of the required components, a user does not have to make light source selections, sensor array selections or detector arrangement selections to produce a viable detection system.

In another embodiment, the individual components of the system may be interchangeable. The system may include coupling members 380 and 400 that allow light source 100 and detector 160, respectively, to be removed from chamber 140. This may allow a modular design of the system. For example, an analysis may be first performed with a white light source to give data corresponding to an absorbance/reflectance analysis. The light source may then be changed to an ultraviolet light source to allow ultraviolet analysis of the particles. Since the particles have already been treated with the fluid, the analysis may be preformed without further treatment of the particles with a fluid. In this manner, a variety of tests may be performed using a single sensor array.

In an embodiment, a supporting member is made of any material capable of supporting the particles while allowing passage of an appropriate wavelength of light. The supporting member may also be made of a material substantially impervious to the fluid in which the analyte is present. A variety of materials may be used including plastics (e.g., photoresist materials, acrylic polymers, carbonate polymers, etc.), glass, silicon based materials (e.g., silicon, silicon dioxide, silicon nitride, etc.) and metals.

In one embodiment, the supporting member includes a plurality of cavities. Each cavity may be formed such that at least one particle is substantially contained within the cavity. In another embodiment, a plurality of particles may be contained within a single cavity.

Figure 3:
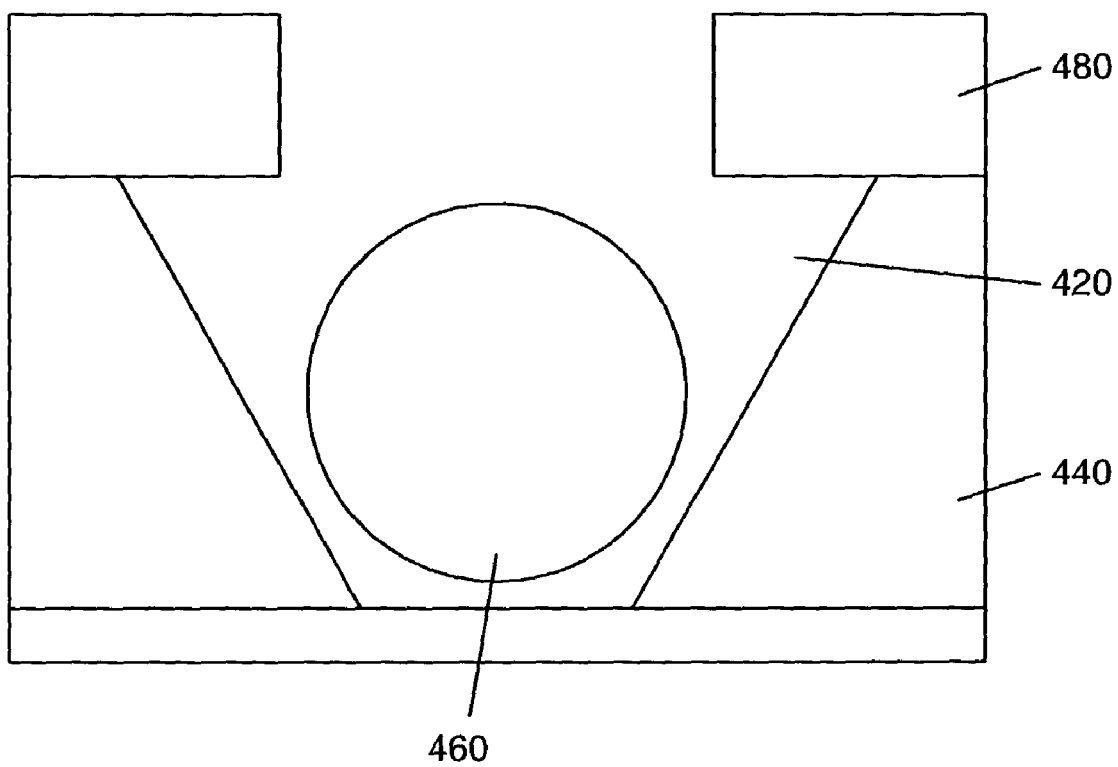
FIG. 3 depicts an embodiment of a sensor array system of a cross-sectional view of a cavity covered by a mesh cover.
Figure 4:
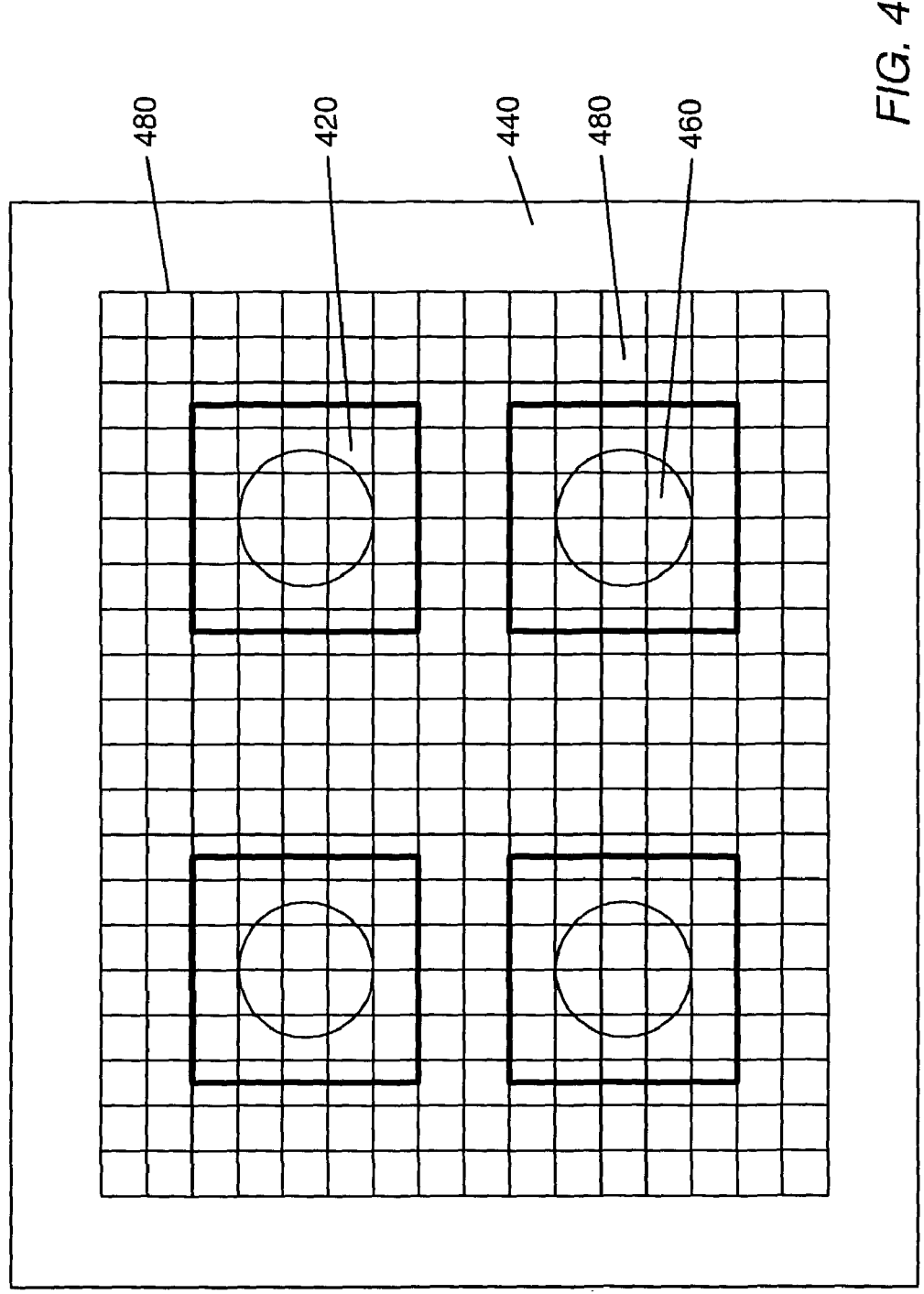
FIG. 4 depicts a top view of a cavity covered by a mesh cover of an embodiment of a sensor array system.

In some embodiments, it may be necessary to pass liquids over the sensor array. The dynamic motion of liquids across the sensor array may lead to displacement of the particles from the cavities. In another embodiment, the particles may be held within cavities formed in a supporting member by the use of a transmission electron microscope ("TEM") grid. As depicted in FIG. 3, cavity 420 is formed in supporting member 440. After placement of particle 460 within the cavity, TEM grid 480 may be placed atop supporting member 440 and secured into position. TEM grids and adhesives for securing TEM grids to a support are commercially available from Ted Pella, Inc., Redding, Calif. TEM grid 480 may be made from a number of materials including, but not limited to, copper, nickel, gold, silver, aluminum, molybdenum, titanium, nylon, beryllium, carbon, and beryllium-copper. The mesh structure of the TEM grid may allow solution access as well as optical access to the particles that are placed in the cavities. FIG. 4 further depicts a top view of a sensor array with TEM grid 480 secured to the upper surface of supporting member 440. TEM grid 480 may be placed on the upper surface of the supporting member to trap particles 460 within cavities 420. As depicted, openings 500 in TEM grid 480 may be sized to hold particles 460 within cavities 420, while allowing fluid and optical access cavities 420.

In another embodiment, a sensor array includes a supporting member formed to support the particles while allowing passage of an appropriate wavelength of light to the particles. The supporting member, in one embodiment, includes a plurality of cavities. The cavities may be formed such that at least one particle is substantially contained within each cavity. The supporting member may be formed to substantially inhibit the displacement of particles from the cavities during use. The supporting member may also allow passage of fluid through the cavities. The fluid may flow from a top surface of the supporting member, past a particle, and out a bottom surface of the supporting member. This may increase the contact time between a particle and the fluid.

Formation of a silicon based supporting member which includes a removable top cover and bottom cover are described in U.S. patent applications Ser. Nos. 09/287,248; 09/354,882; 09/775,340; 09/775,344; 09/775,353; 09/775,048; 09/775,343; 10/072,800 which are incorporated by reference as if fully set forth herein.

Figure 5:
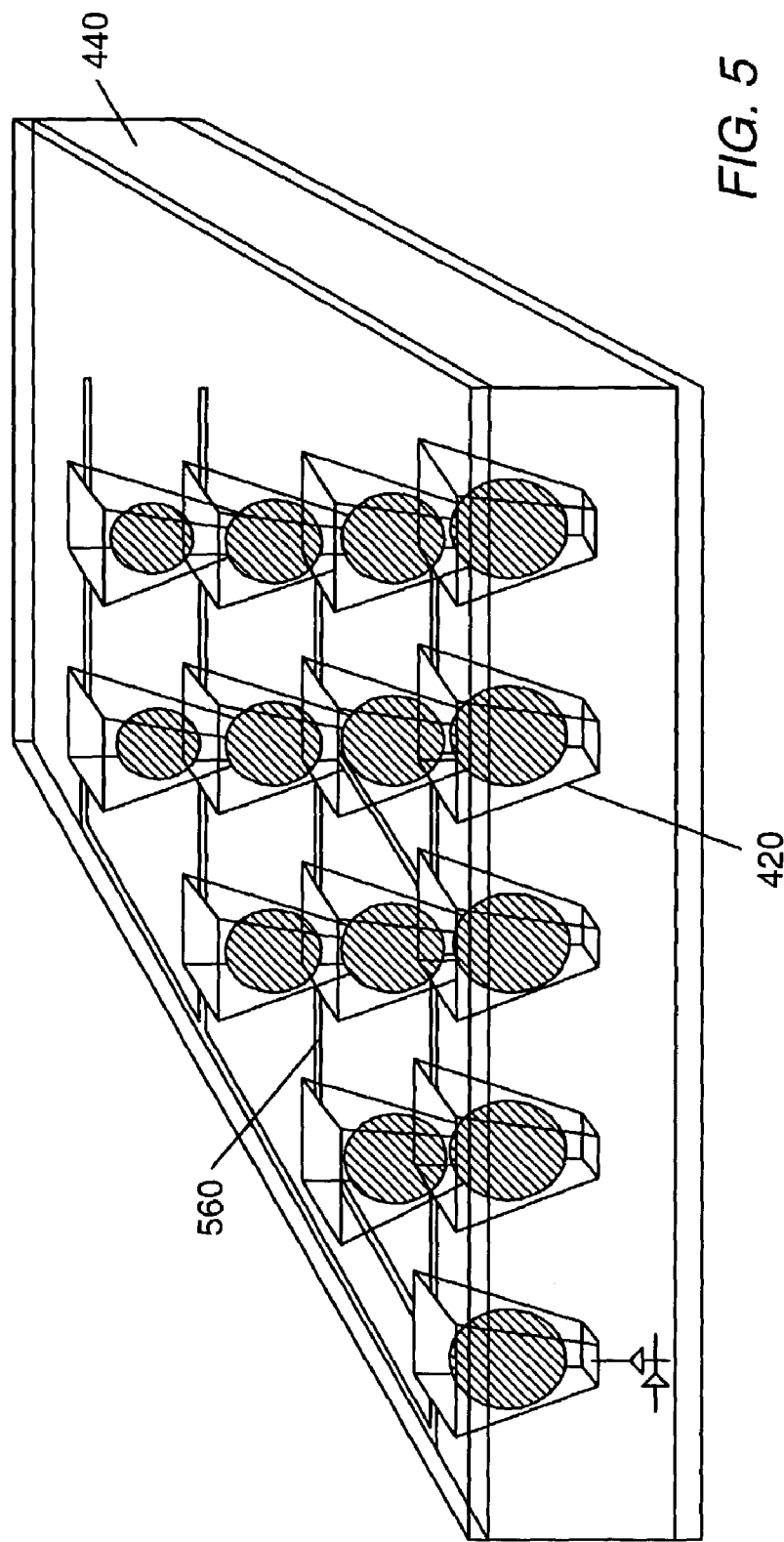
FIG. 5 depicts an embodiment of a sensor array.

In one embodiment, series of channels 520 may be formed in supporting member 440 interconnecting at least some of cavities 420, as depicted in FIG. 5. Pumps and valves may also be incorporated into supporting member 440 to aid passage of the fluid through the cavities. Pumps and valves are described in U.S. patent applications Ser. No. 10/72,800 which is incorporated by reference as if fully set forth herein.

Figure 6:
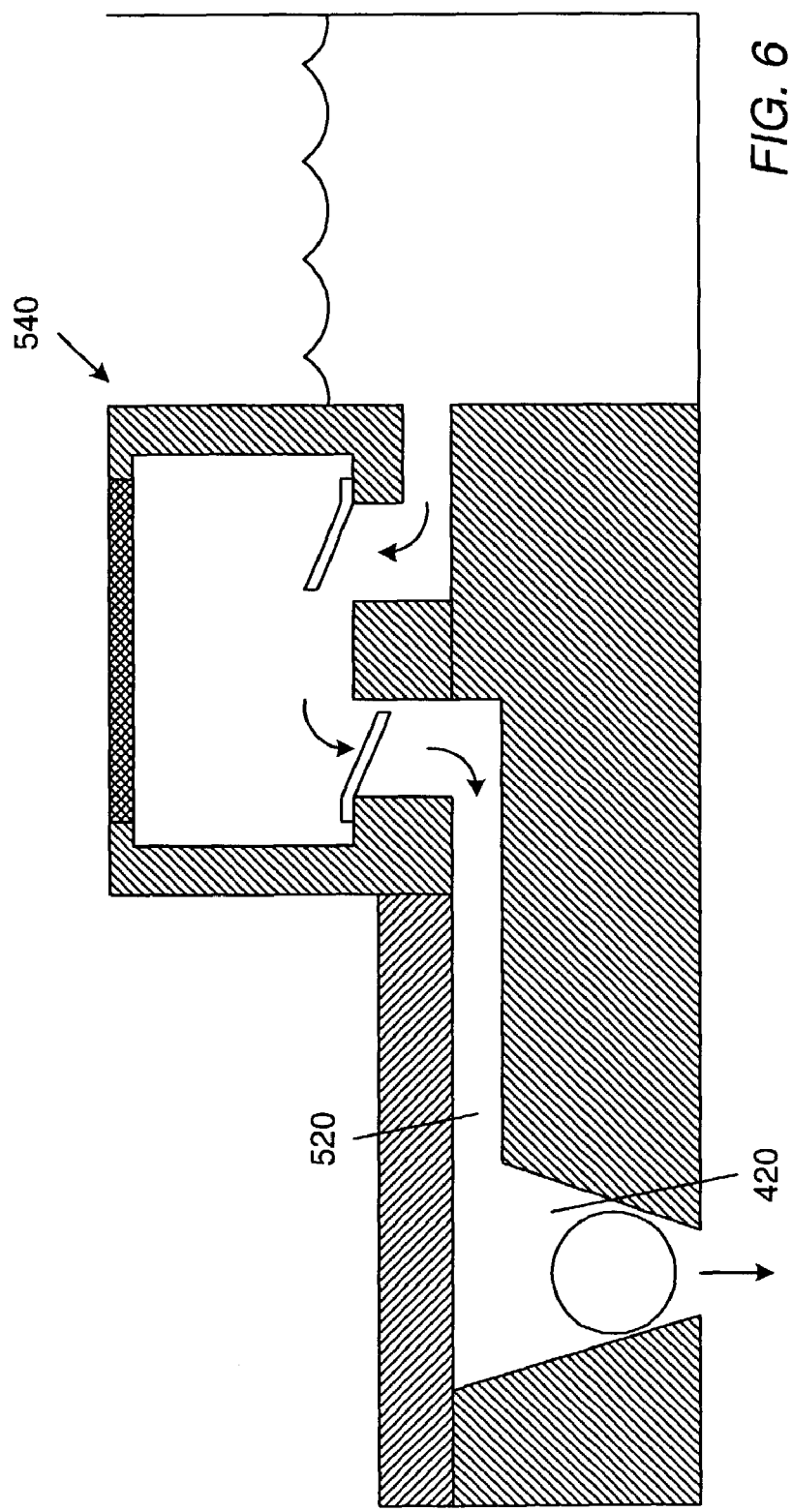
FIG. 6 depicts a cross-sectional view of an embodiment of a sensor array, which includes a micropump.

An advantage of using pumps may be better flow through the channel. The channel and cavities may have a small volume. The small volume of the cavity 420 and channel 520 tends to inhibit flow of fluid through the cavity. By incorporating pump 540, the flow of fluid to the cavity 420 and through the cavity may be increased, allowing more rapid testing of a fluid sample. While a diaphragm based pump system is depicted in FIG. 6, it should be understood that electrode based pumping systems might also be incorporated into the sensor array to produce fluid flows.

Figure 7:
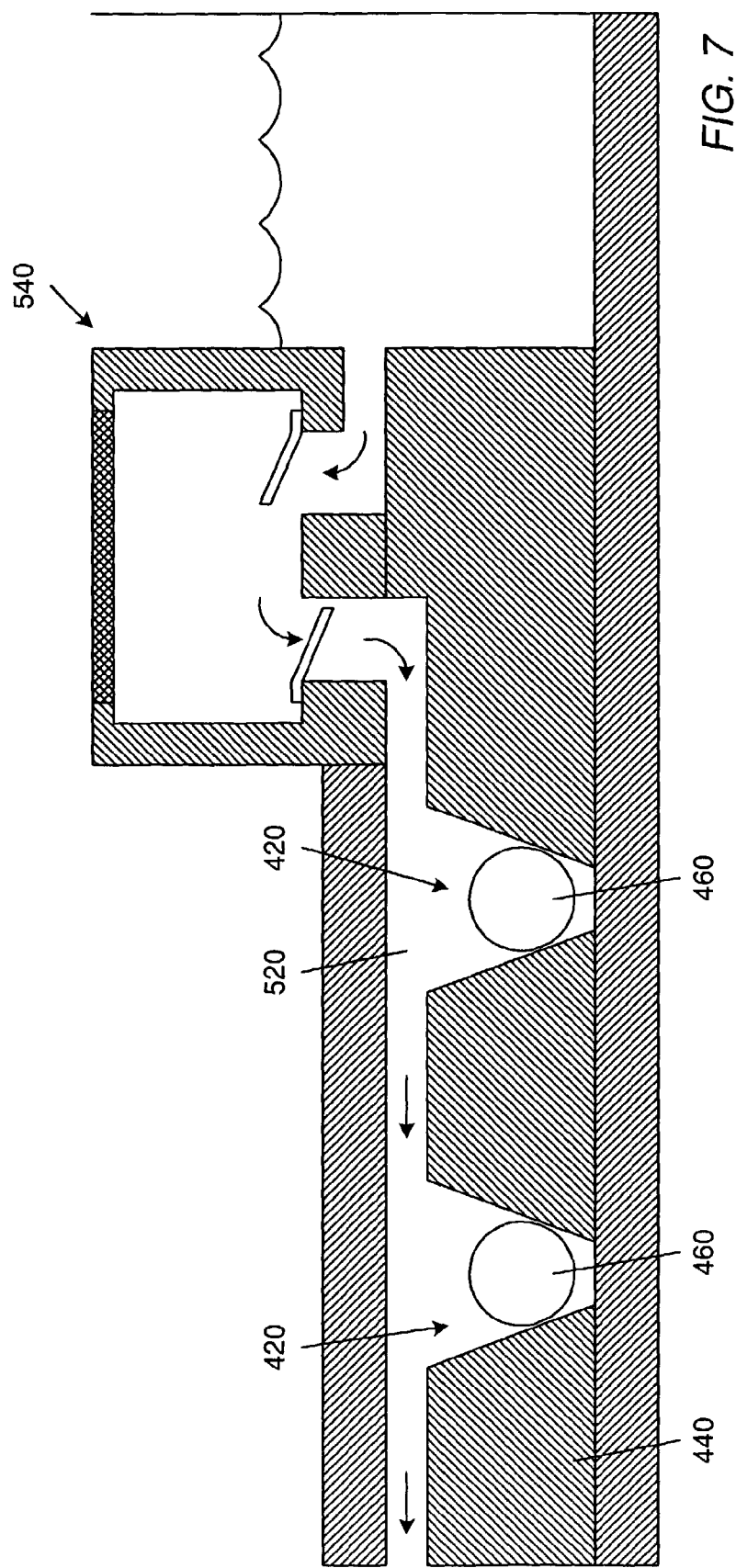
FIG. 7 depicts a cross-sectional view of an embodiment of a sensor array, which includes a micropump and channels, which are coupled to the cavities.

In another embodiment, a pump may be coupled to a supporting member for analyzing analytes in a fluid stream, as depicted in FIG. 7. Channel 520 may couple pump 540 to multiple cavities 420 formed in supporting member 840. Cavities 420 may include sensing particles 460. Pump 540 may create a flow of fluid through channel 520 to cavities 420. In one embodiment, cavities 420 may inhibit the flow of the fluid through the cavities. The fluid may flow into cavities 420 and past particle 460 to create a flow of fluid through the sensor array system. In this manner, a single pump may be used to pass the fluid to multiple cavities. While a diaphragm pump system is depicted in FIG. 7, it should be understood that electrode pumping systems might also be incorporated into the supporting member to create similar fluid flows.

Figure 8:
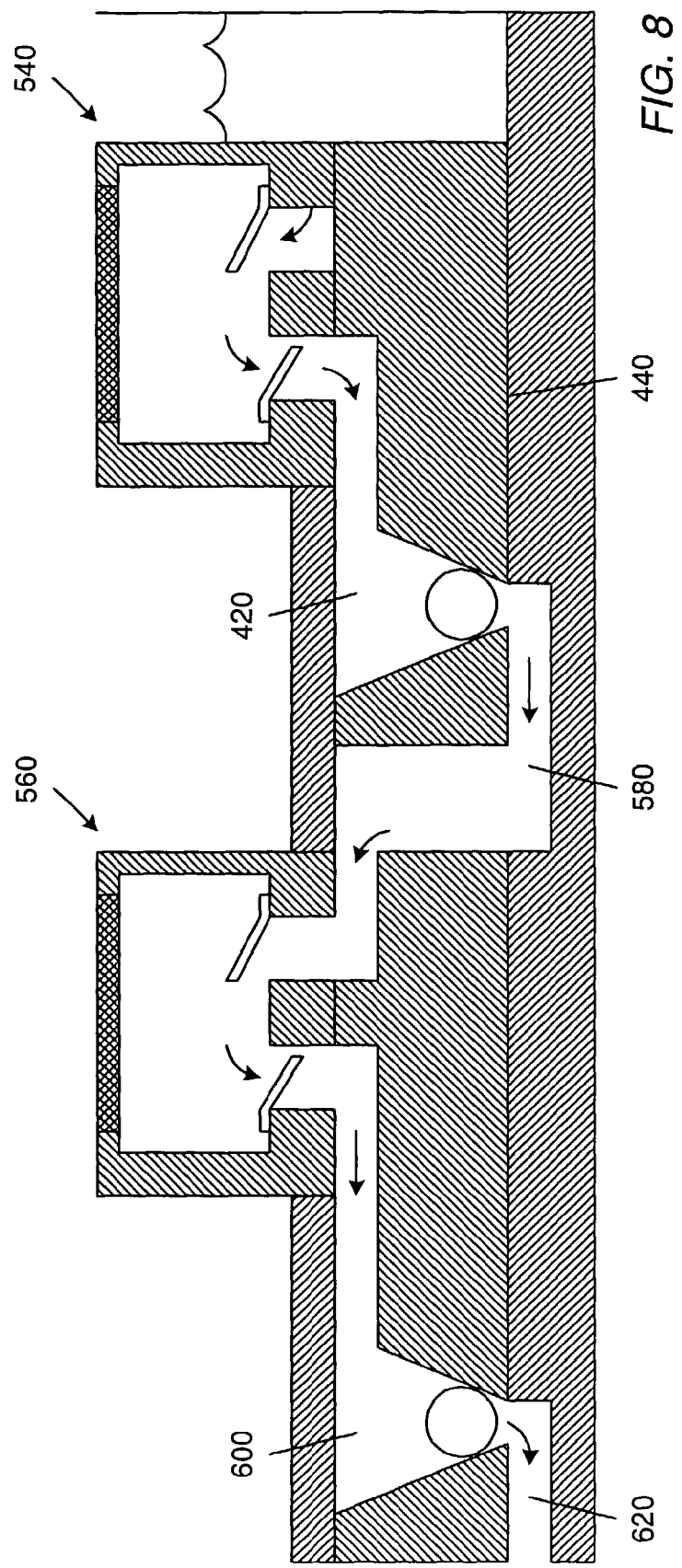
FIG. 8 depicts a cross-sectional view of an embodiment of a sensor array, which includes multiple micropumps, each micropump being coupled to a cavity.

In another embodiment, multiple pumps may be coupled to a supporting member of a sensor array system. The pumps may be coupled in series with each other to pump fluid to each of the cavities. As depicted in FIG. 8, first pump 540 and second pump 560 are coupled to supporting member 440. First pump 540 may be coupled to first cavity 420. The first pump may transfer fluid to first cavity 420 during use. Cavity 420 may allow fluid to pass through the cavity to first cavity outlet channel 580. Second pump 560 may also be coupled to supporting member 440. Second pump 560 may be coupled to second cavity 600 and first cavity outlet channel 580. Second pump 560 may transfer fluid from first cavity outlet channel 580 to second cavity 600. The pumps may be synchronized such that a steady flow of fluid through the cavities is obtained. Additional pumps may be coupled to second cavity outlet channel 620 such that the fluid may be pumped to additional cavities. In one embodiment, each of the cavities in the supporting member is coupled to a pump used to pump the fluid stream to the cavity.

Figure 9:
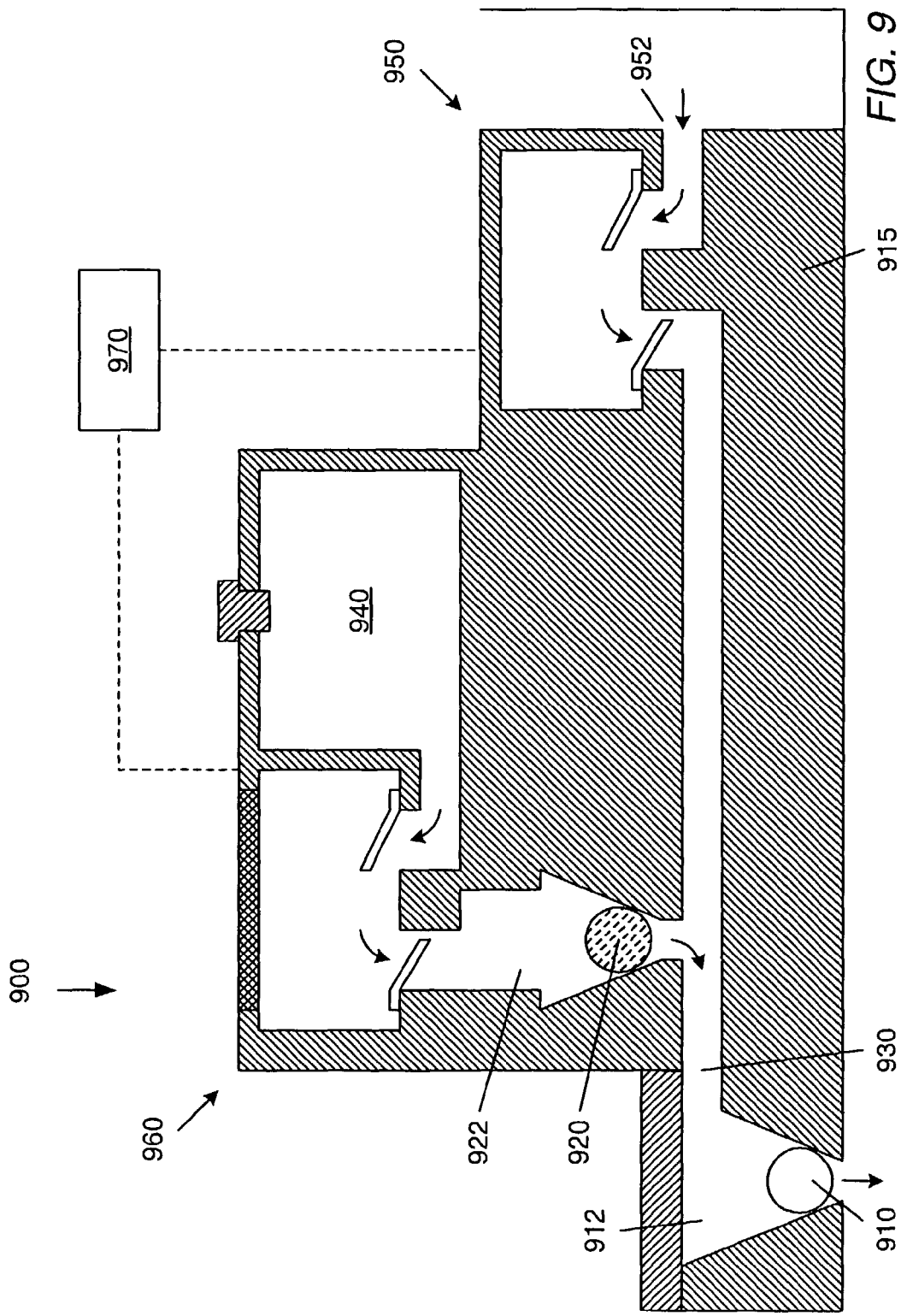
FIG. 9 depicts a cross-sectional view of an embodiment of a sensor array, which includes a system for delivering a reagent from a reagent particle to a sensing cavity.

In some instances, it may be necessary to add a reagent to a particle before, during, or after an analysis process. Reagents may include receptor molecules or indicator molecules. Typically, such reagents are added by passing a fluid stream, which includes the reagent over a sensor array. In an embodiment, the reagent may be incorporated into a sensor array system that includes two particles. In this embodiment, sensor array system 900 may include two particles, 910 and 920, for each sensing position of the sensor array, as depicted in FIG. 9. First particle 910 may be positioned in first cavity 912. Second particle 920 may be positioned in second cavity 922. In one embodiment, the second cavity is coupled to the first cavity via channel 930. The second particle includes a reagent, which is at least partially removable from the particle. The reagent may also be used to modify first particle 910 when in contacted with the first particle, such that the first particle will produce a signal upon interaction with an analyte during use.

The reagent may be added to the first cavity before, during, or after a fluid analysis. The reagent may be coupled to second particle 920. A portion of the reagent coupled to the second particle may be decoupled from the particle by passing a decoupling solution past the particle. The decoupling solution may include a decoupling agent, which will cause at least a portion of the reagent to be at released from the particle. Reservoir 940 may be formed on the sensor array to hold the decoupling solution.

First pump 950 and second pump 960 may be coupled to supporting member 915. First pump 950 may be used to pump fluid from fluid inlet 952 to first cavity 912 via channel 930. Fluid inlet 952 may be located where the fluid, which includes the analyte, is introduced into the sensor array system. Second pump 950 may be coupled to reservoir 940 and second cavity 922. Second pump 960 may be used to transfer the decoupling solution from the reservoir to second cavity 922. The decoupling solution may pass through second cavity 922 and into first cavity 912. Thus, as the reagent is removed, the second particle it may be transferred to first cavity 912 where the reagent may interact with first particle 910. The reservoir may be filled and/or refilled by removing reservoir outlet 942 and adding additional fluid to reservoir 940. While diaphragm based pump systems are depicted in FIG. 9, it should be understood that electrode based pumping systems might also be incorporated into the sensor array to produce fluid flows.

The use of such a system is described by way of example. In some instances, it may be desirable to add a reagent to the first particle prior to passing a fluid to the first particle. The reagent may be coupled to the second particle and placed in the sensor array prior to use. The second particle may be placed in the array during construction of the array. A decoupling solution may be added to the reservoir before use. Controller 970, shown in FIG. 9, may also be coupled to the system to allow automatic operation of the pumps. Controller 970 may initiate the analysis sequence by activating second pump 960, causing the decoupling solution to flow from reservoir 940 to second cavity 922. As the fluid passes through second cavity 922, the decoupling solution may cause at least some of the reagent molecules to be released from second particle 920. The decoupling solution may be passed out of second cavity 922 and into first cavity 912. As the solution passes through the first cavity, some of the reagent molecules may be captured by first particle 910. After a sufficient number of molecules have been captured by first particle 910, flow of fluid thorough second cavity 922 may be stopped by controller 970. During initialization of the system, the flow of fluid through the first pump may be inhibited.

After the system is initialized, the second pump may be stopped and the fluid may be introduced to the first cavity. The first pump may be used to transfer the fluid to the first cavity. The second pump may remain off, thus inhibiting flow of fluid from the reservoir to the first cavity. It should be understood that the reagent solution might be added to the first cavity while the fluid is added to the first cavity. In this embodiment, both the first and second pumps may be operated substantially simultaneously.

Alternatively, the reagent may be added after an analysis. In some instances, a particle may interact with an analyte such that a change in the receptors attached to the first particle occurs. This change, however, may not produce a detectable signal. The reagent attached to the second particle may be used to produce a detectable signal upon interaction with the first particle if a specific analyte is present. In this embodiment, the fluid is introduced into the cavity first. After the analyte has been given, time to react with the particle, the reagent may be added to the first cavity. The interaction of the reagent with the particle may produce a detectable signal. For example, an indicator reagent may react with a particle, which has been exposed to an analyte to produce a color change on the particle. A particle, which has not been exposed to the analyte may remain unchanged or show a different color change.

Figure 10:
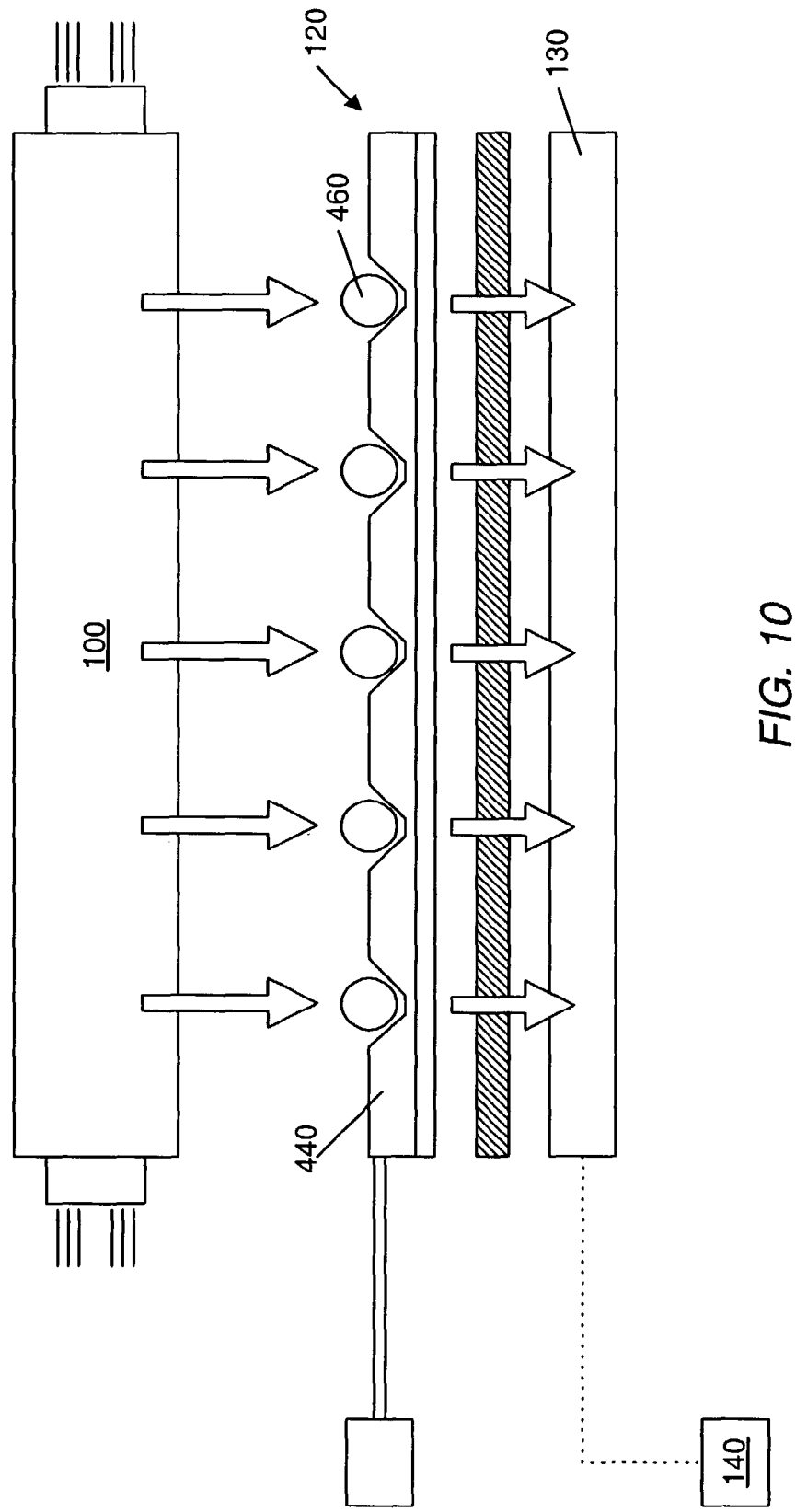
FIG. 10 depicts a schematic of an embodiment of an analyte detection system.

As shown in FIG. 10, a system for detecting analytes in a fluid may include light source 100, sensor array 120, and detector 130. Sensor array 120 may be formed of a supporting member 440 formed to hold a variety of particles 460 in an ordered array. A high sensitivity CCD array may be used to measure changes in optical characteristics, which occur upon binding of the biological/chemical agents. Data acquisition and handling may be performed using existing CCD technology. As described above, calorimetric analysis may be performed using a white light source and a color CCD detector. However, color CCD detectors are typically more expensive than gray scale CCD detectors.

In one embodiment, a gray scale CCD detector may be used to detect calorimetric changes. A gray scale detector may be disposed below a sensor array to measure the intensity of light being transmitted through the sensor array. A series of lights (e.g., light emitting diodes) may be arranged above the sensor array. In one embodiment, groups of three LED lights may be arranged above each of the cavities of the array. Each of these groups of LED lights may include a red, blue, and green light. Each of the lights may be operated individually such that one of the lights may be on while the other two lights are off. In order to provide color information while using a gray scale detector, each of the lights is sequentially turned on and the gray scale detector is used to measure the intensity of the light passing through the sensor array. After information from each of the lights is collected, the information may be processed to derive the absorption changes of the particle.

In one embodiment, data collected by the gray scale detector may be recorded using 8 bits of data. Thus, the data will appear as a value between 0 and 255. The color of each chemical sensitive element may be represented as a red, blue, and green value. For example, a blank particle (i.e., a particle which does not include a receptor) will typically appear white. When each of the LED lights (red, blue, and green) is operated, the CCD detector will record a value corresponding to the amount of light transmitted through the cavity. The intensity of the light may be compared to a blank particle to determine the absorbance of a particle with respect to the LED light used. Thus, the red, green, and blue components may be recorded individually without the use of a color CCD detector.

In one embodiment, it is found that a blank particle exhibits an absorbance of about 253 when illuminated with a red LED, a value of about 250 when illuminated by a green LED, and a value of about 222 when illuminated with a blue LED. This signifies that a blank particle does not significantly absorb red, green, or blue light. When a particle with a receptor is scanned, the particle may exhibit a color change due to absorbance by the receptor. For example, when a particle including a 5-carboxyfluorescein receptor is subjected to white light, the particle shows a strong absorbance of blue light. When a red LED is used to illuminate the particle, the gray scale CCD detector may detect a value of about 254. When the green LED is used, the gray scale detector may detect a value of about 218. When a blue LED light is used, a gray scale detector may detect a value of about 57. The decrease in transmittance of blue light is believed to be due to the absorbance of blue light by the 5-carboxyfluorescein. In this manner, the color changes of a particle may be quantitatively characterized using a gray scale detector.

As described above, after the cavities are formed in the supporting member, a particle may be positioned at the bottom of a cavity are described in U.S. patent applications Ser. Nos.: 09/287,248; 09/354,882; 09/775,340; 09/775,344; 09/775,353; 09/775,048; 09/775,343; 10/072,800 which are incorporated by reference as if fully set forth herein. This allows the location of a particular particle to be precisely controlled during the production of the array.

One challenge in a chemical sensor system is keeping "dead volume" to a minimum. This is especially problematic when an interface to the outside world is required (e.g., a tubing connection). In many cases, the "dead volume" associated with delivery of a sample to the reaction site in a "lab-on-a-chip" may far exceed the actual amount of reagent required for the reaction. Filtration is also frequently necessary to prevent small flow channels in the sensor arrays from plugging. Here the filter can be made an integral part of the sensor package.

Figure 11:
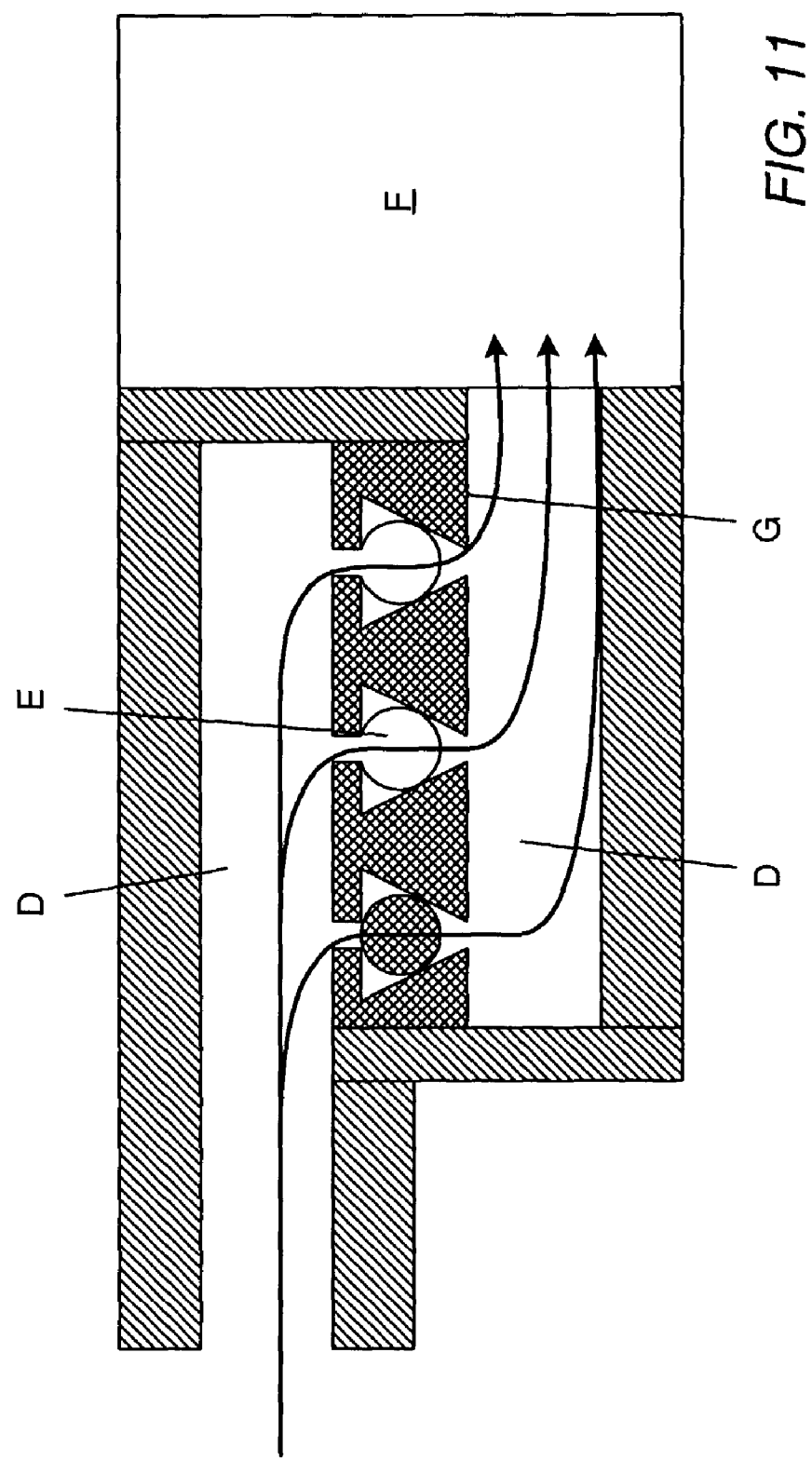
FIG. 11 depicts a cross-sectional view of an embodiment of a sensor array, which includes a vacuum chamber.

In an embodiment, a system for detecting an analyte in a fluid includes a conduit coupled to a sensor array, and a vacuum chamber coupled to the conduit. FIG. 11 depicts a system in which fluid stream E passes through conduit D, onto sensor array G, and into vacuum apparatus F. Vacuum apparatus F may be coupled to conduit D downstream from sensor array G. A vacuum apparatus is herein defined to be any system capable of creating or maintaining a volume at a pressure below atmospheric. An example of a vacuum apparatus is a vacuum chamber. A vacuum chamber, in one embodiment, may include sealed tubes from which a portion of air has been evacuated to create a vacuum within the tube. A commonly used example of such a sealed tube is a "vacutainer" system commercially available from Becton Dickinson. Alternatively, a vacuum chamber sealed by a movable piston may also be used to generate a vacuum. For example, a syringe may be coupled to the conduit. Movement of the piston (i.e., the plunger) away from the chamber will create a partial vacuum within the chamber. Alternatively, the vacuum apparatus may be a vacuum pump or vacuum line. Vacuum pumps may include direct drive pumps, oil pumps, aspirator pumps, or micropumps. Micropumps that may be incorporated into a sensor array system have been previously described.

Figure 12:
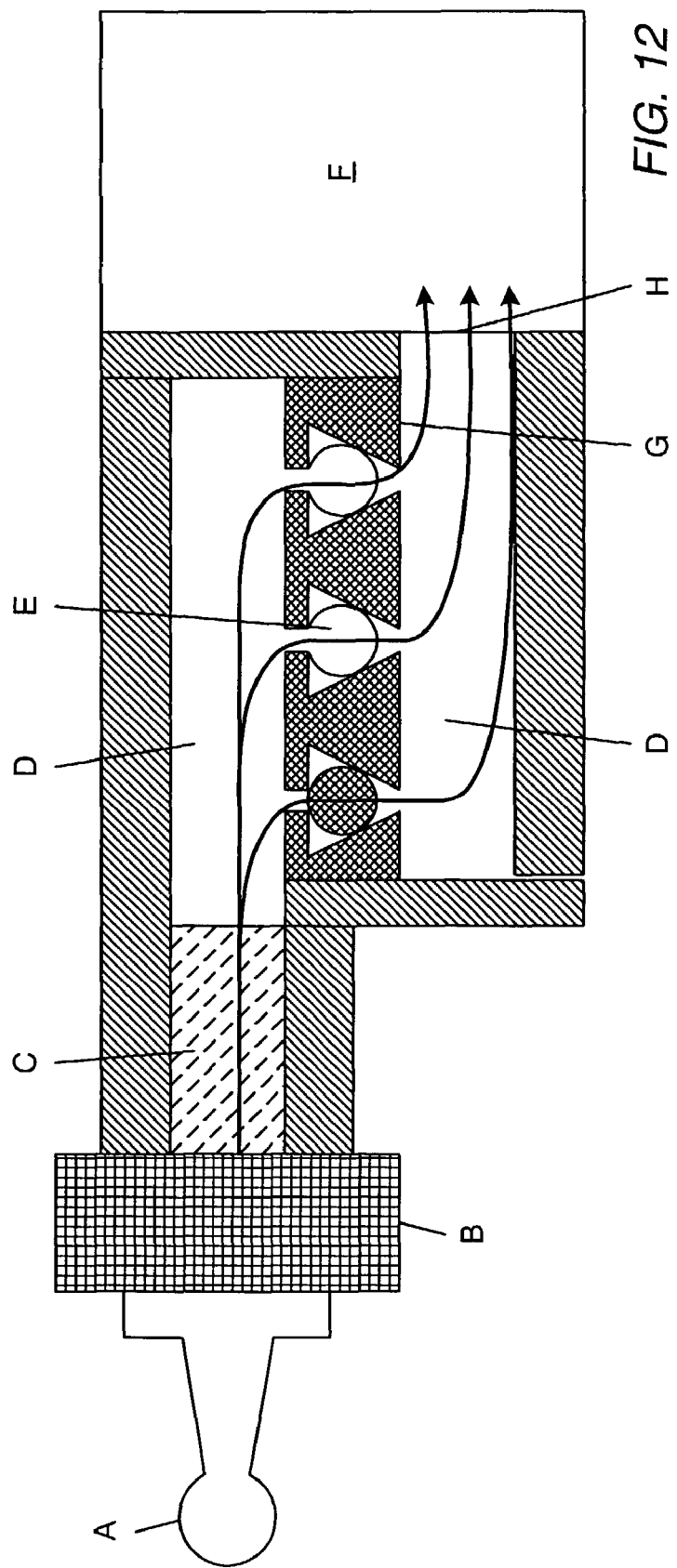
FIG. 12 depicts a cross-sectional view of an embodiment of a sensor array, which includes a vacuum chamber, a filter, and a reagent reservoir.

As opposed to previously described methods, in which a pump is used to force a fluid stream through a sensor array, the use of a vacuum apparatus allows the fluid to be pulled through the sensor array. Referring to FIG. 12, vacuum apparatus F is coupled downstream from sensor array G. When coupled to the conduit D, the vacuum apparatus may exert a suction force on a fluid stream, forcing a portion of the stream to pass over, and in some instances, through, sensor array G. In some embodiments, the fluid may continue to pass through conduit D after passing sensor array G, and into vacuum apparatus F.

In an embodiment where the vacuum apparatus is a pre-evacuated tube, the fluid flow will continue until the air within the tube is at a pressure substantially equivalent to atmospheric pressure. The vacuum apparatus may include penetrable wall H. Penetrable wall H forms a seal inhibiting air from entering vacuum apparatus F. When wall H is broken or punctured, air from outside the system will begin to enter the vacuum apparatus. In one embodiment, conduit D includes a penetrating member (e.g., a syringe needle), which allows the penetrable wall to be pierced. Piercing penetrable wall H causes air and fluid inside the conduit to be pulled through the conduit and into the vacuum apparatus until the pressure between vacuum apparatus F and conduit D is equalized.

The sensor array system may also include filter B coupled to conduit D, as depicted in FIG. 12. The filter B may be positioned along conduit D, upstream from sensor array G. Filter B may be a porous filter, which includes a membrane for removing components from the fluid stream. In one embodiment, filter B may include a membrane for removal of particulates above a minimum size. The size of the particulates removed will depend on the porosity of the membrane as is known in the art. Alternatively, the filter may be used to remove unwanted components of a fluid stream. For example, if a fluid stream is a blood sample, the filter may be used to remove red and white blood cells from the stream, leaving plasma and other components in the stream.

The sensor array may also include reagent delivery reservoir C. Reagent delivery reservoir C may be coupled to conduit D upstream from sensor array G. Reagent delivery reservoir C may be formed from a porous material, which includes a reagent of interest. As the fluid passes through this reservoir, a portion of the reagent within the regent delivery reservoir passes into the fluid stream. The fluid reservoir may include a porous polymer or filter paper on which the reagent is stored. Examples of reagents which may be stored within the reagent delivery reservoir include, but are not limited to, visualization agents (e.g., dye or fluorophores), co-factors, buffers, acids, bases, oxidants, and reductants.

The sensor array may also include fluid sampling device A coupled to conduit D. Fluid sampling device A may be used to transfer a fluid sample from outside sensor array G to conduit D. A number of fluid sampling devices may be used, including, but not limited to, a syringe needle, a tubing connector, a capillary tube, or a syringe adapter.

The sensor array may also include a micropump or a microvalve system coupled to the conduit to further aid in transfer of fluid through the conduit. Micropumps and valves are described in U.S. patent application Ser. No. 10/072,800, which is fully incorporated herein. In one embodiment, a microvalve or micropump may be used to keep a fluid sample or a reagent solution separated from the sensor array. Typically, these microvalves and micropumps include a thin flexible diaphragm. The diaphragm may be moved to an open position, in one embodiment, by applying a vacuum to the outside of the diaphragm. In this way, a vacuum apparatus coupled to the sensor array may be used to open a remote microvalve or pump.

In another embodiment, a microvalve may be used to control the application of a vacuum to a system. For example, a microvalve may be positioned adjacent to a vacuum apparatus. The activation of the microvalve may allow the vacuum apparatus to communicate with a conduit or sensor array. The microvalve may be remotely activated at controlled times and for controlled intervals.

A sensor array system, such as depicted in FIG. 12, may be used for analysis of blood samples. A micropuncture device A may be used to extract a small amount of blood from a patient, e.g., through a finger-prick. The blood may be drawn through a porous filter that serves to remove undesirable particulate matter. For the analysis of antibodies or antigens in whole blood, a filtering agent may be chosen to remove both white and red blood cells while leaving in the fluid stream blood plasma and all of the components therein. Methods of filtering blood cells from whole blood are taught, for example, in U.S. Pat. Nos. 5,914,042, 5,876,605, and 5,211,850, which are incorporated by reference. The filtered blood may also be passed through a reagent delivery reservoir including a porous layer impregnated with the reagent(s) of interest. In many cases, a visualization agent will be included in this layer so that the presence of the analytes of interest can be resolved. The treated fluid may be passed above an electronic tongue chip through a capillary layer, down through the various sensing particles, and through the chip onto a bottom capillary layer. After exiting a central region, the excess fluid flows into the vacuum apparatus. This excess fluid may serve as a source of samples for future measurements. A "hard copy" of the sample is thus created to back up electronic data recorded for the specimen.

Other examples of procedures for testing bodily fluids are described in the following U.S. Pat. Nos.: 4,596,657; 4,189,382; 4,115,277; 3,954,623; 4,753,776; 4,623,461; 4,069,017; 5,053,197; 5,503,985; 3,696,932; 3,701,433; 4,036,946; 5,858,804; 4,050,898; 4,477,575; 4,810,378; 5,147,606; 4,246,107; and 4,997,577, all of which are incorporated by reference.

The generally described sampling method may also be used for either antibody or antigen testing of bodily fluids. A general scheme for testing antibodies is depicted in FIG. 13. FIG. 13A depicts a polymer bead having a protein coating that can be recognized in a specific manner by a complimentary antibody. Three antibodies (shown within the dashed rectangle) are shown to be present in a fluid phase that bathes the polymer bead. Turning to FIG. 13B, the complimentary antibody binds to the bead while the other two antibodies remain in the fluid phase. A large increase in the complimentary antibody concentration is noted at this bead. In FIG. 13C, a visualization agent such as a protein (shown within the dashed rectangle) is added to the fluid phase. The visualization agent is chosen because either it possesses a strong absorbance property or it exhibits fluorescence characteristics that can be used to identify the species of interest via optical measurements. The protein is an example of a reagent that associates with a common region of most antibodies. Chemical derivatization of visualization agent with dyes, quantum particles, or fluorophores, is used to evoke desired optical characteristics. After binding to the bead-localized antibodies, as depicted in FIG. 13D, the visualization agent reveals the presence of complimentary antibodies at specific polymer bead sites.

FIG. 14 depicts another general scheme for the detection of antibodies, which uses a sensor array composed of four individual beads. Each of the four beads is coated with a different antigen (e.g., a protein coating). As depicted in FIG. 14A, the beads are washed with a fluid sample, which includes four antibodies. Each of the four antibodies binds to its complimentary antigen coating, as depicted in FIG. 14B. A visualization agent may be introduced into the chamber, as depicted in FIG. 14C. The visualization agent, in one embodiment, may bind to the antibodies, as depicted in FIG. 14D. The presence of the labeled antibodies is assayed by optical means (e.g., absorbance, reflectance, and/or fluorescence). Because the location of the antigen coatings is known ahead of time, the chemical/biochemical composition of the fluid phase can be determined from the pattern of optical signals recorded at each site.

In an alternative methodology, not depicted, the antibodies in the sample may be exposed to the visualization agent prior to their introduction into the chip array. This may render the visualization step depicted in FIG. 14C unnecessary.

Figure 15:
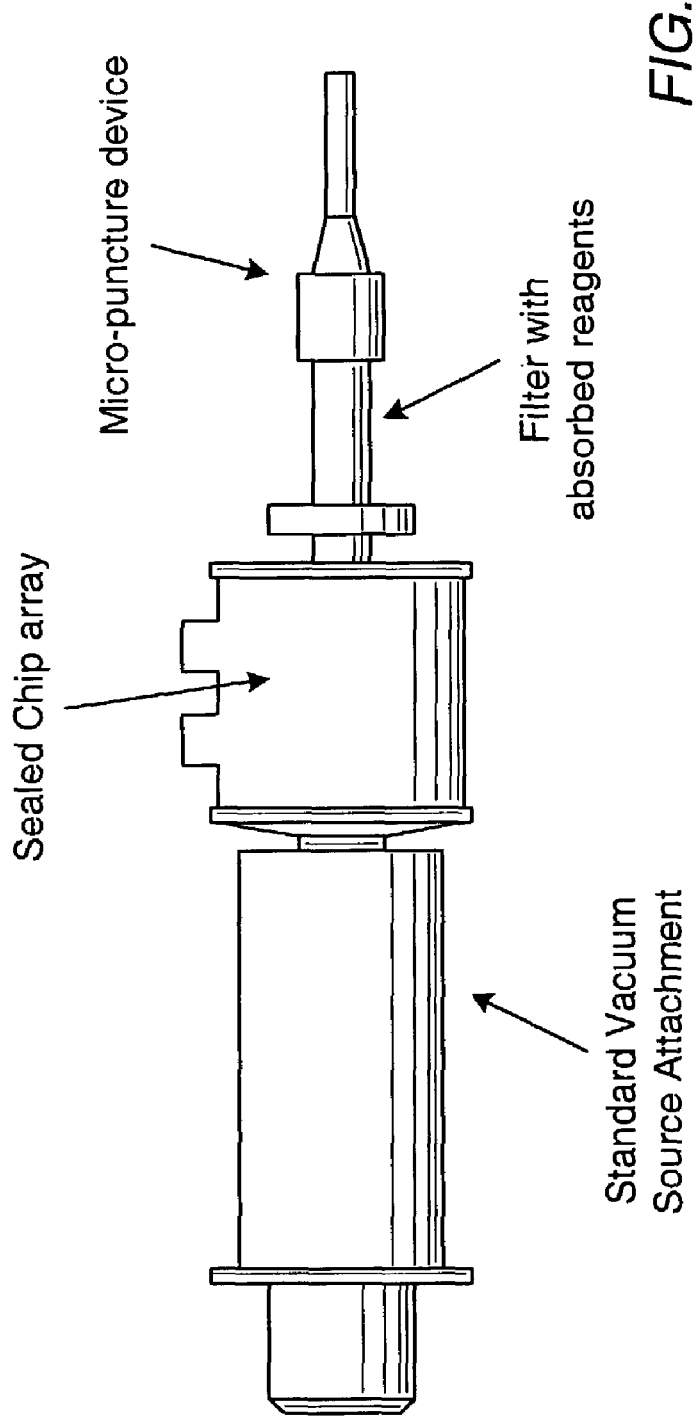
FIG. 15 depicts an of an embodiment of a sensor array which includes a vacuum chamber, a sensor array chamber, and a sampling device.

FIG. 15 depicts a system for detecting an analyte in a fluid stream. The system includes a vacuum apparatus, a chamber in which a sensor array may be disposed, and an inlet system for introducing the sample into the chamber. In this embodiment, the inlet system is depicted as a micro-puncture device. The chamber holding the sensor array may be a Sikes-Moore chamber, as previously described. The vacuum apparatus is a standard "vacutainer" type vacuum tube. The micro puncture device includes a Luer-lock attachment, which can receive a syringe needle. Between the micro-puncture device and the chamber, a syringe filter may be placed to filter the sample as the sample enters the chamber. Alternatively, a reagent may be placed within the filter. The reagent may be carried into the chamber via the fluid as the fluid passes through the filter.

Figure 16:
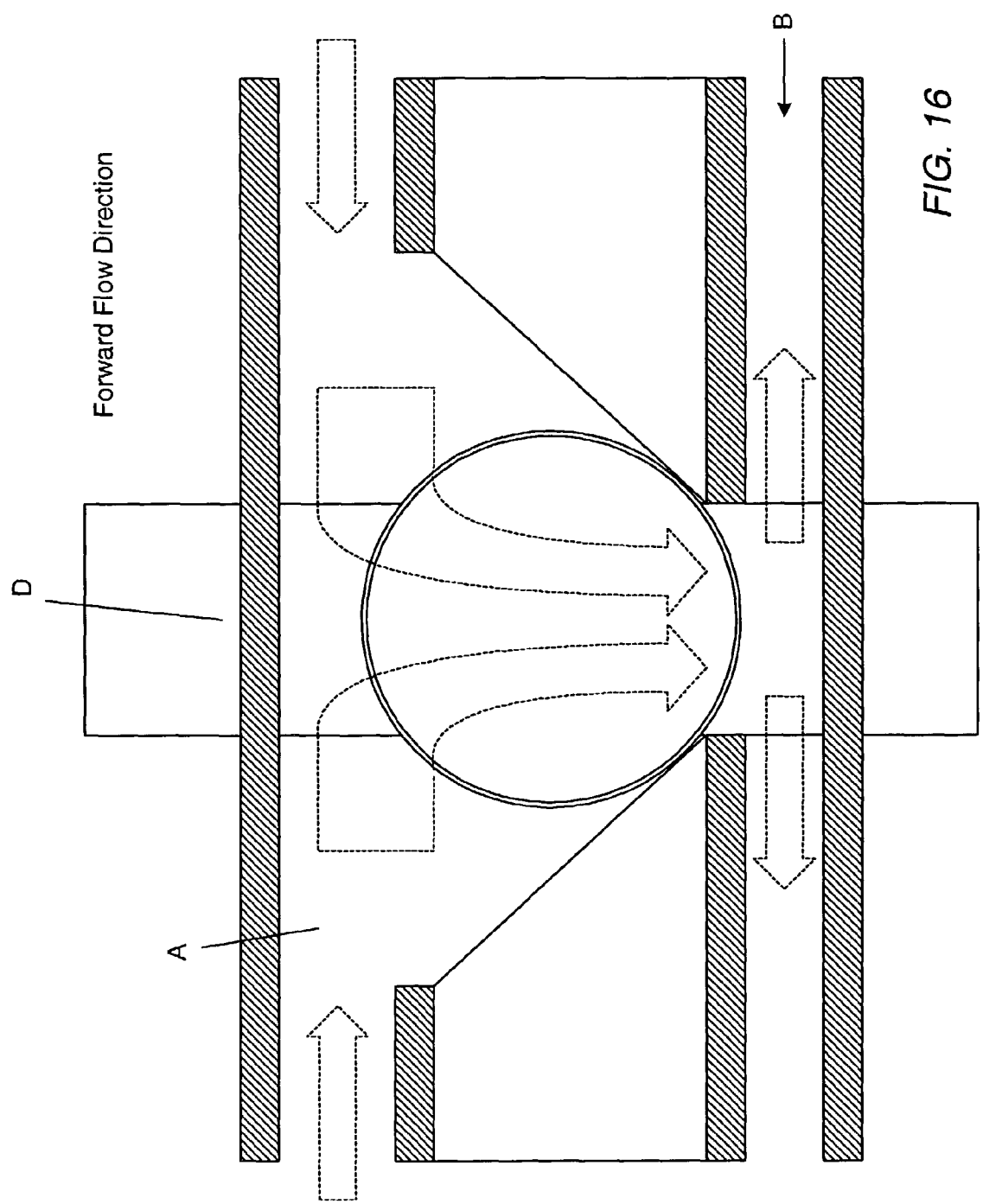
FIG. 16 depicts a flow path of a fluid stream through a sensor array from the top toward the bottom of the sensor array in an embodiment of a sensor array system.

As has been previously described, a sensor array may allow a fluid sample to pass through a sensor array during use. Fluid delivery to the sensor array may be accomplished by having the fluid enter the top of the chip through capillary A, as depicted in FIG. 16. The fluid traverses the chip and exits from bottom capillary B. Between the top and bottom capillaries, the fluid passes by the particle. The fluid, containing analytes, has an opportunity to encounter receptor sites of the particle. The presence of analytes may be identified using optical means as previously mentioned. Fluid flow in a forward direction forces the particle towards the bottom of the cavity. Under these circumstances, the particle is placed for ideal optical measurements, in view of light pathway D.

Figure 17:
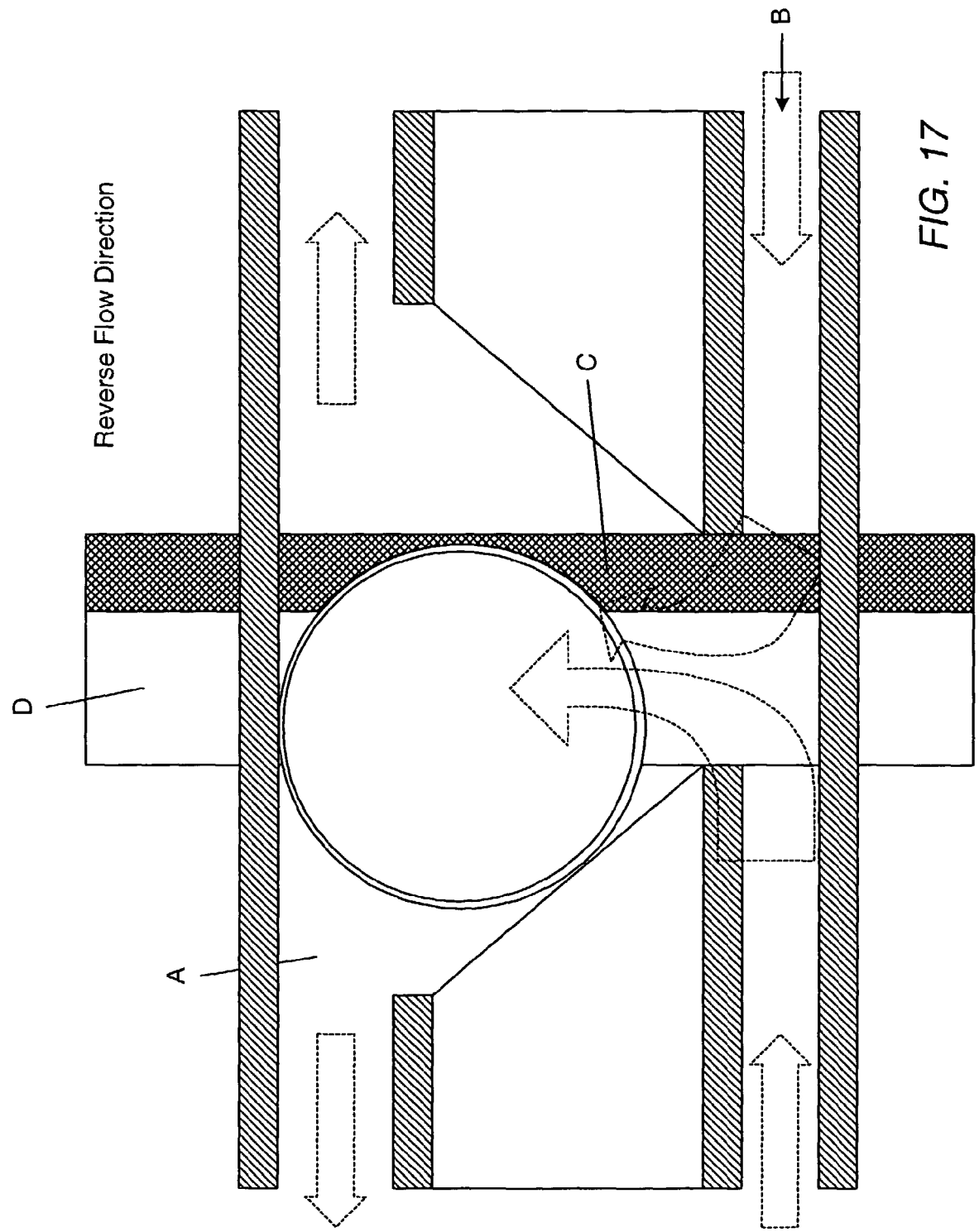
FIG. 17 depicts a flow path of a fluid stream through a sensor array from the bottom toward the top of the sensor array in an embodiment of a sensor array system.

In another embodiment, fluid flow may go from the bottom of the sensor array toward the top of the sensor array, as depicted in FIG. 17. In a reverse flow direction, the fluid exits the top of the chip through capillary A. The fluid flow traverses the chip and enters the cavity from the bottom capillary B. Between the top and bottom capillaries, the fluid may avoid at least a portion of the particle by taking indirect pathway C. The presence of analytes may be identified using optical means as before. Unfortunately, only a portion of the light may pass through the particle. In the reverse flow direction, the particle may be partially removed from the path of an analysis light beam D by an upward pressure of the fluid, as shown in FIG. 17. Under these circumstances, some of the light may traverse the chip by path E and enter a detector without passing through the sensor particle.

In any microfluidic chemical sensing system, there may be a need to store chemically sensitive elements in an inert environment. The particles may be at least partially surrounded by an inert fluid, such as an inert, non-reactive gas, a non-reactive solvent, or a liquid buffer solution. Alternatively, the particles may be maintained under a vacuum. Before exposure of the particles to an analyte, the inert environment may need to be removed to allow proper testing of a sample of containing the analyte. In one embodiment, a system may include a fluid transfer system for the removal of an inert fluid prior to introduction of the sample with minimum dead volume.

In one embodiment, a pumping system may be used to pull the inert fluid through the array from one side of the array. The pumping system may provide pumping action downstream from the array. The inert fluid may be efficiently removed while the beads remain within the sensor array. Additionally, the analyte sample may be drawn toward the sensor array as the inert fluid is being removed from the sensor array. A pocket of air may separate the analyte sample from the inert fluid as the sample moves through the array. Alternatively, the sample may be pumped from an upstream micropump. A vacuum downstream may produce a maximum of about one atmosphere of head pressure, while an upstream pump may produce an arbitrarily high head pressure. This can affect fluid transport rates through the system. For small volume microfluidic systems, even with low flow coefficients, one atmosphere of head pressure may provide acceptable transfer rates for many applications.

In another embodiment, a vacuum apparatus may be formed directly into a micromachined array. The vacuum apparatus may transmit fluid to and from a single cavity or a plurality of cavities. In an alternate embodiment, a separate vacuum apparatus may be coupled to each of the cavities.

Manufacturing Methods for a Sensor Array

After the cavities are formed in the supporting member, a particle may be positioned at the bottom of a cavity using a micromanipulator. This allows the location of a particular particle to be precisely controlled during the production of the array. The use of a micromanipulator may be impractical for mass-production of sensor arrays. A number of methods for inserting particles that may be amenable to an industrial application have been devised. Examples of micromanipulators and dispense heads are described in U.S. patent application Ser. No. 10/072,800 which is fully incorporated as set forth herein.

In one embodiment, the use of a micromanipulator may be automated. Particles may be "picked and placed" using a robotic automated assembly. The robotic assembly may include one or more dispense heads. A dispense head may pick up and hold a particle. Alternatively, a dispense head may hold a plurality of particles and dispense only a portion of the held particles. An advantage of using a dispense head is that individual particles or small groups of particles may be placed at precise locations on the sensor array. A variety of different types of dispense heads may be used.

Portable Sensor Array System

A sensor array system becomes most powerful when the associated instrumentation may be delivered and utilized at the application site. That is, rather than remotely collecting the samples and bringing them to a centrally based analysis site; it may be advantageous to be able to conduct the analysis at the testing location. Such a system may be used, for example, for point of care medicine, on site monitoring of process control applications, military intelligence gathering devices, environmental monitoring, and food safety testing.

Figure 18:
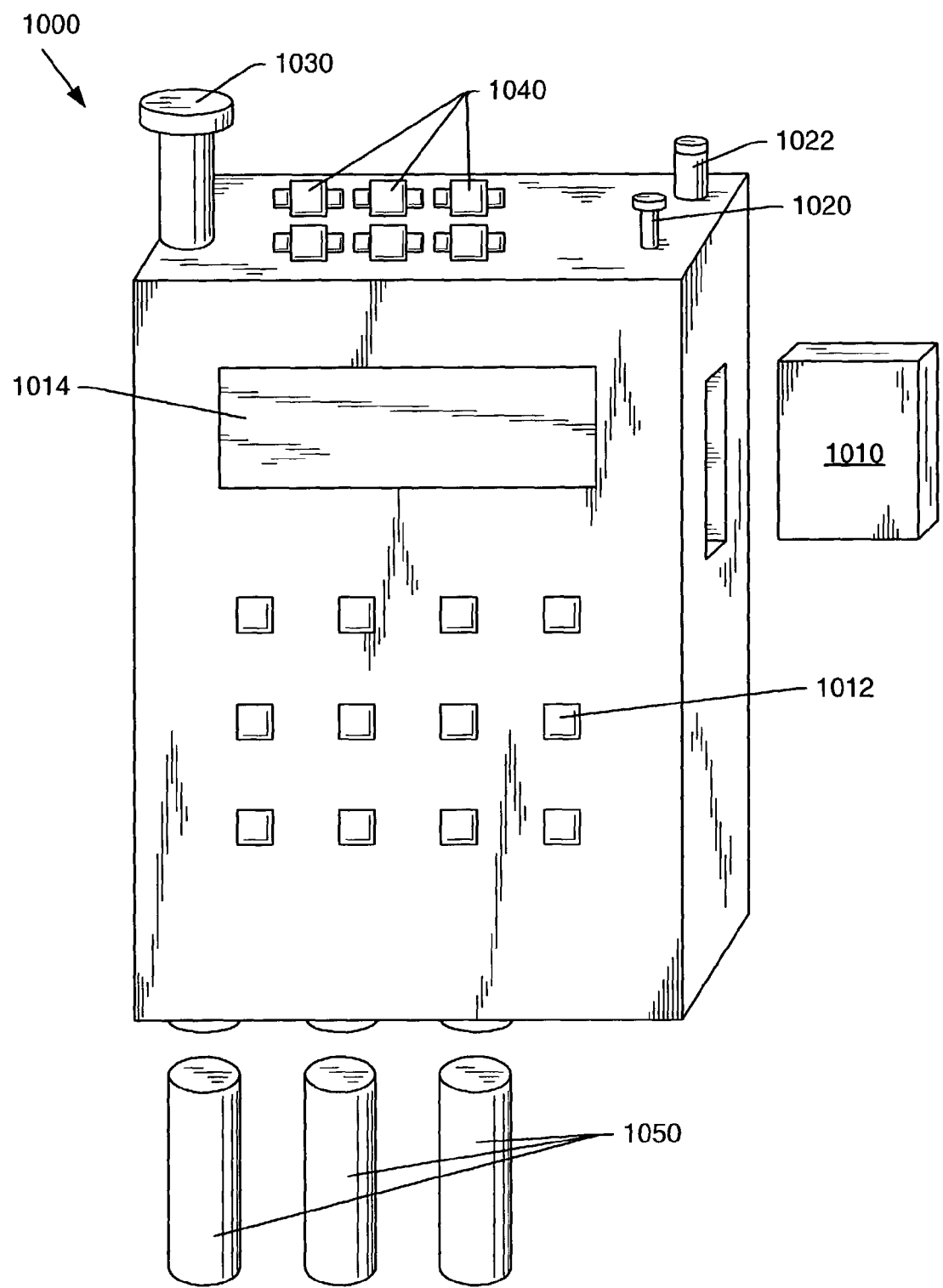
FIG. 18 depicts an embodiment of a portable sensor array system.

An embodiment of a portable sensor array system is depicted in FIG. 18. The portable sensor array system would have, in one embodiment, a size and weight that would allow the device to be easily carried by a person to a testing site. The portable sensor array system includes a light source, a sensor array, and a detector. The sensor array, in some embodiments, is formed on a supporting member to hold a variety of particles in an ordered array. The particles are, in some embodiments, elements that create a detectable signal in the presence of an analyte. The particles may include a receptor molecule coupled to a polymeric bead. The receptors may be chosen for interacting with specific analytes. This interaction may take the form of a binding/association of the receptors with the analytes. The supporting member may be made of any material capable of supporting the particles. The supporting member may include a plurality of cavities. The cavities may be formed such that at least one particle is substantially contained within the cavity. The sensor array has been previously described in detail.

The portable sensor array system may be used for a variety of different testing. The flexibility of sensor array system 1000, with respect to the types of testing, may be achieved using a sensor array cartridge. Turning to FIG. 18, sensor array cartridge 1010 may be inserted into portable sensor array system 1000 prior to testing. The type of sensor array cartridge used will depend on the type of testing to be performed. Each cartridge will include a sensor array, which includes a plurality of chemically sensitive particles, each of the particles including receptors specific for the desired test. For example, a sensor array cartridge for use in medical testing for diabetes may include a number of particles that are sensitive to sugars. A sensor array for use in water testing, however, would include different particles, for example, particles specific for pH and/or metal ions.

The sensor array cartridge may be held in place in a manner analogous to a floppy disk of a computer. The sensor array cartridge may be inserted until it snaps into a holder disposed within the portable sensor system. The holder may inhibit the cartridge from falling out from the portable sensor system and place the sensor in an appropriate position to receive the fluid samples. The holder may also align the sensor array cartridge with the light source and the detector. A release mechanism may be incorporated into the holder that allows the cartridge to be released and ejected from the holder. Alternatively, the portable sensor array system may incorporate a mechanical system for automatically receiving and ejecting the cartridge in a manner analogous to a CD-ROM type system.

The analysis of simple analyte species like acids/bases, salts, metals, anions, hydrocarbon fuels, and solvents may be repeated using highly reversible receptors. Chemical testing of these species may be repeatedly accomplished with the same sensor array cartridge. In some cases, the cartridge may require a flush with a cleaning solution to remove traces from a previous test. Thus, replacement of cartridges for environmental usage may be required on an occasional basis (e.g., daily, weekly, or monthly) depending on the analyte and the frequency of testing.

Alternatively, the sensor array may include highly specific receptors. Such receptors are particularly useful for medical testing, and testing for chemical and biological warfare agents. Once a positive signal is recorded with these sensor arrays, the sensor array cartridge may need to be replaced immediately. The use of a sensor array cartridge makes this replacement easy.

Fluid samples may be introduced into the system at ports 1020 and 1022 at the top of the unit. Two ports are shown, although more ports may be present. Port 1022 may be for the introduction of liquids found in the environment and some bodily fluids (e.g., water, saliva, urine, etc.). Port 1020 may be used for the delivery of human whole blood samples. The delivery of blood may be accomplished by the use of a pinprick to pierce the skin and a capillary tube to collect the blood sample. Port 1020 may accept either capillary tubes or syringes that include blood samples.

For the collection of environmental samples, syringe 1030 may be used to collect the samples and transfer the samples to the input ports. The portable sensor array system may include a holder that allows the syringe to be coupled to the side of the portable sensor array system. Ports 1020 may include a standard Luer lock adapter (either male or female) to allow samples collected by syringe to be directly introduced into the portable sensor array system from the syringe.

The input ports may also be used to introduce samples in a continuous manner. The introduction of samples in a continuous manner may be used, e.g., to evaluate water streams. An external pump may be used to introduce samples into the portable sensor array system in a continuous manner. Alternatively, internal pumps disposed within the portable sensor array system may be activated to pull a continuous stream of the fluid sample into the portable sensor array system. The ports may allow introduction of gaseous samples.

In some cases, it may be necessary to filter a sample prior to its introduction into the portable sensor array system. For example, environmental samples may be filtered to remove solid particles prior to their introduction into the portable sensor array system. Commercially available nucleopore filters 1040 anchored at the top of the unit may be used for this purpose. In one embodiment, filters 1040 may have Luer lock connections (either male or female) on both sides allowing them to be connected directly to an input port and a syringe.

In one embodiment, all of the necessary fluids required for the chemical/biochemical analyses are contained within the portable sensor array system. The fluids may be stored in one or more cartridges 1050. Cartridges 1050 may be removable from the portable sensor array system. Thus, when cartridge 1050 is emptied of fluid, the cartridge may be replaced by a new cartridge or removed and refilled with fluid. Cartridges 1050 may also be removed and replaced with cartridges filled with different fluids when the sensor array cartridge is changed. Thus, the fluids may be customized for the specific tests being run. Fluid cartridges may be removable or may be formed as an integral part of the reader.

Fluid cartridges 1050 may include a variety of fluids for the analysis of samples. In one embodiment, each cartridge may include up to about 5 mL of fluid and may deleted after about 100 tests. One or more cartridges 1050 may include a cleaning solution. The cleaning solution may be used to wash and/or recharge the sensor array prior to a new test. In one embodiment, the cleaning solution may be a buffer solution. Another cartridge 1050 may include visualization agents.

Visualization agents may be used to create a detectable signal from the particles of the sensor array after the particles interact with the fluid sample. In one embodiment, visualization agents include dyes (visible or fluorescent) or molecules coupled to a dye, which interact with the particles to create a detectable signal. In an embodiment, cartridge 1050 may be a vacuum reservoir. The vacuum reservoir may be used to draw fluids into the sensor array cartridge. The vacuum cartridge would act in an analogous manner to the vacutainer cartridges described previously. In another embodiment, a fluid cartridge may be used to collect fluid samples after they pass through the sensor array. The collected fluid samples may be disposed of in an appropriate manner after the testing is completed.

In one embodiment, alphanumeric display screen 1014 may be used to provide information relevant to the chemistry/biochemistry of the environment or blood samples. Also included within the portable sensor array system may be a data communication system. Such systems include data communication equipment for the transfer of numerical data, video data, and/or sound data. Transfer may be accomplished using either digital or analog standards. The data may be transmitted using any transmission medium such as electrical wire, infrared, RF, and/or fiber optic. In one embodiment, the data transfer system may include a wireless link that may be used to transfer the digital chemistry/biochemistry data to a closely positioned communications package. In another embodiment, the data transfer system may include a floppy disk drive for recording the data and allowing the data to be transferred to a computer system. In another embodiment, the data transfer system may include serial or parallel port connection hardware to allow transfer of data to a computer system.

The portable sensor array system may also include a global positioning system ("GPS"). The GPS may be used to track the area from which a sample is collected. After collecting sample data, the data may be fed to a server, which compiles the data along with GPS information. Subsequent analysis of this information may be used to generate a chemical/biochemical profile of an area. For example, tests of standing water sources in a large area may be used to determine the environmental distribution of pesticides or industrial pollutants.

Other devices may also be included in the portable sensor array that is specific for other applications. For example, medical monitoring devices may include, but is not limited to, EKG monitors, blood pressure devices, pulse monitors, and temperature monitors.

The detection system may be implemented in a number of different ways such that all of the detection components fit within the casing of the portable sensor array system. For an optical detection/imaging device, either CMOS or CCD focal plane arrays may be used. The CMOS detector offers some advantages in terms of lower cost and power consumption, while the CCD detector offers the highest possible sensitivity. Depending on the illumination system, either monochrome or color detectors may be used. A one-to-one transfer lens may be employed to project the image of a bead sensor array onto the focal plane of the detector. All fluidic components may be sealed from contact with any optical or electronic components. Sealing the fluids from the detectors avoids complications that may arise from contamination or corrosion in systems that require direct exposure of electronic components to the fluids under test. Other detectors such as photodiodes, cameras, integrated detectors, photoelectric cells, interferometers, and photomultiplier tubes may be used.

The illumination system for colorimetric detection may be constructed in several manners. When using a monochrome focal plane array, a multi-color, but "discrete-wavelength-in-time" illumination system may be used. The simplest implementation may include several LED's (light emitting diodes) each operating at a different wavelength. Red, green, yellow, and blue wavelength LEDs is now commercially available for this purpose. By switching from one LED to the next, and collecting an image associated with each, colorimetric data may be collected.

It is also possible to use a color focal plane detector array. A color focal plane detector may allow the determination of colorimetric information after signal acquisition using image processing methods. In this case, a "white light" illuminator is used as the light source. "White light" LEDs may be used as the light source for a color focal plane detector. White light LEDs use a blue LED coated with a phosphor to produce a broadband optical source. The emission spectrum of such devices may be suitable for colorimetric data acquisition. A plurality of LEDs may be used. Alternatively, a single LED may be used.

Other light sources that may be useful include electroluminescent sources, fluorescent light sources, incandescent light sources, laser lights sources, laser diodes, arc lamps, and discharge lamps. The system may also use an external light source (both natural and unnatural) for illumination.

A lens may be positioned in front of the light source to allow the illumination area of the light source to be expanded. The lens may also allow the intensity of light reaching the sensor array to be controlled. For example, the illumination of the sensor array may be made uniform by the use of a lens. In one example, a single LED light may be used to illuminate the sensor array. Examples of lenses that may be used in conjunction with an LED include Diffusing plate PN K43-717 Lens JML, PN61874 from Edmund scientific.

In addition to colorimetric signaling, chemical sensitizers may be used that produce a fluorescent response. The detection system may still be either monochrome (for the case where the specific fluorescence spectrum is not of interest, just the presence of a fluorescence signal) or color-based (that would allow analysis of the actual fluorescence spectrum). An appropriate excitation notch filter (in one embodiment, a long wavelength pass filter) may be placed in front of the detector array. The use of a fluorescent detection system may require an ultraviolet light source. Short wavelength LEDs (e.g., blue to near UV) may be used as the illumination system for a fluorescent-based detection system.

In some embodiments, use of a light source may not be necessary. The particles may rely on the use of chemiluminescence, thermoluminescence or piezoluminescence to provide a signal. In the presence of an analyte of interest, the particle may be activated such that the particles produce light. In the absence of an analyte, the particles may produce minimal or no light.

The portable sensor array system may also include an electronic controller, which controls the operation of the portable sensor array system. The electronic controller may also be capable of analyzing the data and determining the identity of the analytes present in a sample. While the electronic controller is described herein for use with the portable sensor array system, it should be understood that the electronic controller might be used with any of the previously described embodiments of an analyte detection system.

The controller may be used to control the various operations of the portable sensor array. Some of the operations that may be controlled or measured by the controller include: (i) determining the type of sensor array present in the portable sensor array system; (ii) determining the type of light required for the analysis based on the sensor array; (iii) determining the type of fluids required for the analysis, based on the sensor array present; (iv) collecting the data produced during the analysis of the fluid sample; (v) analyzing the data produced during the analysis of the fluid sample; (vi) producing a list of the components present in the inputted fluid sample; and, (vii) monitoring sampling conditions (e.g., temperature, time, density of fluid, turbidity analysis, lipemia, bilirubinemia, etc).

Additionally, the controller may provide system diagnostics and information to the operator of the apparatus. The controller may notify the user when routine maintenance is due or when a system error is detected. The controller may also manage an interlock system for safety and energy conservation purposes. For example, the controller may prevent the lamps from operating when the sensor array cartridge is not present.

The controller may also interact with an operator. The controller may include input device 1012 and display screen 1014, as depicted in FIG. 18. A number of operations controlled by the controller, as described above, may be dependent on the input of the operator. The controller may prepare a sequence of instructions based on the type of analysis to be performed. The controller may send messages to the output screen to let the used know when to introduce samples for the test and when the analysis is complete. The controller may display the results of any analysis performed on the collected data on the output screen.

Many of the testing parameters may be dependent upon the type of sensor array used and the type of sample being collected. The controller will require, in some embodiments, the identity of the sensor array and test being performed in order to set up the appropriate analysis conditions. Information concerning the sample and the sensor array may be collected in a number of manners.

In one embodiment, the sample and sensor array data may be directly inputted by the user to the controller. Alternatively, the portable sensor array may include a reading device, which determines the type of sensor cartridge being used once the cartridge is inserted. In one embodiment, the reading device may be a bar code reader capable of reading a bar code placed on the sensor array. In this manner, the controller can determine the identity of the sensor array without any input from the user. In another embodiment, the reading device may be mechanical in nature. Protrusions or indentation formed on the surface of the sensor array cartridge may act as a code for a mechanical reading device. The information collected by the mechanical reading device may be used to identify the sensor array cartridge. Other devices may be used to accomplish the same function as the bar code reader. These devices include smart card readers and RFID systems.

The controller may also accept information from the user regarding the type of test being performed. The controller may compare the type of test being performed with the type of sensor array present in the portable sensor array system. If an inappropriate sensor array cartridge is present, an error message may be displayed and the portable sensor array system may be disabled until the proper cartridge is inserted. In this manner, incorrect testing resulting from the use of the wrong sensor cartridge may be avoided.

The controller may also monitor the sensor array cartridge and determine if the sensor array cartridge is functioning properly. The controller may run a quick analysis of the sensor array to determine if the sensor array has been used and if any analytes are still present on the sensor array. If analytes are detected, the controller may initiate a cleaning sequence, where a cleaning solution is passed over the sensor array until no more analytes are detected. Alternatively, the controller may signal the user to replace the cartridge before testing is initiated.

Figure 19A:
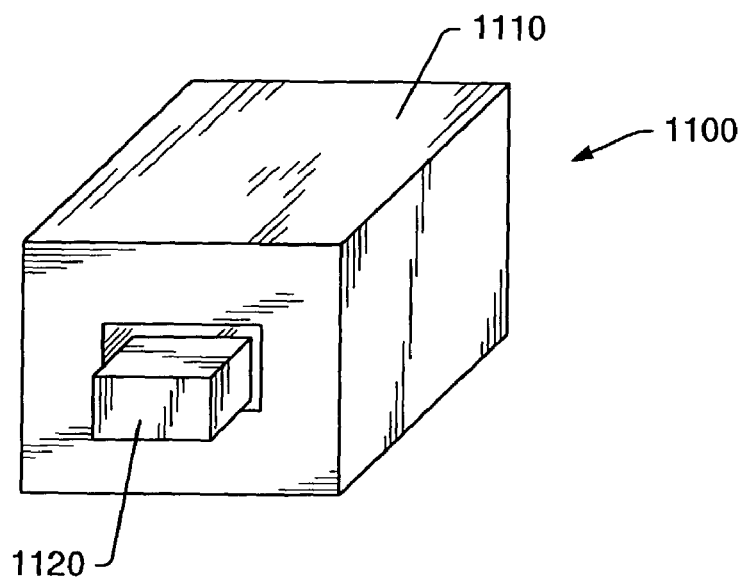
FIGS. 19A-B depict views of an embodiment of an alternate portable sensor array.
Figure 19B:
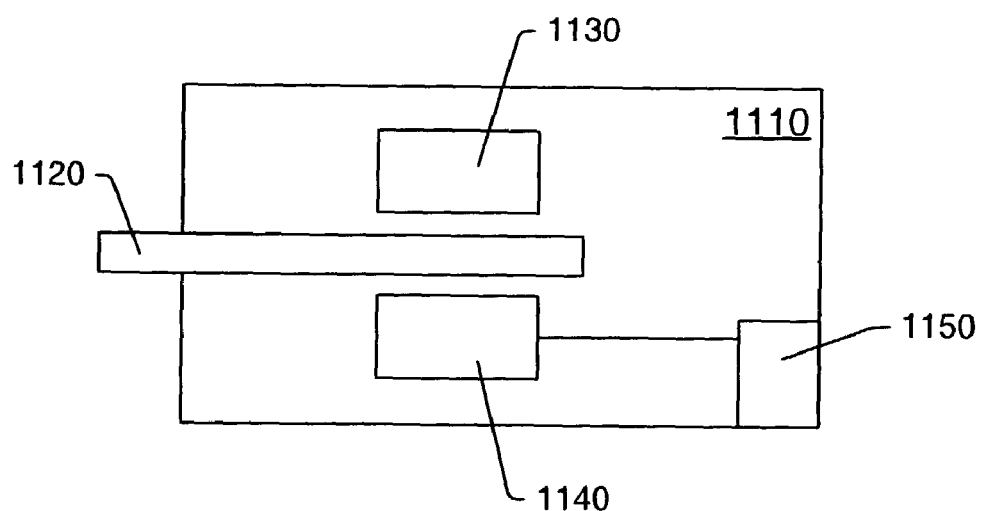

Another embodiment of a portable sensor array system is depicted in FIGS. 19A and 19B. In this embodiment, portable sensor array 1100 includes body 1110 that holds the various components used with the sensor array system. A sensor array, such as the sensor arrays described herein, may be placed in cartridge 1120. Cartridge 1120 may support the sensor array and allow the proper positioning of the sensor array within the portable sensor system.

A schematic cross-sectional view of the body of the portable sensor array system is depicted in FIG. 19B. Cartridge 1120, in which the sensor array is disposed, extends into body 1110. Within the body, light source 1130 and detector 1140 are positioned proximate to cartridge 1120. When cartridge 1120 is inserted into the reader, the cartridge may be held by body 110 at a position proximate to the location of the sensor array within the cartridge. Light source 1130 and detector1140 may be used to analyze samples disposed within the cartridge. Electronic controller 1150 may be coupled to detector 1140. Electronic controller 1150 may be used to receive data collected by the portable sensor array system. The electronic controller may also be used to transmit data collected to a computer.

Figure 20:
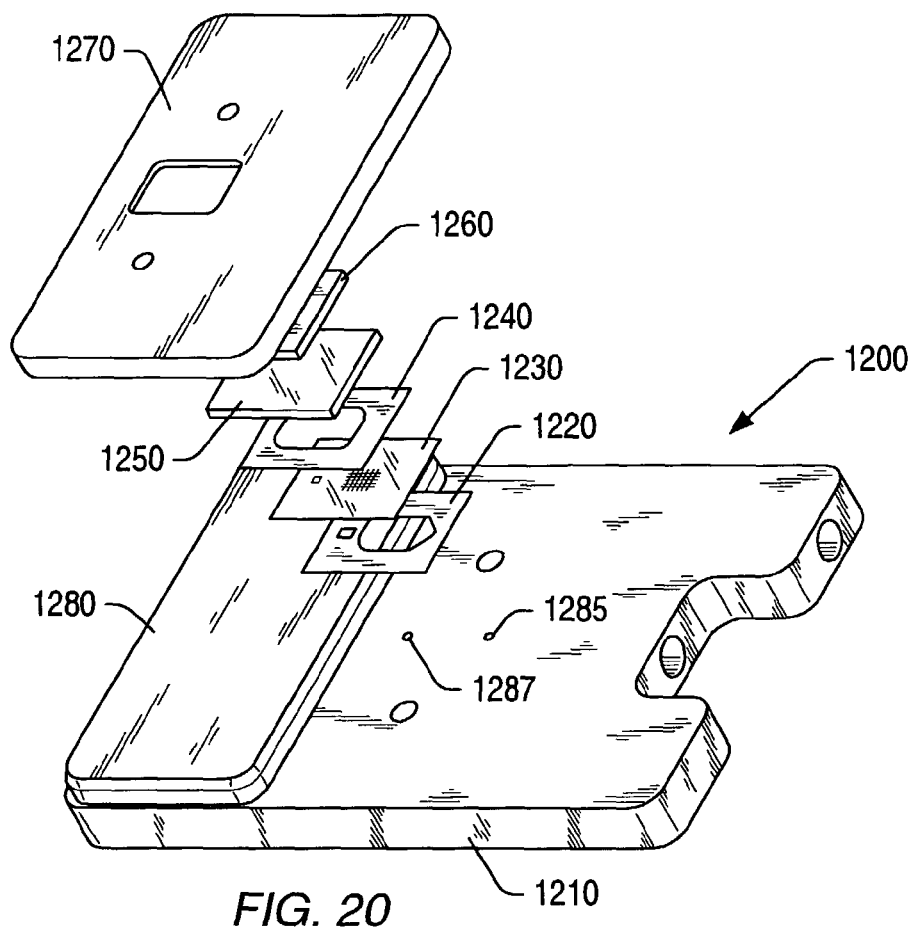
FIG. 20 depicts an exploded view of a cartridge for use in an embodiment of a portable sensor array.

An embodiment of a cartridge for use in a sensor array system is depicted in FIG. 20. Cartridge 1200 includes carrier body 1210 that is formed of a material that is substantially transparent to a wavelength of light used by the detector. In an embodiment, plastic materials may be used. Examples of plastic materials that may be used include polycarbonates and polyacrylates. In one embodiment, body 1210 may be formed from a Cyrolon AR2 Abrasion Resistant polycarbonate sheet at a thickness of about 0.118 inches and about 0.236 inches. Sensor array gasket 1220 may be placed on carrier body 1210. Sensor array gasket 1220 may help reduce or inhibit the amount of fluids leaking from the sensor array. Leaking fluids may interfere with the testing being performed.

Sensor array 1230 may be placed onto sensor array gasket 1220. The sensor array may include one or more cavities, each of which includes one or more particles disposed within the cavities. The particles may react with an analyte present in a fluid to produce a detectable signal. Any of the sensor arrays described herein may be used in conjunction with the portable reader.

Second gasket 1240 may be positioned on sensor array 1230. Second gasket 1240 may be disposed between sensor array 1230 and window 1250. Second gasket 1240 may form a seal inhibiting leakage of the fluid from the sensor array. Window 1250 may be disposed above the gasket to inhibit damage to the sensor array.

Coupling cover 1270 to body 1210 may complete the assembly. Rubber gasket 1260 may be disposed between the cover and the window to reduce pressure exerted by the cover on the window. The cover may seal the sensor array, gaskets, and window into the cartridge. The sensor array, gaskets and window may all be sealed together using a pressure sensitive adhesive. An example of a pressure sensitive adhesive is Optimount 237 made by Seal products. Gaskets may be made from polymeric materials. In one example, Calon II—High Performance material from Arlon may be used. The rubber spring may be made from a silicon rubber material.

The cover may be removable or sealed. When a removable cover is used, the cartridge may be reused by removing the cover and replacing the sensor array. Alternatively, the cartridge may be a one-use cartridge in which the sensor array is sealed within the cartridge.

Figure 21:
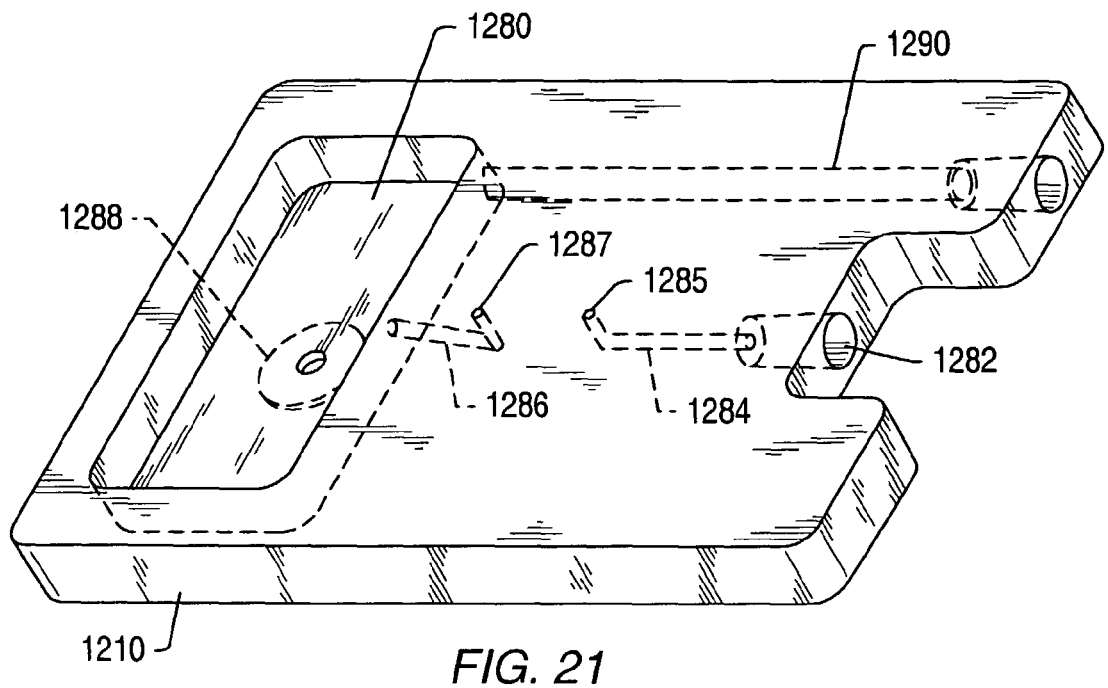
FIG. 21 depicts a cross sectional view of a cartridge for use in an embodiment of a portable sensor array.

The cartridge may also include reservoir 1280. The reservoir may hold an analyte containing fluid after the fluids pass through the sensor array. FIG. 21 depicts a cut away view of the cartridge that shows the positions of channels formed in the cartridge. The channels may allow the fluids to be introduced into the cartridge. The channels also may conduct the fluids from the inlet to the sensor array and to the reservoir.

In one embodiment, cartridge body 1210 includes a number of channels disposed throughout the body. Inlet port 1282 may receive a fluid delivery device for the introduction of fluid samples into the cartridge. In one embodiment, the inlet port may include a Luer lock adapter to couple with a corresponding Luer lock adapter on the fluid delivery device. For example, a syringe may be used as the fluid delivery device. The Luer lock fitting on the syringe may be coupled with a mating Luer lock fitting on inlet port 1282. Luer lock adapters may also be coupled to tubing, so that fluid delivery may be accomplished by the introduction of fluids through appropriate tubing to the cartridge.

Fluid passes through channel 1284 to channel outlet 1285. Channel outlet 1285 may be coupled to an inlet port on a sensor array. Channel outlet 1285 is also depicted in FIG. 20.

The fluid travels into the sensor array and through the cavities. After passing through the cavities, the fluid exits the sensor array and enters channel 1286 via channel inlet 1287. The fluid passes through channel 1286 to reservoir 1280. To facilitate the transfer of fluids through the cartridge, the reservoir may include air outlet port 1288. Air outlet port 1288 may allow air to pass out of the reservoir, while retaining any fluids disposed within the reservoir. In one embodiment, air outlet port 1288 may be an opening formed in the reservoir that is covered by a semipermeable membrane. A commercially available air outlet port includes a DURAVENT container vent, available from W. L. Gore. It should be understood, however, that any other material that allows air to pass out of the reservoir, while retaining fluids in the reservoir, might be used. After extended use, reservoir 1280 may become filled with fluids. Outlet channel 1290 may also be formed extending through body 1210 to allow removal of fluids from the body. Fluid cartridges 1292 for introducing additional fluids into the sensor array may be incorporated into the cartridges.

Transmitting Chemical Information Over A Computer Network

Herein we describe a system and method for the collection and transmission of chemical information over a computer network. The system, in some embodiments, includes an analyte detection device ("ADD") operable to detect one or more analytes or mixtures of analytes in a fluid containing one or more analytes, and computer hardware and software operable to send and receive data over a computer network to and from a client computer system.

Chemical information refers to any data representing the detection of a specific chemical or a combination of chemicals. These data may include, but are not limited to chemical identification, chemical proportions, or various other forms of information related to chemical detection. The information may be in the form of raw data, including binary or alphanumeric, formatted data, or reports. In some embodiments, chemical information relates to data collected from an analyte detection device. Such data includes data related to the color of the particles included on the analyte detection device. The chemical information collected from the analyte detection device may include raw data (e.g., a color, RBG data, intensity at a specific wavelength) etc. Alternatively, the data may be analyzed by the analyte detection device to determine the analytes present. The chemical information may include the identities of the analytes detected in the fluid sample. The information may be encrypted for security purposes.

In one embodiment, the chemical information may be in Logical Observation Identifiers Names and Codes (LOINC) format. The LOINC format provides a standard set of universal names and codes for identifying individual laboratory results (e.g. hemoglobin, serum sodium concentration), clinical observations (e.g. discharge diagnosis, diastolic blood pressure) and diagnostic study observations, (e.g. PR-interval, cardiac echo left ventricular diameter, chest xray impression).

More specifically, chemical information may take the form of data collected by the analyte detection system. As described above, an analyte detection system may include a sensor array that includes a particle or particles. These particles may produce a detectable signal in response to the presence or absence of an analyte. The signal may be detected using a detector. The detector may detect the signal. The detector may also produce an output signal that contains information relating to the detected signal. The output signal may, in some embodiments be the chemical information.

In some embodiments, the detector may be a light detector and the signal produced by the particles may be modulated light. The detector may produce an output signal that is representative of the detected light modulation. The output signal may be representative of the wavelength of the light signal detected. Alternatively, the output signal may be representative of the strength of the light signal detected. In other embodiments, the output signal may include both wavelength and strength of signal information.

In some embodiments, use of a light source may not be necessary. The particles may rely on the use of chemiluminescence, thermolumninescence or piezoluminescence to provide a signal. In the presence of an analyte of interest, the particle may be activated such that the particles produce light. In the absence of an analyte, the particles may not exhibit produce minimal or no light. The chemical information may be related to the detection or absence of a light produced by the particles, rather than modulated by the particles.

The detector output signal information may be analyzed by analysis software. The analysis software may convert the raw output data to chemical information that is representative of the analytes in the analyzed fluid system. The chemical information may be either the raw data before analysis by the computer software or the information generated by processing of the raw data.

The term "computer system" as used herein generally describes the hardware and software components that in combination allow the execution of computer programs. The computer programs may be implemented in software, hardware, or a combination of software and hardware. Computer system hardware generally includes a processor, memory media, and input/output (I/O) devices. As used herein, the term "processor" generally describes the logic circuitry that responds to and processes the basic instructions that operate a computer system. The term "memory medium" includes an installation medium, e.g., a CD-ROM, floppy disks; a volatile computer system memory such as DRAM, SRAM, EDO RAM, Rambus RAM, etc.; or a non-volatile memory such as optical storage or a magnetic medium, e.g., a hard drive. The term "memory" is used synonymously with "memory medium" herein. The memory medium may comprise other types of memory or combinations thereof. In addition, the memory medium may be located in a first computer in which the programs are executed, or may be located in a second computer that connects to the first computer over a network. In the latter instance, the second computer provides the program instructions to the first computer for execution. In addition, the computer system may take various forms, including a personal computer system, mainframe computer system, workstation, network appliance, Internet appliance, personal digital assistant (PDA), television system or other device. In general, the term "computer system" can be broadly defined to encompass any device having a processor that executes instructions from a memory medium.

The memory medium may stores a software program or programs for the reception, storage, analysis, and transmittal of information produced by an Analyte Detection Device (ADD). The software program(s) may be implemented in any of various ways, including procedure-based techniques, component-based techniques, and/or object-oriented techniques, among others. For example, the software program may be implemented using ActiveX controls, C++ objects, JavaBeans, Microsoft Foundation Classes (MFC), or other technologies or methodologies, as desired. A central processing unit (CPU), such as the host CPU, for executing code and data from the memory medium includes a means for creating and executing the software program or programs according to the methods, flowcharts, and/or block diagrams described below.

A computer system's software generally includes at least one operating system such as Windows NT, Windows 95, Windows 98, or Windows ME (all available from Microsoft Corporation); Mac OS and Mac OS X Server (Apple Computer, Inc.), MacNFS (Thursby Software), PC MACLAN (Miramar Systems), or real time operating systems such as VXWorks (Wind River Systems, Inc.), QNX (QNX Software Systems, Ltd.), etc. The foregoing are all examples of specialized software programs that manage and provide services to other software programs on the computer system. Software may also include one or more programs to perform various tasks on the computer system and various forms of data to be used by the operating system or other programs on the computer system. Software may also be operable to perform the functions of an operating system (OS). The data may include but is not limited to databases, text files, and graphics files. A computer system's software generally is stored in non-volatile memory or on an installation medium. A program may be copied into a volatile memory when running on the computer system. Data may be read into volatile memory as the data is required by a program.

A server program may be defined as a computer program that, when executed, provides services to other computer programs executing in the same or other computer systems. The computer system on which a server program is executing may be referred to as a server, though it may contain a number of server and client programs. In the client/server model, a server program awaits and fulfills requests from client programs in the same or other computer systems. Examples of computer programs that may serve as servers include: Windows NT (Microsoft Corporation), Mac OS X Server (Apple Computer, Inc.), MacNFS (Thursby Software), PC MACLAN (Miramar Systems), etc A web server is a computer system, which maintains a web site browsable by any of various web browser software programs. As used herein, the term 'web browser' refers to any software program operable to access web sites over a computer network.

An intranet is a network of networks that is contained within an enterprise. An intranet may include many interlinked local area networks (LANs) and may use data connections to connect LANs in a wide area network (WAN). An intranet may also include connections to the Internet. An intranet may use TCP/IP, HTTP, and other Internet protocols.

An extranet, or virtual private network, is a private network that uses Internet protocols and public telecommunication systems to securely share part of a business' information or operations with suppliers, vendors, partners, customers, or other businesses. An extranet may be viewed as part of a company's intranet that is extended to users outside the company. An extranet may require security and privacy. Companies may use an extranet to exchange large volumes of data, share product catalogs exclusively with customers, collaborate with other companies on joint development efforts, provide or access services provided by one company to a group of other companies, and to share news of common interest exclusively with partner companies.

Connection mechanisms included in a network may include copper lines, optical fiber, radio transmission, satellite relays, or any other device or mechanism operable to allow computer systems to communicate.

As used herein, ADD refers to any device or instrument operable to detect one or more specific analytes or mixtures of analytes in a fluid sample, wherein the fluid sample may be liquid, gaseous, solid, a suspension of a solid in a gas, or a suspension of a liquid in a gas. More particularly, an ADD includes a sensor array, light and detector are described in U.S. patent application Ser. No. 10/072,800, which is fully incorporated herein by reference as if set forth herein.

Formation of Cavities With Retaining Projections

In an embodiment, a mask may be deposited on a substrate, such as a bulk crystalline <100> silicon substrate, to form an integrated cover layer. The mask may be, but is not limited to, silicon nitride, silicon dioxide, polysilicon, a polymer, a dry film photoresist material, or a combination thereof. The mask may be deposited on the substrate. Masks formed from silicon nitride, silicon dioxide, and/or polysilicon layer may be deposited on the substrate through lowpressure chemical vapor deposition (LPCVD). Alternatively, a polymeric mask may be fastened to the substrate using an appropriate adhesive. In another embodiment, a photoresist material may be coated onto the substrate and developed to produce a mask.

An opening may be formed in the mask by etching or cutting a portion of the mask. The opening in the mask may extend through the mask such that a portion of the underlying substrate is exposed through the opening in the mask. After an opening is formed in the mask, an etchant may be applied to the substrate to remove a portion of the substrate exposed through the opening of the mask.

Figure 22A:
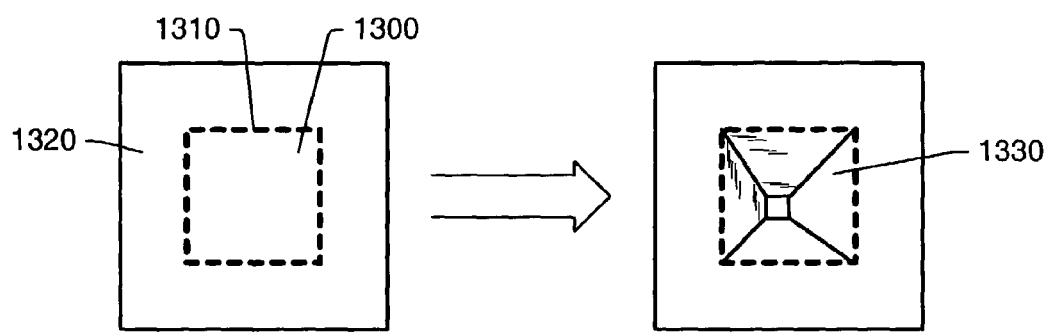
FIG. 22A depicts formation of a cavity in (100) silicon etched through a square opening in a mask in an embodiment of a sensor array system.
Figure 22B:
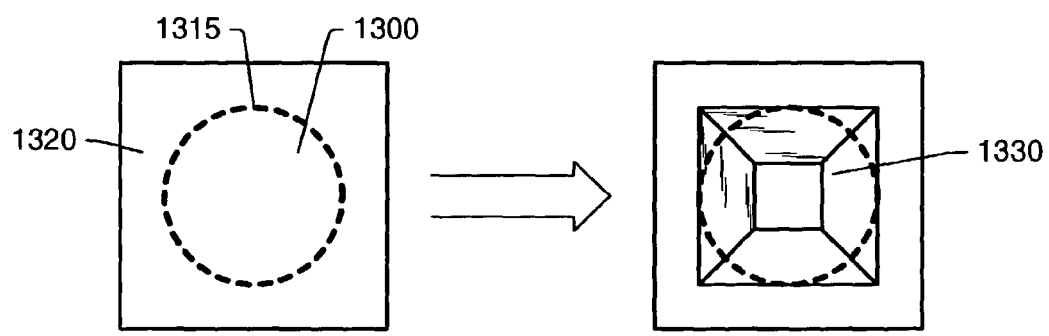
FIG. 22B depicts formation of a cavity in (100) silicon etched through a circular opening in a mask in an embodiment of a sensor array system.

In one embodiment, the substrate may be formed of silicon. When a silicon substrate is etched, the shape of the opening may define the portion of the silicon that is etched and, therefore, the size of the cavities. Cavities may be formed by an anisotropic etch process of the silicon wafer. In one embodiment, anisotropic etching of the silicon wafer is accomplished using a wet hydroxide etch. The openings formed in the mask may define the portion of the substrate that is etched. Anisotropic etching of silicon may form cavities such that the sidewalls of the cavities are substantially tapered at an angle of between about 50 to 60 degrees. Formation of such angled cavities may be accomplished by wet anisotropic etching of <100> silicon. The term "<100> silicon" refers to the crystal orientation of the silicon wafer. Other types of silicon, (e.g., <110> and <111> silicon) may lead to steeper angled sidewalls. For example, <111> silicon may lead to sidewalls formed at about 90 degrees. The etch process may be controlled so that the formed cavities extend through the silicon substrate The size of the opening formed in the mask may determine the size of the cavity formed during etching of the silicon substrate, but may not determine the shape of the cavity. For example, FIGS. 22A-B depicts masks formed over a silicon substrate. In FIG. 22A, a substantially square opening 1310 is formed in a mask 1320 such that a portion of the silicon substrate 1300 is exposed. When the substrate is exposed to etching conditions, a cavity 1330 is formed. The size and shape of the cavity is complementary to the shape and size of the opening. Etching is substantially inhibited in the portions of the substrate that are covered by the mask 1320.

In FIG. 22B, a circular opening 1315 is formed in a mask 1320. When the exposed portion of the silicon substrate is etched using, e.g., a wet hydroxide etch, a pyramidal cavity 1330 is obtained. The circular opening 1310 defines the size of the cavity formed, but does not define the shape. The size of the cavity formed is complementary to the diameter of the circular opening. As depicted in FIG. 22B, the edge of the cavity extends to the edge of the circle. It will be further noted, however, that the cavity retains its pyramidal shape.

In some embodiments, a silicon-rich layer (e.g., silicon-rich silicon nitride) may be deposited on the substrate. The silicon-rich layer may provide a low stress layer advantageous for forming flexible projections. Flexible projections formed in a low stress layer may allow easier elastic bending of the flexible projections. Insertion of a particle through the flexible projections may also be substantially easier.

Figure 23A:
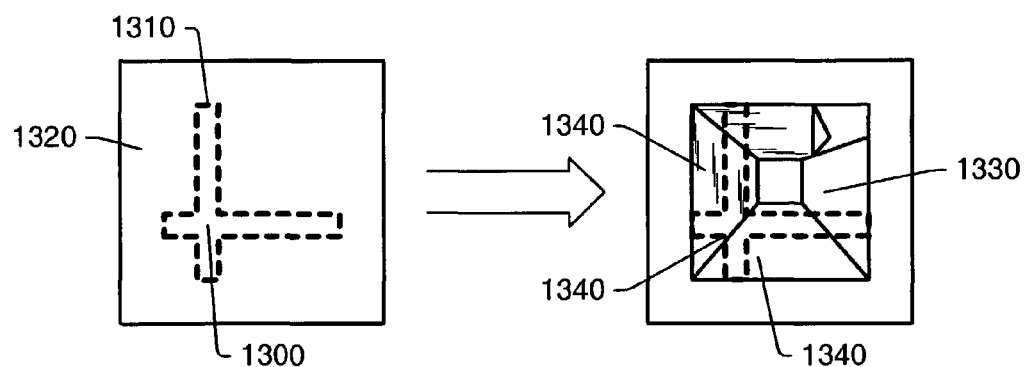
FIGS. 23A-B depict formation of a cavity in (100) silicon etched through cross structured openings in a mask in an embodiment of a sensor array system.
Figure 23B:
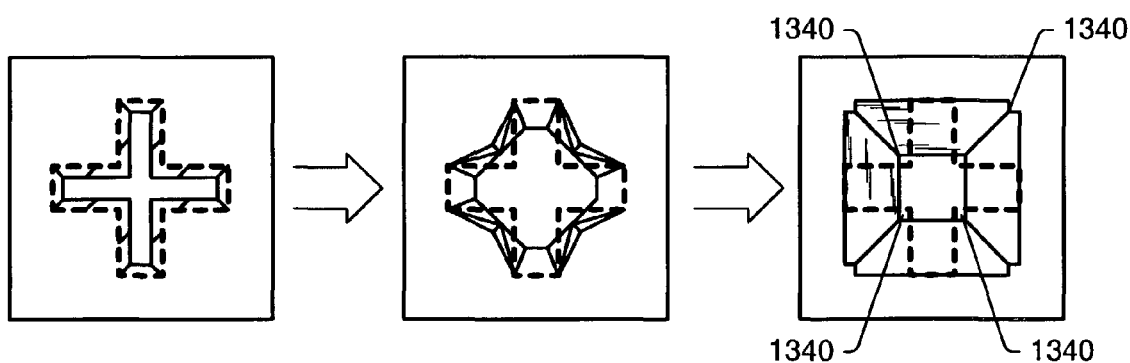
Figure 24A:
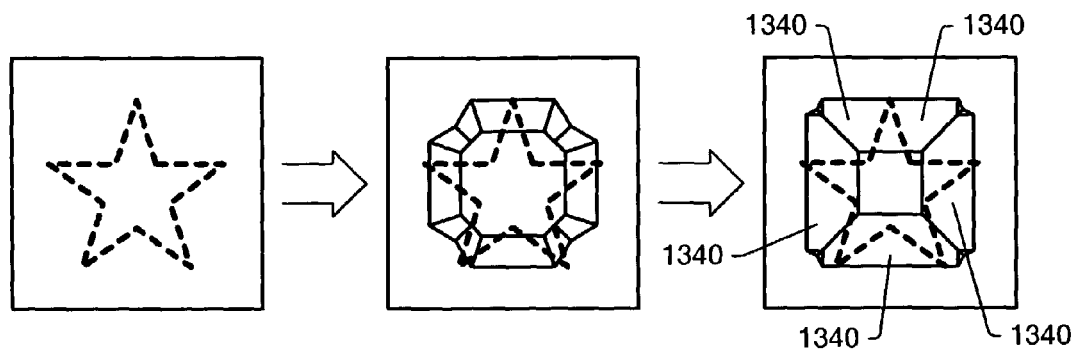
FIGS. 24A-C depict formation of a cavity in (100) silicon etch through various star pattern structured openings in a mask in an embodiment of a sensor array system.
Figure 24B:
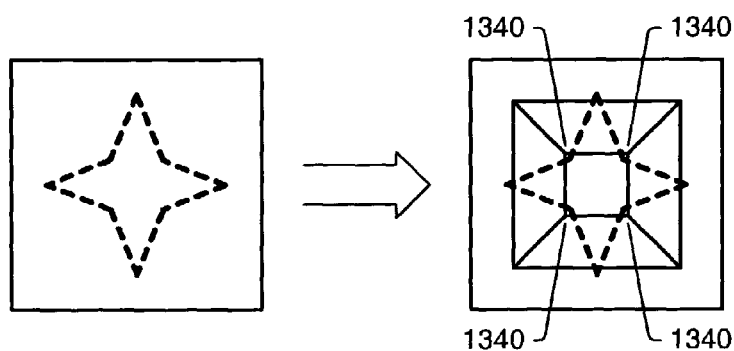
Figure 24C:
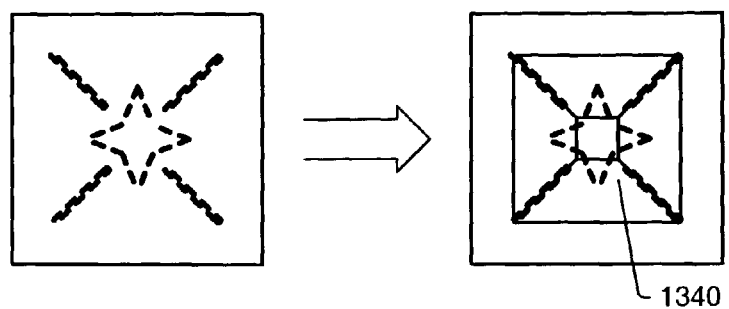

FIGS. 23 and 24 depict other shapes for openings that may be used to define the size, but not the shape, of a cavity that is formed in a silicon substrate. As can be seen in these examples, the size of the cavity is determined by the length and width of the openings. For example, in FIG. 23A, two slots are depicted. The width of the first slot and the width of the second slot control the size of the etching but, to some extent, allow a pyramidal cavity to be formed. Other shapes, as depicted in the other figures, may be used to form cavities. Generally, the to form a cavity having a predefined shape, an opening, need only have a width and length that corresponds to the length and width of the desired cavity regardless of the shape of the opening.

In some embodiments, this feature of forming cavities using different shaped openings may be used to form cavities that include projections that extend over a portion of the upper surface of the cavity. FIGS. 23 and 24 show structures that may provide flexible projections over a formed cavity after the substrate is etched. In FIG. 23B, a cross-shaped opening may be formed over the substrate. The substrate may be subjected to an anisotropic etching to form a cavity in the substrate. Initially the cavity is formed in the regions of the substrate exposed through the opening. As etching continues, the cavity expands to regions below the mask, undercutting a portion of the mask. After a sufficient amount of time has passed the cavity may be as depicted in the last panel of FIG. 23B. The cavity has a size that is complementary to the length and width of the opening. The cavity, however, has undercut a portion of the mask. The undercut portion of the mask forms projections 1340, which extend over a portion of the cavity. As will be discussed in more detail later, these projections may be used to help retain a particle within the cavity.

FIGS. 24 A-C depict alternate embodiments of masks having openings that produce projections after etching. As depicted in these figures different size shapes may produce different size cavities. As described in more detail below, the ability to form different size cavities and different having masks with different size openings may be useful for placing particles in the cavities. Any of the cavities formed with the above-described mask may be formed through substrate 1300 such that a bottom opening is also present.

Figure 25:
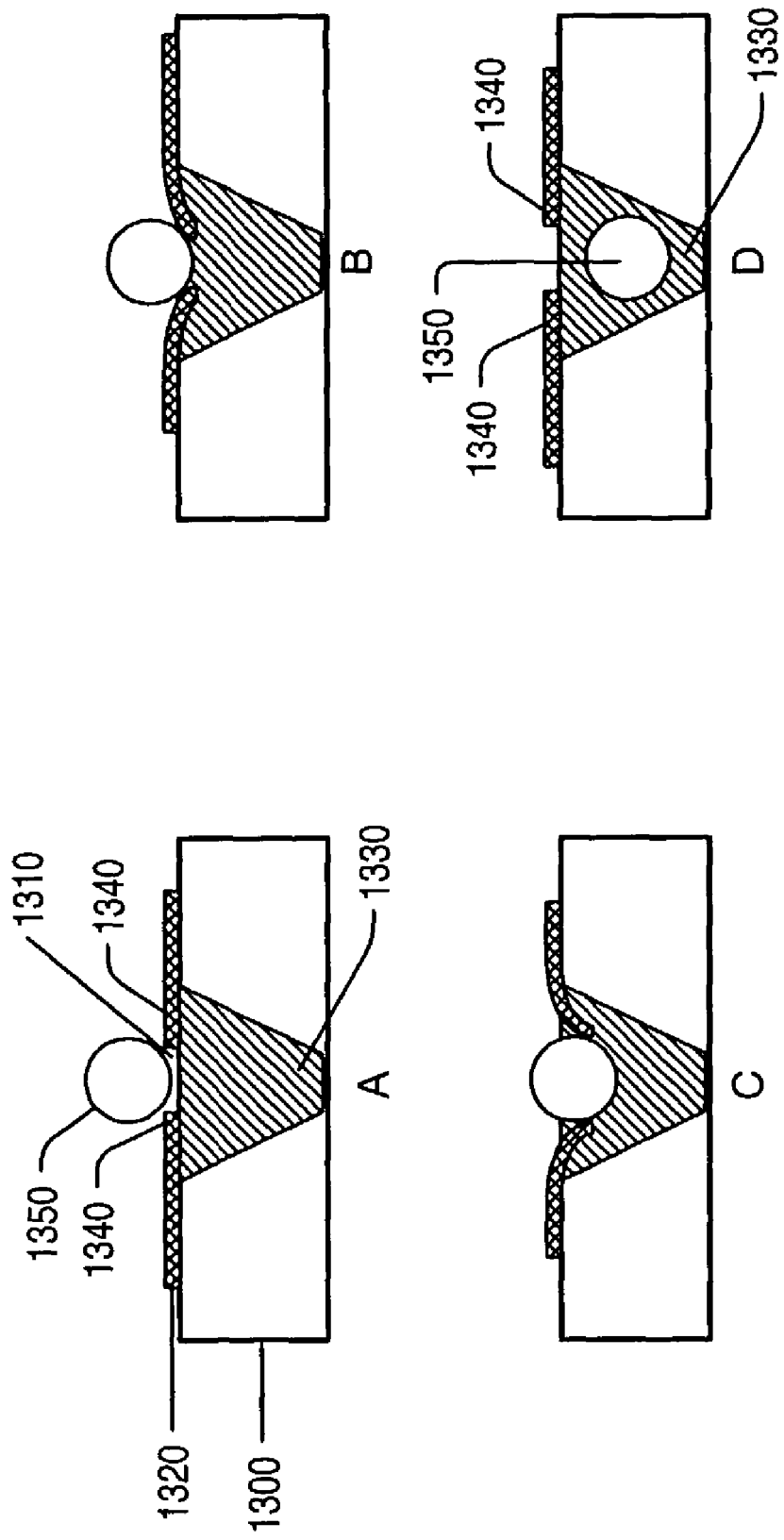
FIGS. 25A-D depict insertion of a particle through flexible projections over a cavity in a substrate in an embodiment of a sensor array system.

An integrated cover layer of flexible projections 1340 formed in mask 1320 may provide a method of retaining particle 1350 in cavity 1330. In an embodiment shown in FIG. 25, flexible projections 1340 may be produced over cavity 1330. Mask opening 1310 may be smaller than the top of underlying cavity 1330. Particle 1350 may be inserted through flexible projections 1340 into cavity 1330 as depicted in FIG. 25. As particle 1350 passes flexible projections 1340, the flexible projections may elastically bend downward, as shown in FIG. 25B and FIG. 25C, until the particle passes completely by the flexible projections and into cavity 1330. As shown in FIG. 25D, after particle 1350 passes flexible projections 1340, the flexible projections may elastically return to their original position, thereby providing retention of the particle in cavity 1330 Retention of particle 1350 in cavity 1330 may be maintained by flexible projections 1340 during subsequent handling of the sensor array.

Figure 26:
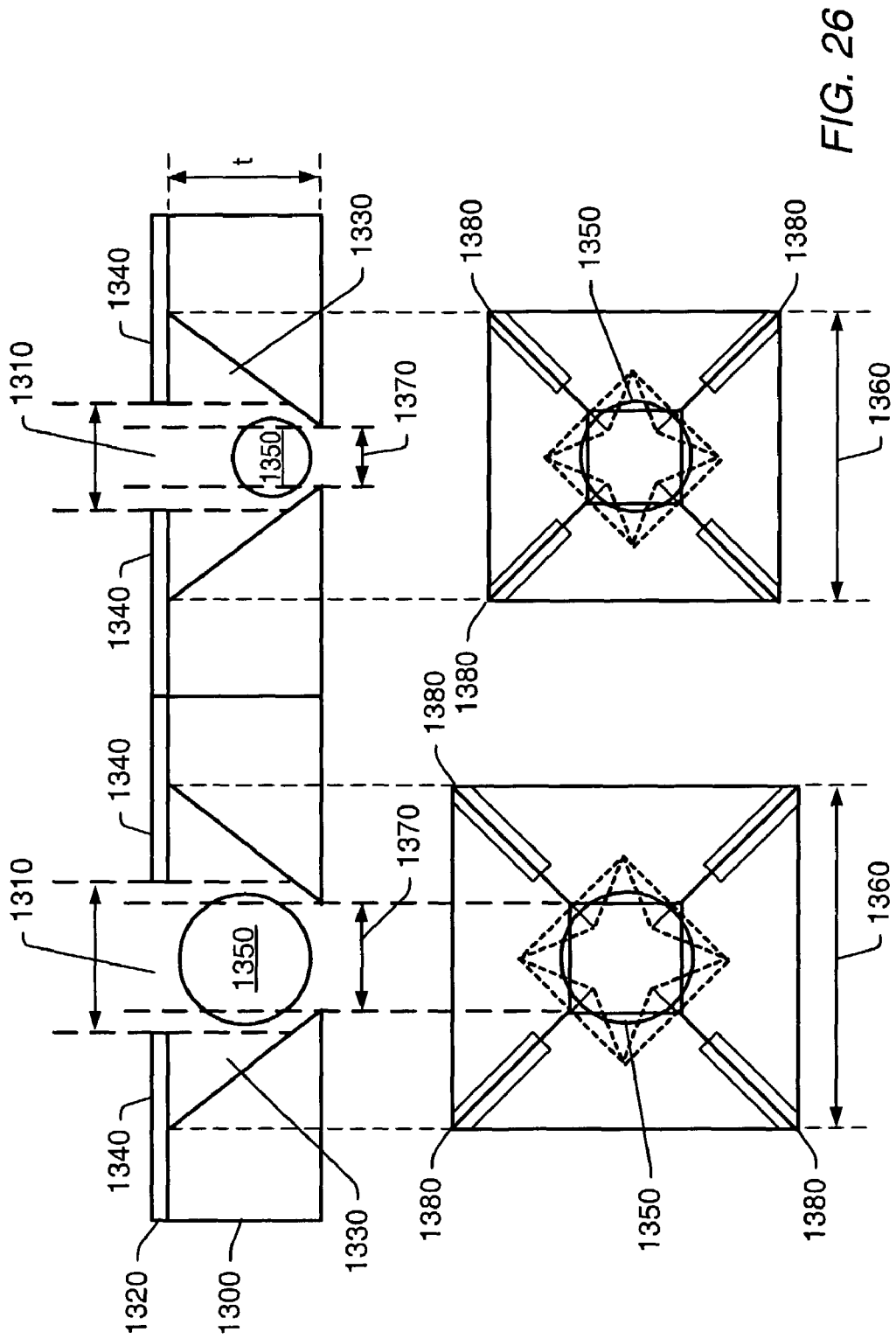
FIG. 26 depict cross sectional and top views of cavities and flexible projections formed for specific size selection of particles in an embodiment of a sensor array system.

FIG. 26 shows cross sectional and top views of cavity 1330 with flexible projections 1340 formed for specific size selection of particle 1350 to be captured and retained in the cavity. In one embodiment, a 100 cm$^2$ silicon substrate may have from about 101 to about 106 mask openings and cavities. Mask openings 1310 may be substantially the same size across substrate 1300 or may be of different sizes. As shown in FIG. 26, the size and shape of top opening 1360 of cavity 1330 may be determined by location of corners 1380 of in mask openings 1310. Size and shape of bottom opening 1370 may be determined by location of corners 1380 and thickness of substrate 1300. As such, the size and shape of the top and bottom openings for each cavity may be controlled independently. Each cavity 1330 and flexible projections 1340 may be designed for a specific size particle 1350.

An array of cavities 1330 in substrate 1300 may be formed to automatically sort specific size particles 1350 into specific cavities based on a size of the particle; e.g., based on the diameter of the particle. Large particle 1350 with a diameter larger than top-opening 1360 of cavity 1330 may be substantially inhibited from entering the cavity. Large particle 1350 with a diameter smaller than bottom opening 1370 of cavity 1330 may enter top opening 1360 through flexible projections 1340. Smaller particle 1350 will then pass through bottom opening 1370 and out of the cavity. Small particle 1350 with a diameter smaller than top opening 1360 and larger than bottom opening 1370 may be captured in cavity 1330 and retained in the cavity with flexible projections 1340.

In an embodiment of a sensor array, different sized particles 1350 may be used to target different types of analytes of interest. A mixture of particles having predetermined sizes may be introduced to the array. The array of cavities 1330 may be designed for specific particle sizes to automatically sort the correct size particle 1350 into each cavity. In a sensor array system, flexible projections 1340 may be transparent to the wavelength of light of a light source used for illuminating particles 1350 in cavities 1330.

In an embodiment, a particle may be placed in a cavity using various techniques. Micromanipulators may be used in for individual placement of a particle in a cavity or particles in an array of cavities. A vacuum or flow system may be used for more rapid placement of particles in an array of cavities. In an embodiment, a substrate may be fabricated a cavity or cavities designed to select a desired particle size. A solution with a wide particle size distribution range may be produced. The substrate may be dipped into the solution. A vacuum or other fluid flow may pull a particle past flexible projections and into a top opening of a cavity. A too large particle may not pass through the top opening into the cavity. A too small particle may pass through the cavity and out a bottom opening of the cavity. The flexible projections may not necessary bend as a particle passes through the projections if the particle is too large. A particle of desired size may pass through the flexible projections in the top opening and be retained in the cavity.

Figure 27A:
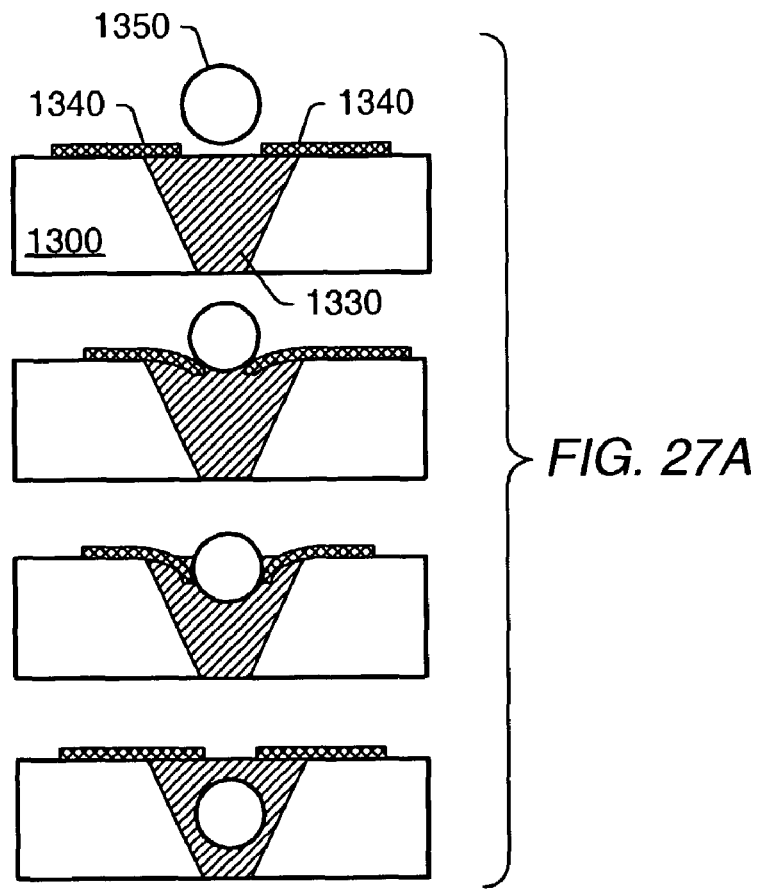
FIGS. 27A-B depict insertion of a shrunken particle through flexible projections over a cavity in a substrate in an embodiment of a sensor array system.
Figure 27B:
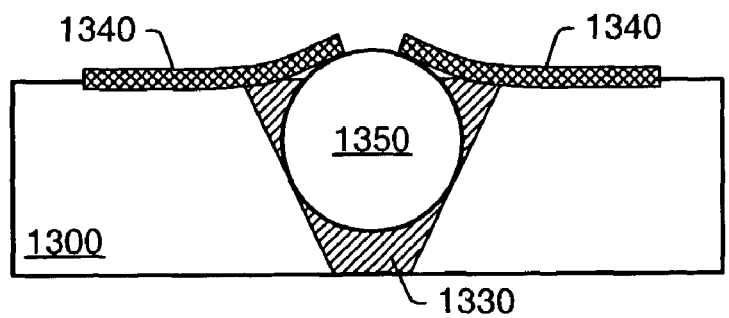

In another embodiment, a cavity is formed in a substrate by undercutting a mask to produce flexible projections in the mask during anisotropic etching of a silicon substrate as described previously. The integrated cover layer formed by the mask and flexible projections and the top and bottom opening of the cavity in the substrate may be fabricated for a desired diameter size of a particle in a shrunken state. A particle to be placed within the cavity may be exposed to a medium in which the particle may be caused to shrink. As shown in FIG. 27A, particle 1350 may be easily inserted through flexible projections 1340 into cavity 1330 of substrate 1300 in its shrunken state. After insertion of particle 1350 into cavity 1330 the particle may be exposed to a medium which causes the particle to return to its normal state as shown in FIG. 27B. Particle 1350 may be captured within cavity 1330 by flexible projections 1340 after it returns to its normal size. By correctly designing the swollen state of particle 1350 and flexible projections 1340, the particle may be retained within the cavity during subsequent processing.

A combination of correctly sized flexible projections and particles may be used to produce a backflow limiter and pump or check valve. In an embodiment, slit openings in a mask may be used to form a cavity in a substrate with a rectangular bottom opening. A second mask may be used to form an opening over the cavity, which is smaller than the desired size particle to be retained in the cavity. The second mask may form a circular opening slightly smaller than a diameter of the particle.

The flexible projections from the openings in the masks over the cavity may be designed for placement of a specific size particle into the cavity. A fluid flow may be allowed through the cavity from the top opening through the bottom opening. If the flow is reversed, the flexible projections over and particle in the cavity may stop or substantially inhibited flow out of the top opening. Flow from the bottom opening may force the particle against the circular top opening and block flow from the cavity. The slits in the mask may be as small as possible resulting in a significant decrease in backflow capabilities through the slits if the flow is reversed or stopped. In an embodiment, small slit openings in the mask may be sufficient to prevent back-flow through the cavity without a second mask with a circular opening. These embodiments may produce a valve with a high flow coefficient for flow in one direction and a low flow coefficient in the opposite direction.

The flexible projections may be designed to bend in one direction more favorably than in the opposite direction. In an embodiment, multiple lithography or deposition steps for producing cover layers may provide a flexible projection, which may elastically bend preferably in a direction to allow placement of a particle within the cavity. For example, a second silicon nitride and/or silicon dioxide layer may be deposited over the first mask to substantially inhibit the flexible projections from moving from an initial position to a position away from the cavity. The flexibility may be reduced in the direction in which the projections may be required to flex for removal of the particle in a direction away from the cavity. Providing enhanced flexibility in only one flexural direction may allow reduction of slit size in the cover layer needed to provide etch access to the silicon substrate. In another embodiment, the flexible projections may be electrically actuated for insertion of a particle or when fluid flow into the cavity is desired.

For determining the probability of a correct size particle being placed in a cavity, an embodiment assumes a gaussian distribution of particle diameters in a solution of particles. In a non-limiting example, an opening of flexible projections in a cover layer positioned over a top opening of a cavity is sized to some constant value times a sigma value larger than the mean diameter of particles in the solution. The sigma value as defined hereinafter is the variability in size of a particle around the mean particle diameter of a gaussian distribution of particles. A bottom opening of the cavity is sized to the constant value times the sigma value smaller than the mean diameter of the particles in the solution. In this example, using top and bottom openings sized one sigma from the mean diameter particle size, there is approximately an 84% probability that the mean sized particle will be correctly placed in the cavity.

For a 10% sigma of particle diameters, ±1 sigma sized top and bottom openings of a cavity, and 1 sigma separation between the next larger size bottom opening and the next smaller size top opening, only the next particle diameter size up or down from the mean particle size may have a significant probability of filling the cavity. Assuming these variables, the probability for placing a particle the next size larger in the cavity is about 1 in 1000. The probability of placing a particle the next size smaller in the cavity is about 1 in 300.

A reduction in the variability of particle diameter sizes, a reduction in the variability between the top and bottom openings of the cavity, and/or an increase in the separation of the next larger bottom opening and next smaller top opening of a cavity may result in a higher percentage of correctly sized particles being placed in the cavity. For example, with a 5% sigma in particle diameters, and the same ±1 sigma sized top and bottom openings in the cavity and 1 sigma separation used in the above example, the probability for placing a particle the next size larger in the cavity is about 1 in 700. The probability of placing a particle the next size smaller in the cavity is still about 1 in 300. However, with a 5% sigma in particle diameters, ±1 sigma sized top and bottom openings in the cavity, and 2 sigma separation, the probability for placing a particle the next size larger in the cavity improves to about 1 in 800,000. The probability of placing a particle the next size down in the cavity improves to about 1 in 50,000.

Another strategy may be employed to determine particle capture selectivity probability using three cavities of a select size for triple redundancy. In this strategy, selection criteria may be used such that if two of the three cavities contain the correct particle size, the cavities may be considered correctly filled. An error may result, however, if two same-sized cavities are incorrectly simultaneously filled. The probability of placing the next size larger particle in two of the three cavities is about 1 in $10^6$. The probability of placing the next size smaller particle in two of the three cavities is about 1 in 77,000.

Error rates using the triple redundancy strategy may be reduced by decreasing the variability of particle diameters and size of the top and bottom openings of the cavity, and/or increasing the separation of the next larger size bottom opening and the next smaller size top opening. For example, with a 10% sigma of particle diameters, ±0.5 sigma sized top and bottom openings of a cavity, and 2 sigma separation between the next larger size bottom opening and the next smaller size top opening, the probability of placing the next size larger particle in two of the three cavities is about 1 in $4 \times 10^{10}$. The probability of placing the next size smaller particle in two of the three cavities is about 1 in $9 \times 10^6$.

To provide selection of only one particle size from a distribution of particle sizes, a solution of particles with a wide particle size distribution range may be allowed to flow over the substrate. As in previous embodiments described, channels may be formed in the substrate to allow flow to and away from cavities in the substrate. A vacuum or flow may be used to pull the particles into the cavities formed in the substrate. A particles with too large a diameter may not be captured by a cavity where the top opening if the cavity is smaller than the particle. Particles larger than the top opening of the cavity may continue to flow across the array. Particles with a smaller diameter than the bottom opening of the cavity may be drawn into the cavity through the top opening, but pass through the bottom opening and out of the substrate. Particle sizes smaller than the top opening, but larger than the bottom opening, may be drawn into and retained within the cavity or cavities of the substrate. The non-retained particles may flow away from the substrate.

The flow may be stopped and/or the substrate along with the captured particles may be removed from the solution of particles. A reverse flow may be used to dislodge the particles from the array to desired locations. As such, a solution of various particle sizes may be sorted by using arrays of different size cavities. A substrate may include a plurality of cavities of substantially the same size, or substantially different sizes. An integrated cover layer with flexible projections may retain desired particle sizes in the cavities during handling and/or subsequent processing. Flow through the cavity may be reversed to dislodge the particles into desired target locations. The various sized particles may be sorted or "filtered" in this manner. This method may also be used to pick-and-place many particles simultaneously on a target.

Chemically Sensitive Particles

A particle, in some embodiments, possesses both the ability to bind the analyte of interest and to create a modulated signal. The particle may include receptor molecules which posses the ability to bind the analyte of interest and to create a modulated signal. Alternatively, the particle may include receptor molecules and indicators. The receptor molecule may posses the ability to bind to an analyte of interest. Upon binding the analyte of interest, the receptor molecule may cause the indicator molecule to produce the modulated signal. The receptor molecules may be naturally occurring or synthetic receptors formed by rational design or combinatorial methods. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner. The forces, which drive association/recognition between molecules, include the hydrophobic effect, anion-cation attraction, and hydrogen bonding. The relative strengths of these forces depend upon factors such as the solvent dielectric properties, the shape of the host molecule, and how it complements the guest. Upon host-guest association, attractive interactions occur and the molecules stick together. The most widely used analogy for this chemical interaction is that of a "lock and key". The fit of the key molecule (the guest) into the lock (the host) is a molecular recognition event.

A naturally occurring or synthetic receptor may be bound to a polymeric resin in order to create the particle. The polymeric resin may be made from a variety of polymers including, but not limited to, agarous, dextrose, acrylamide, control pore glass beads, polystyrene-polyethylene glycol resin, polystyrene-divinyl benzene resin, formylpolystyrene resin, trityl-polystyrene resin, acetyl polystyrene resin, chloroacetyl polystyrene resin, aminomethyl polystyrene-divinylbenzene resin, carboxypolystyrene resin, chloromethylated polystyrene-divinylbenzene resin, hydroxymethyl polystyrene-divinylbenzene resin, 2-chlorotrityl chloride polystyrene resin, 4-benzyloxy-2'4'-dimethoxybenzhydrol resin (Rink Acid resin), triphenyl methanol polystyrene resin, diphenylmethanol resin, benzhydrol resin, succinimidyl carbonate resin, p-nitrophenyl carbonate resin, imidazole carbonate resin, polyacrylamide resin, 4-sulfamylbenzoyl-4'-methylbenzhydrylamine-resin (Safety-catch resin), 2-amino-2-(2'-nitrophenyl) propionic acid-aminomethyl resin (ANP Resin), p-benzyloxybenzyl alcohol-divinylbenzene resin (Wang resin), p-methylbenzhydrylamine-divinylbenzene resin (MBHA resin), Fmoc-2,4-dimethoxy-4'-(carboxymethyloxy)-benzhydrylamine linked to resin (Knorr resin), 4-(2',4'-DimethoxyphenylFmoc-aminomethyl)-phenoxy resin (Rink resin), 4-hydroxymethyl-benzoyl-4'-methylbenzhydrylamine resin (HNBA-MBHA Resin), p-nitrobenzophenone oxime resin (Kaiser oxime resin), and amino-2,4-dimethoxy-4'-(carboxymethyloxy)-benzhydrylamine handle linked to 2-chlorotrityl resin (Knorr-2-chlorotrityl resin). In one embodiment, the material used to form the polymeric resin is compatible with the solvent in which the analyte is dissolved. For example, polystyrene-divinyl benzene resin will swell within non-polar solvents, but does not significantly swell within polar solvents. Thus, polystyrene-divinyl benzene resin may be used for the analysis of analytes within non-polar solvents. Alternatively, polystyrene-polyethylene glycol resin will swell with polar solvents such as water. Polystyrene-polyethylene glycol resin may be useful for the analysis of aqueous fluids.

Figure 28:
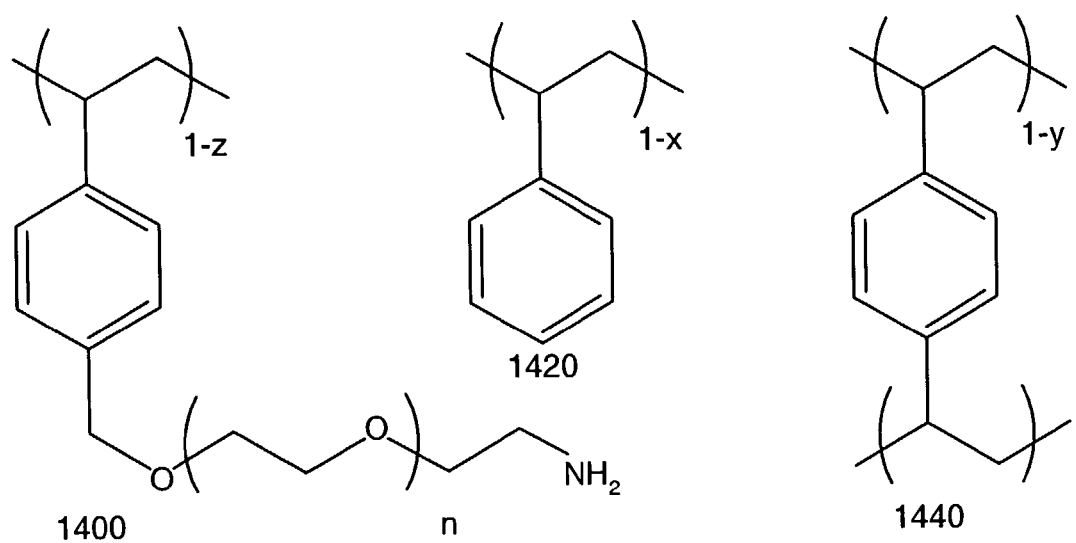
FIG. 28 depicts the chemical constituents of a particle in an embodiment of a sensor array system.

In one embodiment, a polystyrene-polyethylene glycol-divinyl benzene material is used to form the polymeric resin. The polystyrene-polyethylene glycol-divinyl benzene resin is formed from a mixture of polystyrene 1400, divinyl benzene 1420 and polystyrene-polyethylene glycol 1440 (see FIG. 28). The polyethylene glycol portion of the polystyrene-polyethylene glycol 1440, in one embodiment, may be terminated with an amine. The amine serves as a chemical handle to anchor both receptors and indicator dyes. Other chemical functional groups may be positioned at the terminal end of the polyethylene glycol to allow appropriate coupling of the polymeric resin to the receptor molecules or indicators.

The chemically sensitive particle, in one embodiment, is capable of both binding the analyte(s) of interest and creating a detectable signal. In one embodiment, the particle will create an optical signal when bound to an analyte of interest. The use of such a polymeric bound receptors offers advantages both in terms of cost and configurability. Instead of having to synthesize or attach a receptor directly to a supporting member, the polymeric bound receptors may be synthesized en masse and distributed to multiple different supporting members. This allows the cost of the sensor array, a major hurdle to the development of mass-produced environmental probes and medical diagnostics, to be reduced. Additionally, sensor arrays, which incorporate polymeric bound receptors, may be reconfigured much more quickly than array systems in which the receptor is attached directly to the supporting member. For example, if a new variant of a pathogen or a pathogen that contains a genetically engineered protein is a threat, then a new sensor array system may be readily created to detect these modified analytes by simply adding new sensor elements (e.g., polymeric bound receptors) to a previously formed supporting member.

Systems in which receptors are sensitive to changes in pH are described in U.S. patent applications Ser. Nos. 09/287,248; 09/354,882; 09/775,340; 09/775,344; 09/775,353; 09/775,048; 09/775,343; 10/072,800, which are incorporated herein by reference as if set forth herein. In these systems, a receptor, which is sensitive to changes in the pH of a fluid sample, is bound to a polymeric resin to create a particle. That is, the receptor is sensitive to the concentration of hydrogen cations ($H^+$). The receptor in this case is typically sensitive to the concentration of $H^+$ in a fluid solution. The analyte of interest may therefore be $H^+$. There are many types of molecules, which undergo a color change when the pH of the fluid is changed.

Systems in which receptors are sensitive to the concentrations of one or more metal cations present in a fluid solution are described in U.S. patent applications Ser. Nos. 09/287,248; 09/354,882; 09/775,340; 09/775,344; 09/775,353; 09/775,048; 09/775,343; 10/072,800, which are incorporated herein by reference as if set forth herein. In these systems, the receptor in this case is typically sensitive to the concentration of one or more metal cations present in a fluid solution. In general, colored molecules, which will bind cations, may be used to determine the presence of a metal cation in a fluid solution.

In one embodiment, a detectable signal may be caused by the altering of the physical properties of an indicator ligand bound to the receptor or the polymeric resin. In one embodiment, two different indicators are attached to a receptor or the polymeric resin. When an analyte is captured by the receptor, the physical distance between the two indicators may be altered such that a change in the spectroscopic properties of the indicators is produced. A variety of fluorescent and phosphorescent indicators may be used for this sensing scheme. This process, known as Forster energy transfer, is extremely sensitive to small changes in the distance between the indicator molecules.

Figure 29:
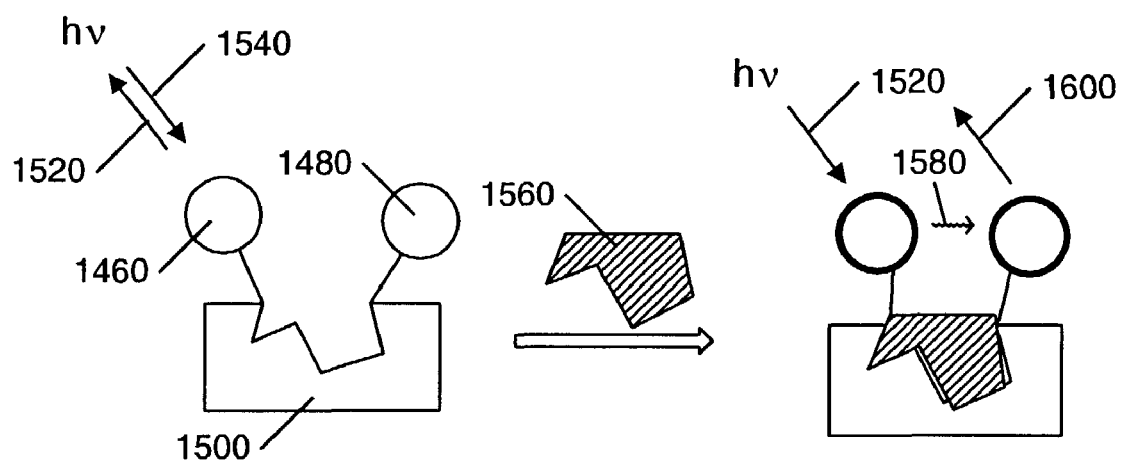
FIG. 29 depicts a schematic view of the transfer of energy from a first indicator to a second indicator in the presence of an analyte in an embodiment of a sensor array system.

For example, first fluorescent indicator 1460 (e.g., a fluorescein derivative) and second fluorescent indictor 330 (e.g., a rhodamine derivative) may be attached to receptor 1500, as depicted in FIG. 29. When no analyte is present, short wavelength excitation 1520 may excite first fluorescent indicator 1460, which fluoresces as indicated by 1540. The short wavelength excitation, however, may cause little or no fluorescence of second fluorescent indicator 1480. After binding of analyte 1560 to the receptor, a structural change in the receptor molecule may bring the first and second fluorescent indicators closer to each other. This change in intermolecular distance may allow an excited first indicator 1460 to transfer a portion of fluorescent energy 1580 to second fluorescent indicator 1480. This transfer in energy may be measured by either a drop in energy of the fluorescence of first indicator molecule 1460, or the detection of increased fluorescence 1600 by second indicator molecule 1480.

Alternatively, first and second fluorescent indicators 1460 and 1480, respectively, may initially be positioned such that short wavelength excitation causes fluorescence of both the first and second fluorescent indicators, as described above. After binding of analyte 1560 to the receptor, a structural change in the receptor molecule may cause the first and second fluorescent indicators to move, further apart. This change in intermolecular distance may inhibit the transfer of fluorescent energy from first indicator 1460 to second fluorescent indicator 1480. This change in the transfer of energy may be measured by either a drop in energy of the fluorescence of second indicator molecule 1480, or the detection of increased fluorescence by first indicator molecule 1460.

In another embodiment, an indicator ligand may be pre-loaded onto the receptor. An analyte may then displace the indicator ligand to produce a change in the spectroscopic properties of the particles. In this case, the initial background absorbance is relatively large and decreases when the analyte is present. The indicator ligand, in one embodiment, has a variety of spectroscopic properties, which may be measured. These spectroscopic properties include, but are not limited to, ultraviolet absorption, visible absorption, infrared absorption, fluorescence, and magnetic resonance. In one embodiment, the indicator is a dye having a strong fluorescence, a strong ultraviolet absorption, a strong visible absorption, or a combination of these physical properties. Examples of indicators include, but are not limited to, carboxyfluorescein, ethidium bromide, 7-dimethylamino-4-methylcoumarin, 7-diethylamino-4-methylcoumarin, eosin, erythrosin, fluorescein, Oregon Green 488, pyrene, Rhodamine Red, tetramethyirhodamine, Texas Red, Methyl Violet, Crystal Violet, Ethyl Violet, Malachite green, Methyl Green, Alizarin Red S, Methyl Red, Neutral Red, o-cresolsulfonephthalein, o-cresolphthalein, phenolphthalein, Acridine Orange, B-naphthol, coumarin, and a-naphthionic acid.

When the indicator is mixed with the receptor, the receptor and indicator interact with each other such that the above-mentioned spectroscopic properties of the indicator, as well as other spectroscopic properties, may be altered. The nature of this interaction may be a binding interaction, wherein the indicator and receptor are attracted to each other with a sufficient force to allow the newly formed receptor-indicator complex to function as a single unit. The binding of the indicator and receptor to each other may take the form of a covalent bond, an ionic bond, a hydrogen bond, a van der Waals interaction, or a combination of these bonds.

The indicator may be chosen such that the binding strength of the indicator to the receptor is less than the binding strength of the analyte to the receptor. Thus, in the presence of an analyte, the binding of the indicator with the receptor may be disrupted, releasing the indicator from the receptor. When released, the physical properties of the indicator may be altered from those it exhibited when bound to the receptor. The indicator may revert to its original structure, thus regaining its original physical properties. For example, if a fluorescent indicator is attached to a particle that includes a receptor, the fluorescence of the particle may be strong before treatment with an analyte-containing fluid. When the analyte interacts with the particle, the fluorescent indicator may be released. Release of the indicator may cause a decrease in the fluorescence of the particle, since the particle now has less indicator molecules associated with it.

In another embodiment, a designed synthetic receptor may be used. In one embodiment, a polycarboxylic acid receptor may be attached to a polymeric resin. The polycarboxylic receptors are discussed in U.S. Pat. No. 6,045,579, which is incorporated herein by reference.

In an embodiment, the analyte molecules in the fluid may be pretreated with an indicator ligand. Pretreatment may involve covalent attachment of an indicator ligand to the analyte molecule. After the indicator has been attached to the analyte, the fluid may be passed over the sensing particles. Interaction of the receptors on the sensing particles with the analytes may remove the analytes from the solution. Since the analytes include an indicator, the spectroscopic properties of the indicator may be passed onto the particle. By analyzing the physical properties of the sensing particles after passage of an analyte stream, the presence and concentration of an analyte may be determined.

For example, the analytes within a fluid may be derivatized with a fluorescent tag before introducing the stream to the particles. As analyte molecules are adsorbed by the particles, the fluorescence of the particles may increase. The presence of a fluorescent signal may be used to determine the presence of a specific analyte. Additionally, the strength of the fluorescence may be used to determine the amount of analyte within the stream.

In one embodiment, a chromogenic signal generating process may be performed to produce a color change on a particle. An analyte fluid introduced into the cavity and reacted with the receptor. After the reaction period, an indicator may be added to the cavity. The interaction of the indicator with the receptor-analyte may produce a detectable signal. A particle, which has not been exposed to the analyte may remain unchanged or show a different color change. In an embodiment, a staining or precipitation technique may be used to further visualize the indicator molecule. After a receptor-analyte-indicator complex is formed, a fluid containing a molecule that will react with the indicator portion of the complex may be added to the cavity to cause a signal change of the complex. A particle, which has not been exposed to the analyte may remain unchanged or show a different color change. Optionally, a wash to remove unbound indicator molecules may be performed before visualization of the receptor-analyte-indicator complex. Examples of indicators may be, but are not limited to, fluorescent dyes, enzyme-linked molecules and/or colloidal precious metal linked molecules.

The development of smart sensors capable of discriminating different analytes, toxins, and/or bacteria has become increasingly important for environmental, health and safety, remote sensing, military, and chemical processing applications. Although many sensors capable of high sensitivity and high selectivity detection have been fashioned for single analyte detection, only in a few selected cases have array sensors been prepared which display multi-analyte detection capabilities. The obvious advantages of such array systems are their utility for the analysis of multiple analytes and their ability to be "trained" to respond to new stimuli. Such on site adaptive analysis capabilities afforded by the array structures may make their utilization promising for a variety of future applications.

Single and multiple analyte sensors typically rely on changes in optical signals. These sensors may make use of an indicator that undergoes a perturbation upon analyte binding. The indicator may be a chromophore or a fluorophore. A fluorophore is a molecule that absorbs light at a characteristic wavelength and then re-emits the light at a characteristically different wavelength. Fluorophores include, but are not limited to, rhodamine and rhodamine derivatives, fluorescein and fluorescein derivatives, coumarins, and chelators with the lanthanide ion series. The emission spectra, absorption spectra, and chemical composition of many fluorophores may be found, e.g., in the "Handbook of Fluorescent Probes and Research Chemicals", R. P. Haugland, ed. which is incorporated herein by reference. A chromophore is a molecule which absorbs light at a characteristic wavelength, but does not re-emit light.

As previously described, the receptor itself may incorporate an indicator. The binding of the analyte to the receptor may directly lead to a modulation of the properties of the indicator. Such an approach typically requires a covalent attachment or strong non-covalent binding of the indicator onto or as part of the receptor, leading to additional covalent architecture. Every receptor may need a designed signaling protocol that is typically unique to that receptor. General protocols for designing signal modulation that is versatile for most any receptor would be desirable.

In one embodiment, a general method for the creation of optical signal modulations for most any receptor coupled to an immobilized matrix is developed. Immobilized matrices include, but are not limited to, resins, beads, and polymer surfaces. By immobilization of the receptor to the matrix, the receptor is held within a structure that can be chemically modified, allowing one to tune and to create an environment around the receptor that is sensitive to analyte binding. Coupling of the indicator to an immobilization matrix may make it sensitive to microenvironment changes, which foster signal modulation of the indicator upon analyte binding. Further, by coupling the indicator to an immobilization matrix, the matrix itself becomes the signaling unit, not requiring a specific new signaling protocol for every receptor immobilized on the matrix.

In an embodiment, a receptor for a particular analyte or class of analytes may be designed and created with the chemical handles appropriate for immobilization on and/or in the matrix. A number of such receptors have been described above. The receptors can be, but are not limited to, antibodies, aptamers, organic receptors, combinatorial libraries, enzymes, and imprinted polymers.

Signaling indicator molecules may be created or purchased which have appropriate chemical handles for immobilization on and/or in the immobilization matrix. The indicators may possess chromophores or fluorophores that are sensitive to their microenvironment. This chromophore or fluorophore may be sensitive to microenvironment changes that include, but are not limited to, sensitivity to local pH, solvatophobic or solvatophilic properties, ionic strength, dielectric, ion pairing, and/or hydrogen bonding. Common indicators, dyes, quantum particles, and semi-conductor particles, are all examples of possible probe molecules. The probe molecules may have epitopes similar to the analyte, so that a strong or weak association of the probe molecules with the receptor may occur. Alternatively, the probe molecules may be sensitive to a change in their microenvironment that results from one of the affects listed in item above.

Binding of the analyte may do one of the following things, resulting in a signal modulation: 1) displace a probe molecule from the binding site of the receptor, 2) alter the local pH, 3) change the local dielectric properties, 4) alter the features of the solvent, 5) change the fluorescence quantum yield of individual dyes, 6) alter the rate/efficiency of fluorescence resonance energy transfer (FRET) between donor-acceptor fluorophore pairs, or 7) change the hydrogen bonding or ion pairing near the probe.

In an alternative embodiment, two or more indicators may be attached to the matrix. Binding between the receptor and analyte causes a change in the communication between the indicators, again via either displacement of one or more indicators, or changes in the microenvironment around one or more indicators. The communication between the indicators may be, but is not limited to, fluorescence resonance energy transfer, quenching phenomenon, and/or direct binding.

In an embodiment, a particle for detecting an analyte may be composed of a polymeric resin. A receptor and an indicator may be coupled to the polymeric resin. The indicator and the receptor may be positioned on the polymeric resin such that the indicator produces a signal in when the analyte interacts with the receptor. The signal may be a change in absorbance (for chromophoric indicators) or a change in fluorescence (for fluorophoric indicators).

A variety of receptors may be used in one embodiment; the receptor may be a polynucleotide, a peptide, an oligosaccharide, an enzyme, a peptide mimetic, or a synthetic receptor. These receptors are described in U.S. patent application Ser. No. 10/072,800, which is incorporated by reference as if fully set forth herein.

A number of combinations for the coupling of an indicator and a receptor to a polymeric resin have been devised. These combinations are schematically depicted in FIG. 30. In one embodiment, depicted in FIG. 30A, receptor R may be coupled to a polymeric resin. The receptor may be directly formed on the polymeric resin, or be coupled to the polymeric resin via a linker. Indicator I may also be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of analyte A.

Figure 30A:
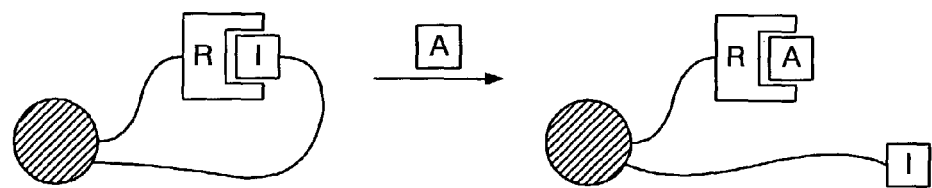
FIGS. 30A-I depict various sensing protocols for receptor-indicator-polymeric resin particles in an embodiment of a sensor array system.
Figure 30B:
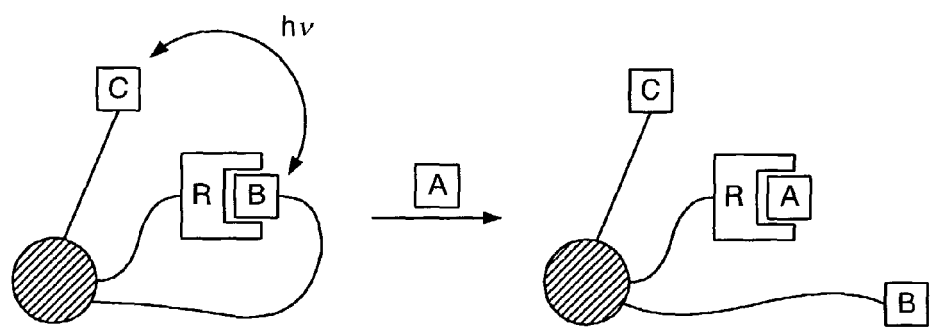

In another embodiment, depicted in FIG. 30B, receptor R may be coupled to a polymeric resin. The receptor may be directly formed on the polymeric resin, or be coupled to the polymeric resin via a linker. An indicator B may also be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of analyte A. An additional indicator C may also be coupled to the polymeric resin. The additional indicator may be directly coupled to the polymeric resin or coupled to the polymeric resin by a linker. In some embodiments, the additional indicator is coupled to the polymeric resin, such that the additional indicator is proximate the receptor during use.

Figure 30C:
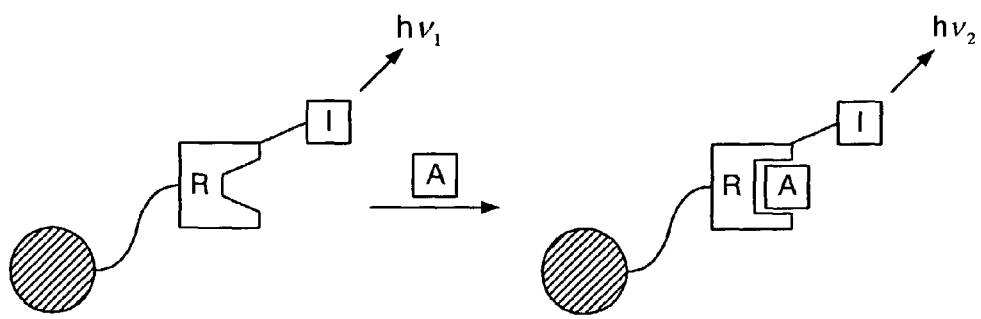

In another embodiment, depicted in FIG. 30C, receptor R may be coupled to a polymeric resin. The receptor may be directly formed on the polymeric resin, or be coupled to the polymeric resin via a linker. Indicator I may be coupled to the receptor. The indicator may be directly coupled to the receptor or coupled to the receptor by a linker. In some embodiments, the linker coupling the indicator to the polymeric resin is of sufficient length to allow the indicator to interact with the receptor in the absence of analyte A, as depicted in FIG. 30E.

Figure 30D:
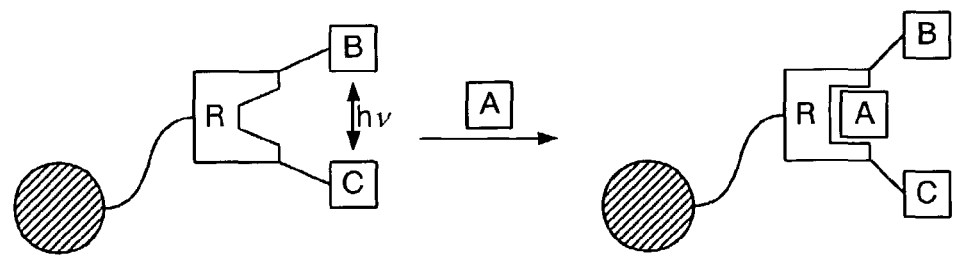
Figure 30E:
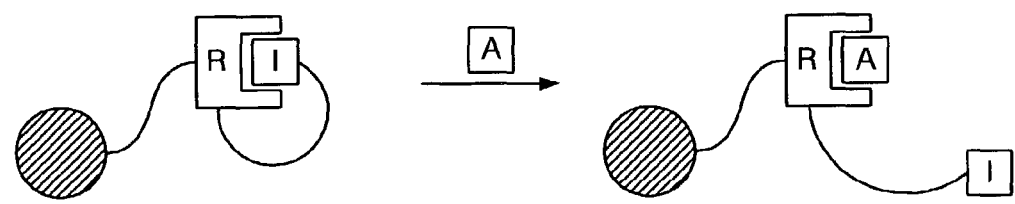
Figure 30F:
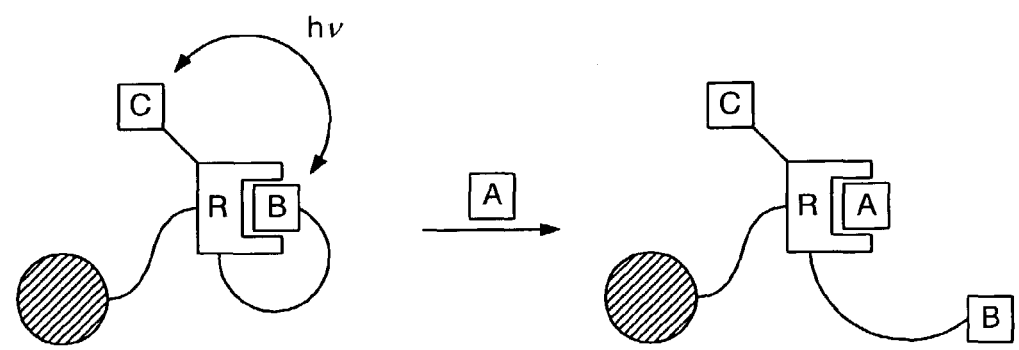

In another embodiment, depicted in FIG. 30D, receptor R may be coupled to a polymeric resin. The receptor may be directly formed on the polymeric resin, or be coupled to the polymeric resin via a linker. Indicator B may be coupled to the receptor. Indicator B may be directly coupled to the receptor or coupled to the receptor by a linker. In some embodiments, the linker coupling the indicator to the polymeric resin is of sufficient length to allow the indicator to interact with the receptor in the absence of analyte A. An additional indicator C may also be coupled to the receptor. The additional indicator may be directly coupled to the receptor or coupled to the receptor by a linker as depicted in FIG. 30F.

Figure 30G:
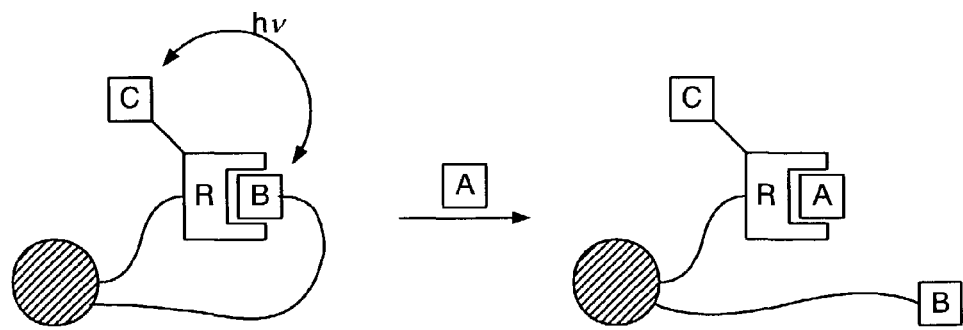

In another embodiment, depicted in FIG. 30G, receptor R may be coupled to a polymeric resin. The receptor may be directly formed on the polymeric resin, or be coupled to the polymeric resin via a linker. Indicator B may be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of analyte A. An additional indicator C may also be coupled to the receptor. The additional indicator may be directly coupled to the receptor or coupled to the receptor by a linker.

Figure 30H:
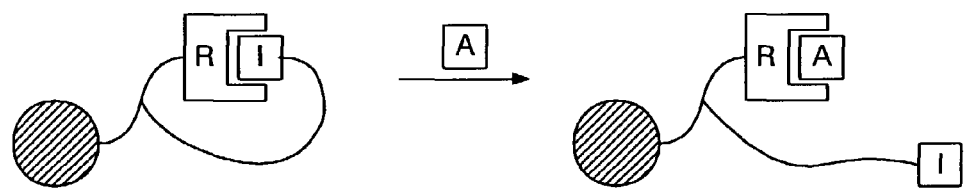

In another embodiment, depicted in FIG. 30H, receptor R may be coupled to a polymeric resin by a first linker. Indicator I may be coupled to the first linker. The indicator may be directly coupled to the first linker or coupled to the first linker by a second linker. In some embodiments, the second linker coupling the indicator to the polymeric resin is of sufficient length to allow the indicator to interact with the receptor in the absence of analyte A.

Figure 30I:
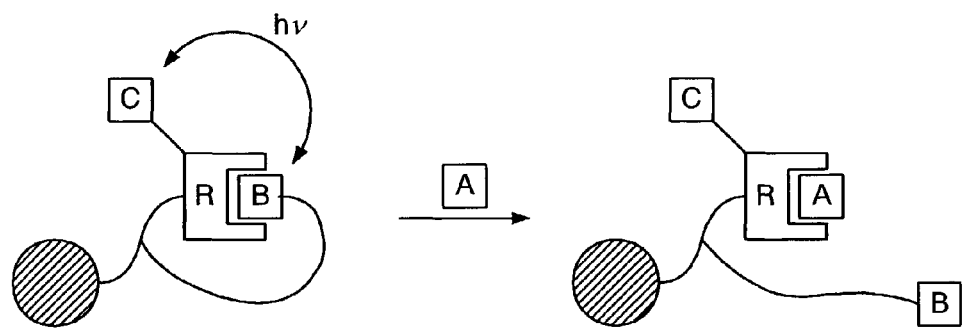

In another embodiment, depicted in FIG. 30I, a receptor R may be coupled to a polymeric resin by a first linker. An indicator B may be coupled to the first linker. The indicator may be directly coupled to the first linker or coupled to the first linker by a second linker. In some embodiments, the second linker coupling the indicator to the first linker is of sufficient length to allow the indicator to interact with the receptor in the absence of analyte A. An additional indicator C may be coupled to the receptor. The additional indicator may be directly coupled to the receptor or coupled to the receptor by a linker.

These various combinations of receptors, indicators, linkers and polymeric resins may be used in a variety of different signaling protocols. Analyte-receptor interactions may be transduced into signals through one of several mechanisms. In one approach, the receptor site may be preloaded with an indicator, which can be displaced in a competition with analyte ligand. In this case, the resultant signal is observed as a decrease in a signal produced by the indicator. This indicator may be a fluorophore or a chromophore. In the case of a fluorophore indicator, the presence of an analyte may be determined by a decrease in the fluorescence of the particle.

In the case of a chromophore indicator, the presence of an analyte may be determined by a decrease in the absorbance of the particle.

A second approach that has the potential to provide better sensitivity and response kinetics is the use of an indicator as a monomer in the combinatorial sequences (such as either structure shown in FIG. 14), and to select for receptors in which the indicator functions in the binding of ligand. Hydrogen bonding or ionic substituents on the indicator involved in analyte binding may have the capacity to change the electron density and/or rigidity of the indicator, thereby changing observable spectroscopic properties such as fluorescence quantum yield, maximum excitation wavelength, maximum emission wavelength, and/or absorbance. This approach may not require the dissociation of a preloaded fluorescent ligand (limited in response time by koff), and may modulate the signal from essentially zero without analyte to large levels in the presence of analyte.

In one embodiment, the microenvironment at the surface and interior of the resin beads may be conveniently monitored using spectroscopy when simple pH sensitive dyes or solvachromic dyes are imbedded in the beads. As a guest binds, the local pH and dielectric constants of the beads change, and the dyes respond in a predictable fashion. The binding of large analytes with high charge and hydrophobic surfaces, such as DNA, proteins, and steroids, should induce large changes in local microenvironment, thus leading to large and reproducible spectral changes. This means that most any receptor can be attached to a resin bead that already has a dye attached, and that the bead becomes a sensor for the particular analyte.

In one embodiment, a receptor may be covalently coupled to an indicator. The binding of the analyte may perturb the local microenvironment around the receptor leading to a modulation of the absorbance or fluorescence properties of the sensor.

In one embodiment, receptors may be used immediately in a sensing mode simply by attaching the receptors to a bead that is already derivatized with a dye sensitive to its microenvironment. This is offers an advantage over other signaling methods because the signaling protocol becomes routine and does not have to be engineered; only the receptors need to be engineered. The ability to use several different dyes with the same receptor, and the ability to have more than one dye on each bead allows flexibility in the design of a sensing particle.

Changes in the local pH, local dielectric, or ionic strength, near a fluorophore may result in a signal. A high positive charge in a microenvironment leads to an increased pH since hydronium migrates away from the positive region. Conversely, local negative charge decreases the microenvironment pH. Both changes result in a difference in the protonation state of pH sensitive indicators present in that microenvironment. Many common chromophores and fluorophores are pH sensitive. The interior of the bead may be acting much like the interior of a cell, where the indicators should be sensitive to local pH.

Figure 31:
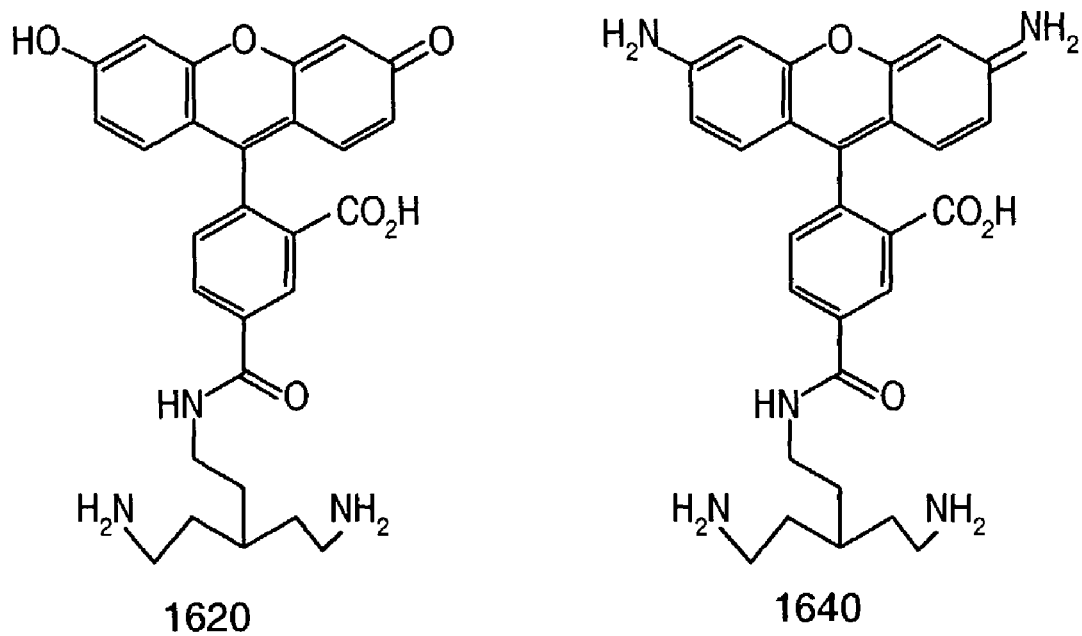
FIG. 31 depicts receptors in an embodiment of a sensor array system.
Figure 32:
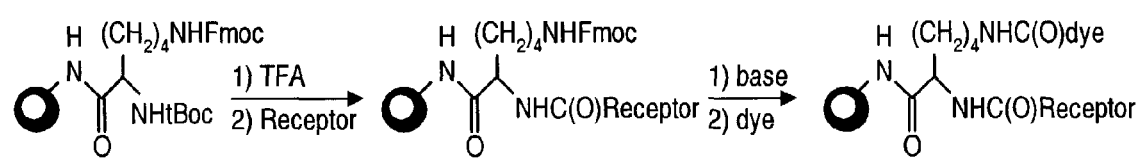
FIG. 32 depicts the attachment of differentially protected lysine to a bead in an embodiment of a sensor array system.

The third optical transduction scheme involves fluorescence energy transfer. In this approach, two fluorescent monomers for signaling may be mixed into a combinatorial split synthesis. Examples of these monomers are depicted in FIG. 31. Compound 1620 (a derivative of fluorescein) contains a common colorimetric/fluorescent probe that may be mixed into the oligomers as the reagent that will send out a modulated signal upon analyte binding. The modulation may be due to resonance energy transfer to monomer 1640 (a derivative of rhodamine).

When an analyte binds to the receptor, structural changes in the receptor will alter the distance between the monomers (schematically depicted in FIG. 29, 1460 corresponds to monomer 1620 and 1480 corresponds to monomer 1640). It is well known that excitation of fluorescein may result in emission from rhodamine when these molecules are oriented correctly. The efficiency of resonance energy transfer from fluorescein to rhodamine will depend strongly upon the presence of analyte binding; thus, measurement of rhodamine fluorescence intensity (at a substantially longer wavelength than fluorescein fluorescence) will serve as an indicator of analyte binding. To greatly improve the likelihood of a modulatory fluorescein-rhodamine interaction, multiple rhodamine tags can be attached at different sites along a combinatorial chain without substantially increasing background rhodamine fluorescence (only rhodamine very close to fluorescein will yield appreciable signal). In one embodiment, depicted in FIG. 29, when no ligand is present, short wavelength excitation light (blue light) excites the fluorophore 1460, which fluoresces (green light). After binding of analyte ligand to the receptor, a structural change in the receptor molecule brings fluorophore 1460 and fluorophore 1480 in proximity, allowing excited-state fluorophore 1460 to transfer its energy to fluorophore 1480. This process, fluorescence resonance energy transfer, is extremely sensitive to small changes in the distance between dye molecules (e.g., efficiency ~[distance]$^{-6}$).

In another embodiment, photoinduced electron transfer (PET) may be used to analyze the local microenvironment around the receptor. The methods generally include a fluorescent dye and a fluorescence quencher. A fluorescence quencher is a molecule that absorbs the emitted radiation from a fluorescent molecule. The fluorescent dye, in its excited state, will typically absorbs light at a characteristic wavelength and then re-emits the light at a characteristically different wavelength. The emitted light, however, may be reduced by electron transfer with the fluorescent quencher, which results in quenching of the fluorescence. Therefore, if the presence of an analyte perturbs the quenching properties of the fluorescence quencher, a modulation of the fluorescent dye may be observed.

The above-described signaling methods may be incorporated into a variety of receptorindicator-polymeric resin systems. Turning to FIG. 30A, an indicator I and receptor R may be coupled to a polymeric resin. In the absence of an analyte, the indicator may produce a signal in accordance with the local microenvironment. The signal may be an absorbance at a specific wavelength or fluorescence. When the receptor interacts with an analyte, the local microenvironment may be altered such that the produced signal is altered. In one embodiment, depicted in FIG. 30A, the indicator may partially bind to the receptor in the absence of analyte A. When the analyte is present, the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, depicted in Turning to FIG. 30C, indicator I may be coupled to receptor R. The receptor may be coupled to a polymeric resin. In the absence of analyte A, the indicator may produce a signal in accordance with the local microenvironment. The signal may be an absorbance at a specific wavelength or fluorescence. When the receptor interacts with an analyte, the local microenvironment may be altered such that the produced signal is altered. In contrast to the case depicted in FIG. 30A, the change in local microenvironment may be due to a conformation change of the receptor due to the biding of the analyte. Such a change in environment may induce a change in the absorbance or fluorescence of the indicator.

In another embodiment, depicted in FIG. 30E, indicator I may be coupled to a receptor by a linker. The linker may have a sufficient length to allow the indicator to bind to the receptor in the absence of analyte A. Receptor R may be coupled to a polymeric resin. In the absence of analyte A, the indicator may produce a signal in accordance with the local microenvironment. As depicted in FIG. 30E, the indicator may partially bind to the receptor in the absence of an analyte. When the analyte is present, the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, depicted in FIG. 30H, receptor R may be coupled to a polymeric resin by a first linker. An indicator may be coupled to the first linker. In the absence of analyte A, the indicator may produce a signal in accordance with the local microenvironment. The signal may be an absorbance at a specific wavelength or fluorescence. When the receptor interacts with an analyte, the local microenvironment may be altered such that the produced signal is altered. In one embodiment, as depicted in FIG. 30H, the indicator may partially bind to the receptor in the absence of an analyte. When the analyte is present, the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, the use of fluorescence resonance energy transfer or photoinduced electron transfer may be used to detect the presence of an analyte. Both of these methodologies involve the use of two fluorescent molecules. Turning to FIG. 30B, a first fluorescent indicator B may be coupled to receptor R. Receptor R may be coupled to a polymeric resin. A second fluorescent indicator C may also be coupled to the polymeric resin. In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or the second fluorescent indicator may be a fluorescence quencher.

When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects will reverse if the presence of an analyte causes the indicators to move closer to each other.

In another embodiment, depicted in FIG. 30D, a first fluorescent indicator B may be coupled to receptor R. A second fluorescent indicator C may also be coupled to the receptor. Receptor R may be coupled to a polymeric resin. In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or the second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, depicted in FIG. 30D, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects would reverse if the presence of an analyte causes the indicators to move closer to each other.

In a similar embodiment to FIG. 30D, the first fluorescent indicator B and second fluorescent indicator C may be both coupled to receptor R, as depicted in FIG. 30F. Receptor R may be coupled to a polymeric resin. First fluorescent indicator B may be coupled to receptor R by a linker group. The linker group may allow the first indicator to bind the receptor, as depicted in FIG. 30F. In the absence of an analyte, the first and second fluorescent indicators may be positioned such that fluorescence energy transfer may occur. When the analyte is presence, the first indicator may be displaced from the receptor, causing the fluorescence energy transfer between the two indicators to be altered.

In another embodiment, depicted in FIG. 30G, first fluorescent indicator B may be coupled to a polymeric resin. Receptor R may also be coupled to a polymeric resin. A second fluorescent indicator C may be coupled to the receptor R. In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or the second fluorescent indicator may be a fluorescence quencher.

When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects would reverse if the presence of an analyte causes the indicators to move closer to each other.

In another embodiment, depicted in FIG. 30I, a receptor R may be coupled to a polymeric resin by a first linker. First fluorescent indicator B may be coupled to the first linker. Second fluorescent indicator C may be coupled to receptor R. In the absence of analyte A, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or the second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects would reverse if the presence of an analyte causes the indicators to move closer to each other.

In one embodiment, polystyrene/polyethylene glycol resin beads may be used as a polymeric resin since they are highly water permeable, and give fast response times to penetration by analytes. The beads may be obtained in sizes ranging from 5 microns to 250 microns. Analysis with a confocal microscope reveals that these beads are segregated into polystyrene and polyethylene glycol microdomains, at about a 1 to 1 ratio. Using the volume of the beads and the reported loading of 300pmol/bead, we can calculate an average distance of 35 Å between terminal sites. This distance is well within the Forester radii for the fluorescent dyes that we are proposing to use in our fluorescence resonance energy transfer ("FRET") based signaling approaches. This distance is also reasonable for communication between binding events and microenvironment changes around the fluorophores.

Figure 33:
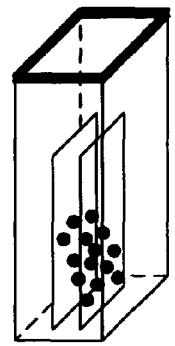
FIG. 33 depicts a system for measuring the absorbance or emission of a sensing particle.

The derivatization of the beads with receptors and indicators may be accomplished by coupling carboxylic acids and amines using EDC and HOBT. Typically, the efficiency of couplings are greater that 90% using quantitative ninhydrin tests. (See Niikura, K.; Metzger, A.; and Anslyn, E. V. "A Sensing Ensemble with Selectivity for Jositol Trisphosphate", *J. Am. Chem. Soc*. 1998, 120, 0000, which is incorporated herein by reference). The level of derivatization of the beads is sufficient to allow the loading of a high enough level of indicators and receptors to yield successful assays. However, an even higher level of loading may be advantageous since it would increase the multi-valency effect for binding analytes within the interior of the beads. We may increase the loading level two fold and ensure that two amines are close in proximity by attaching an equivalent of lysine to the beads (see FIG. 33). The amines may be kept in proximity so that binding of an analyte to the receptor will influence the environment of a proximal indicator.

Even though a completely random attachment of indicator and a receptor lead to an effective sensing particle, it may be better to rationally place the indicator and receptor in proximity. In one embodiment, lysine that has different protecting groups on the two different amines may be used, allowing the sequential attachment of an indicator and a receptor. If needed, additional rounds of derivatization of the beads with lysine may increase the loading by powers of two, similar to the synthesis of the first few generations of dendrimers.

In contrast, too high a loading of fluorophores will lead to self-quenching, and the emission signals may actually decrease with higher loadings. If self-quenching occurs for fluorophores on the commercially available beads, the terminal amines may be incrementally capped, thereby incrementally lowering loading of the indicators.

Moreover, there should be an optimum ratio of receptors to indicators. The optimum ratio is defined as the ratio of indicator to receptor to give the highest response level. Too few indicators compared to receptors may lead to little change in spectroscopy since there will be many receptors that are not in proximity to indicators. Too many indicators relative to receptors may also lead to little change in spectroscopy since many of the indicators will not be near receptors, and hence a large number of the indicators will not experience a change in microenvironment. Through iterative testing, the optimum ratio may be determined for any receptor indicator system.

This iterative sequence will be discussed in detail for a particle designed to signal the presence of an analyte in a fluid. The sequence begins with the synthesis of several beads with different loadings of the receptor. The loading of any receptor may be quantitated using the ninhydrin test. (The ninhydrin test is described in detail in Kaiser, E.; Colescott, R. L.; Bossinger, C. D.; Cook, P. I. "Color Test for Detection of Free Terminal Amino Groups in the Solid-Phase Synthesis of Peptides", *Anal. Biochem*. 1970, 34, 595-598, which is incorporated herein by reference). The number of free amines on the bead is measured prior to and after derivatization with the receptor, the difference of which gives the loading. Next, the beads undergo a similar analysis with varying levels of molecular probes. The indicator loading may be quantitated by taking the absorption spectra of the beads. In this manner, the absolute loading level and the ratio between the receptor and indicators may be adjusted. Creating calibration curves for the analyte using the different beads will allow the optimum ratios to be determined.

Figure 34:
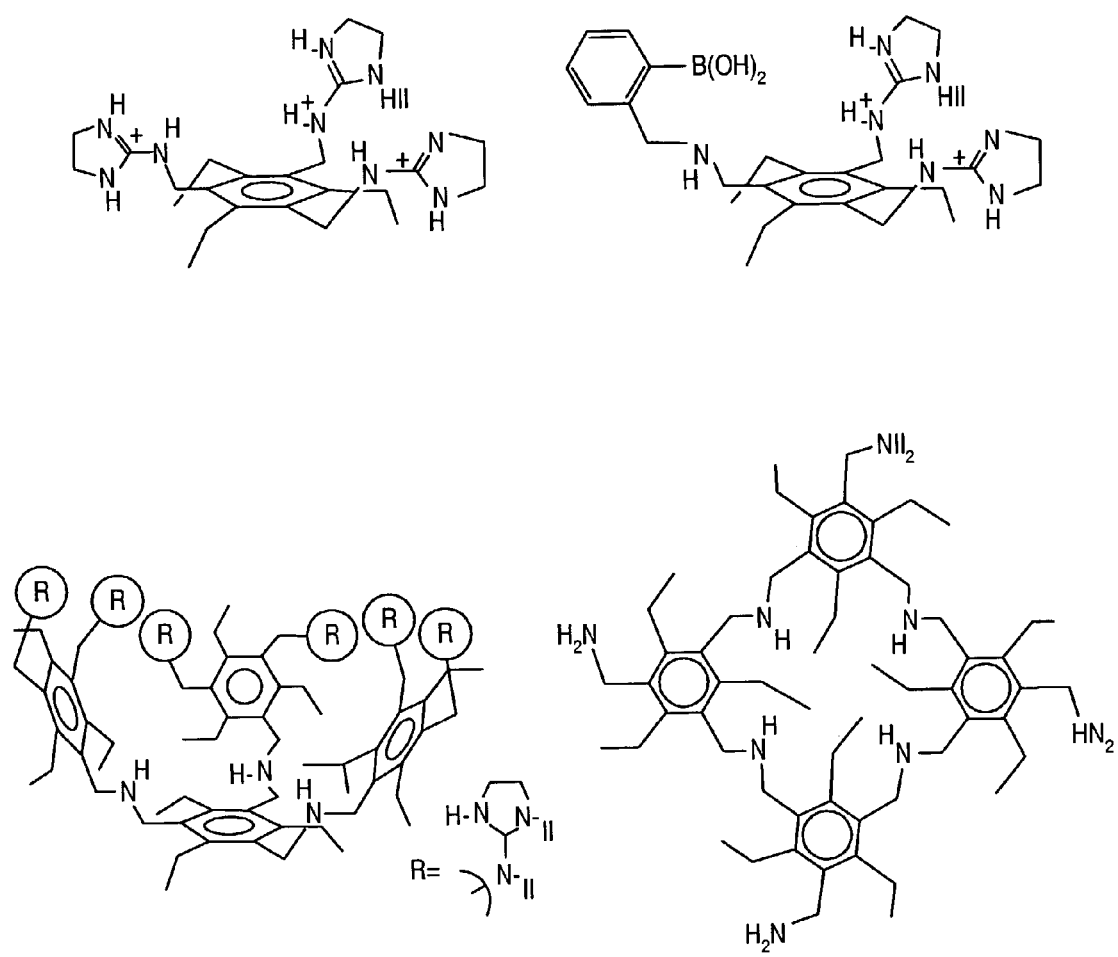
FIG. 34 depicts receptors in an embodiment of a sensor array system; system.

The indicator loading may be quantitated by taking the absorption spectra of a monolayer of the beads using our sandwich technique (See FIG. 34). The sandwich technique involves measuring the spectroscopy of single monolayers of the beads. The beads may be sandwiched between two cover slips and gently rubbed together until a monolayer of the beads is formed. One cover slip is removed and meshed with dimensions on the order of the beads is then place over the beads, and the cover slip replaced. This sandwich is then placed within a cuvette, and the absorbance or emission spectra are recorded. Alternatively, a sensor array system, as described above, may be used to analyze the interaction of the beads with the analyte.

Figure 35:
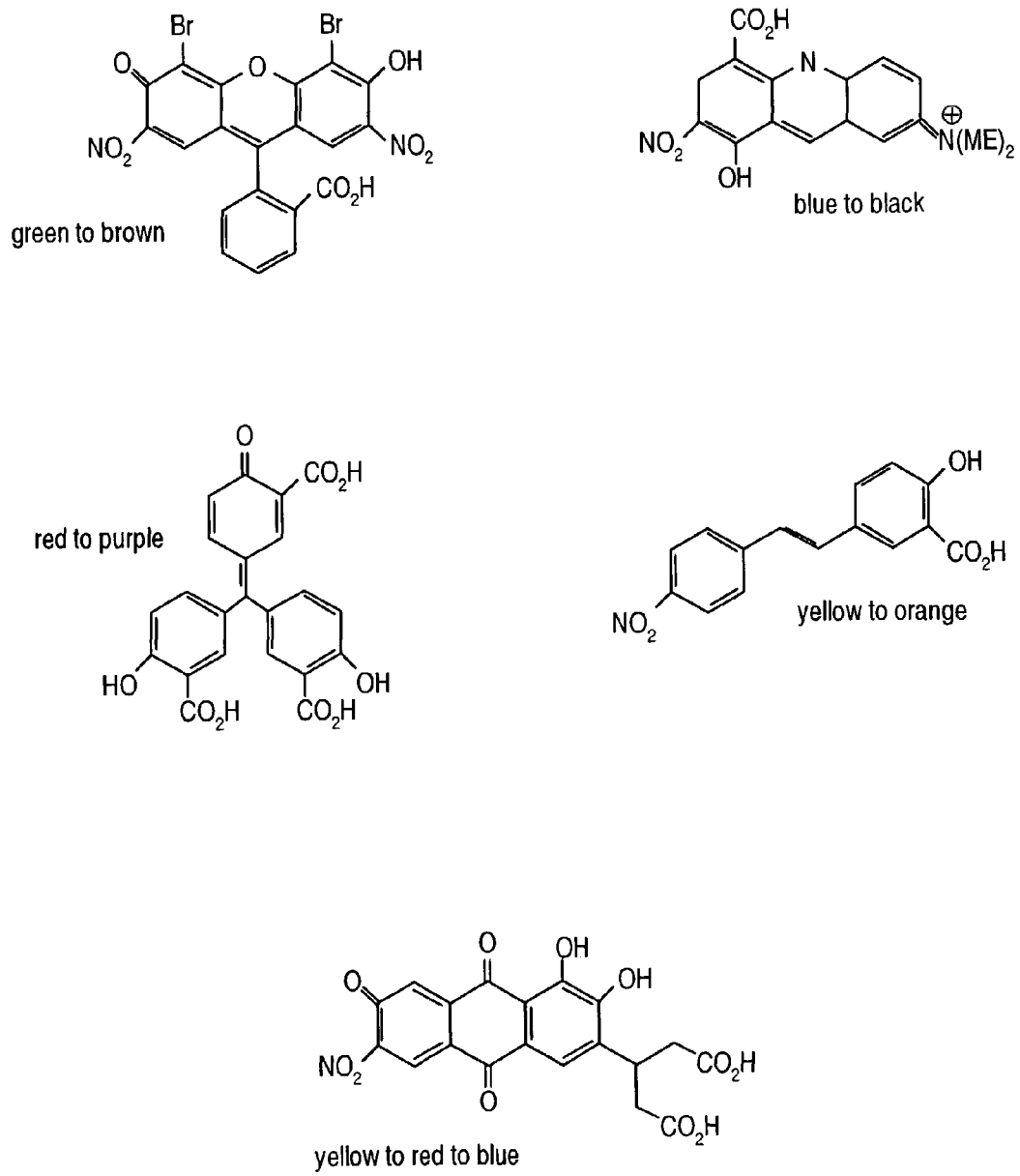
FIG. 35 depicts pH indicators, which may be coupled to a particle in an embodiment of a sensor array system.

A variety of receptors may be coupled to the polymeric beads. Many of these receptors have been previously described. Other receptors are shown in FIG. 35.

Figure 36:
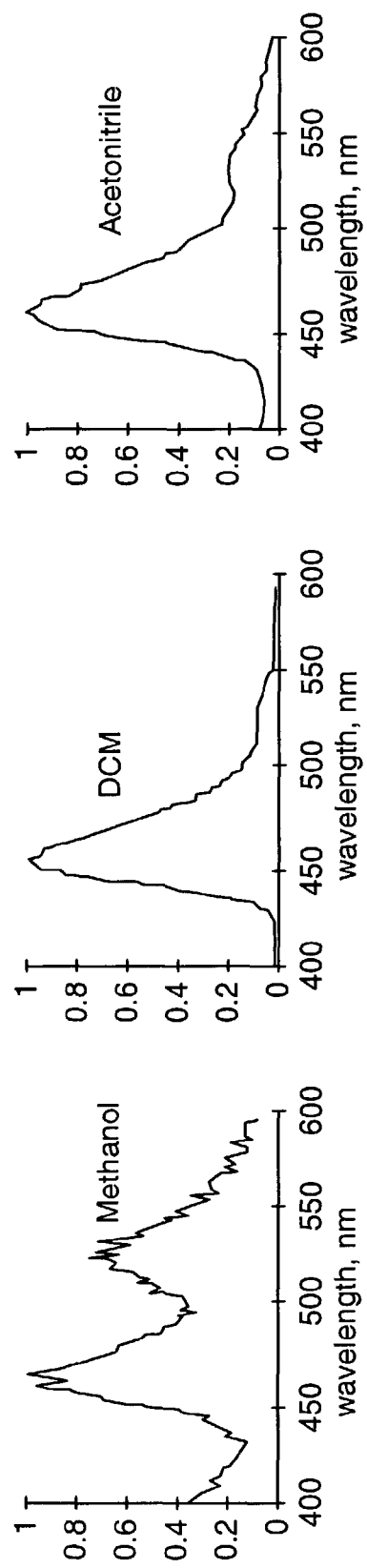
FIG. 36 depicts the change in FRET between coumarin and 5-carboxyfluorescein on resin beads as a function of the solvent in an embodiment of a sensor array system.

As described generally above, an ensemble may be formed by a synthetic receptor and a probe molecule, either mixed together in solution or bound together on a resin bead. The modulation of the spectroscopic properties of the probe molecule results from perturbation of the microenvironment of the probe, due to interaction of the receptor with the analyte; often a simple pH effect. The use of a probe molecule coupled to a common polymeric support may produce systems that give color changes upon analyte binding. A large number of dyes are commercially available, many of which may be attached to the bead via a simple EDC/HOBT coupling (FIG. 36 shows some examples of indicators). These indicators are sensitive to pH, and respond to ionic strength and solvent properties. When contacted with an analyte, the receptor interacts with the analyte such that microenvironment of the polymeric resin may become significantly changed. This change in the microenvironment may induce a color change in the probe molecule. This may lead to an overall change in the appearance of the particle indicating the presence of the analyte.

Since many indicators are sensitive to pH and local ionic strength, index of refraction, and/or metal binding, lowering the local dielectric constant near the indicators may modulate the activity of the indicators such that they are more responsive. A high positive charge in a microenvironment leads to an increased pH since hydronium ions migrate away from the positive region. Conversely, local negative charge decreases the microenvironment pH. Both changes result in a difference on the protonation state of a pH sensitive indicator present in that microenvironment. The altering of the local dielectric environment may be produced by attaching molecules of differing dielectric constants to the bead proximate to the probe molecules. Examples of molecules, which may be used to alter the local dielectric environment include, but are not limited to, planar aromatics, long chain fatty acids, and oligomeric tracts of phenylalanine, tyrosine, and tryptophan. Differing percentages of these compounds may be attached to the polymeric bead to alter the local dielectric constant.

Competition assays may also be used to produce a signal to indicate the presence of an analyte. The high specificity of antibodies makes them the current tools of choice for the sensing and quantitation of structurally complex molecules in a mixture of analytes. These assays rely on a competition approach in which the analyte is tagged and bound to the antibody. Addition of the untagged analyte results in a release of the tagged analytes and spectroscopic modulation is monitored. Surprisingly, although competition assays have been routinely used to determine binding constants with synthetic receptors, very little work has been done exploiting competition methods for the development of sensors based upon synthetic receptors. Examples of the competitive assay is described in U.S. patent application Ser. No. 10/072,800 which is fully incorporated by reference as if fully set forth herein.

Dramatic spectroscopy changes accompany the chelation of metals to ligands that have chromophores. In fact, most colorimetric/fluorescent sensors for metals rely upon such a strategy. Binding of the metal to the inner sphere of the ligand leads to ligand/metal charge transfer bands in the absorbance spectra, and changes in the HOMO-LUMO gap that leads to fluorescence modulations. Examples of spectroscopy changes from the chelation of metals to ligands is described in U.S. patent application Ser. No. 10/072,800 which is fully incorporated by reference as if fully set forth herein.

In one embodiment, an indicator may be coupled to a bead and further may be bound to a receptor that is also coupled to the bead. Displacement of the indicator by an analyte will lead to signal modulation. Such a system may also take advantage of fluorescent resonance energy transfer to produce a signal in the presence of an analyte. Fluorescence resonance energy transfer is a technique that can be used to shift the wavelength of emission from one position to another in fluorescence spectra. In the manner it creates, a much more sensitive assay since one can monitor intensity at two wavelengths. The method involves the radiationless transfer of excitation energy from one fluorophore to another. The transfer occurs via coupling of the oscillating dipoles of the donor with the transition dipole of the acceptor. The efficiency of the transfer is described by equations first derived by Forester. They involve a distance factor R, orientation factor k, solvent index of refraction N, and spectral overlap J.

In order to incorporate fluorescence resonance energy transfer into a particle a receptor and two different indicators may be incorporated onto a polymeric bead. In the absence of an analyte the fluorescence resonance energy transfer may occur giving rise to a detectable signal. When an analyte interacts with a receptor, the spacing between the indicators may be altered. Altering this spacing may cause a change in the fluorescence resonance energy transfer, and thus, a change in the intensity or wavelength of the signal produced. The fluorescence resonance energy transfer efficiency is proportional to the distance R between the two indicators by $1/R^6$. Thus, slight changes in the distance between the two indicators may induce significant changes in the fluorescence resonance energy transfer.

In one embodiment, various levels of coumarin and fluorescein may be loaded onto resin beads to achieve gradations in FRET levels from zero to 100%. FIG. 37 shows a 70/30 ratio of emission from 5-carboxyfluorescein and coumarin upon excitation of coumarin only in water. However, other solvents give dramatically different extents of FRET. This shows that the changes in the interior of the beads do lead to a spectroscopic response. This data also shows that differential association of the various solvents and 5-carboxyfluorescein on resin beads as a function of solvents. This behavior is evoked from the solvent association with the polymer itself, in the absence of purposefully added receptors. We may also add receptors, which exhibit strong/selective association with strategic analytes. Such receptors may induce a modulation in the ratio of FRET upon analyte binding, within the microenvironment of the polystyrene/polyethylene glycol matrices.

In order to incorporate a wavelength shift into fluorescence assays, receptors 3-6 may be coupled to the courmarin/5-carboxyfluorescein beads previously discussed. When 5-carboxyfluorescein is bound to the various receptors and coumarin is excited, the emission will be primarily form coumarin since the fluorescein will be bound to the receptors. Upon displacement of the 5-carboxyfluorescein by the analytes, emission should shift more toward 5-carboxyfluorescein since it will be released to the bead environment, which possesses coumarin. This will give us a wavelength shift in the fluorescence, which is inherently more sensitive than the modulation of intensity at a signal wavelength.

There should be large changes in the distance between indicators R on the resin beads. When the 5-carboxyfluorescein is bound, the donor/acceptor pair should be farther than when displacement takes place; the FRET efficiency scales as $1/R^6$. The coumarin may be coupled to the beads via a floppy linker, allowing it to adopt many conformations with respect to a bound 5-carboxyfluorescein. Hence, it is highly unlikely that the transition dipoles of the donor and acceptor will be rigorously orthogonal.

Detection of polycarboxylic acids, tartrate, tetracycline arino acids, solvatochromic dyes, and ATP using fluorophores are described in U.S. patent application Ser. No. 10/072,800, which is in incorporated by reference as if fully set forth herein.

As described above, a particle, in some embodiments, possesses both the ability to interact with the analyte of interest and to create a modulated signal. In one embodiment, the particle may include receptor molecules, which undergo a chemical change in the presence of the analyte of interest. This chemical change may cause a modulation in the signal produced by the particle. Chemical changes may include chemical reactions between the analyte and the receptor. Receptors may include biopolymers or organic molecules. Such chemical reactions may include, but are not limited to, cleavage reactions, oxidations, reductions, addition reactions, substitution reactions, elimination reactions, and radical reactions.

In one embodiment, the mode of action of the analyte on specific biopolymers may be taken advantage of to produce an analyte detection system. As used herein biopolymers refers to natural and unnatural: peptides, proteins, polynucleotides, and oligosaccharides. In some instances, analytes, such as toxins and enzymes, will react with biopolymer such that cleavage of the biopolymer occurs. In one embodiment, this cleavage of the biopolymer may be used to produce a detectable signal. A particle may include a biopolymer and an indicator coupled to the biopolymer. In the presence of the analyte, the biopolymer may be cleaved such that the portion of the biopolymer, which includes the indicator, may be cleaved from the particle. The signal produced from the indicator is then displaced from the particle. The signal of the bead will therefore change thus indicating the presence of a specific analyte.

Proteases represent a number of families of proteolytic enzymes that catalytically hydrolyze peptide bonds. Principal groups of proteases include metalloproteases, serine porteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and may be characterized by alterations in the activity of specific proteases and their inhibitors. For example, emphysema, arthritis, thrombosis, cancer metastasis and some forms of hemophilia result from the lack of regulation of serine protease activities. In case of viral infection, the presence of viral proteases has been identified in infected cells. Such viral proteases include, for example, HIV protease associated with AIDS and NS3 protease associated with Hepatitis C. Proteases have also been implicated in cancer metastasis. For example, the increased presence of the protease urokinase has been correlated with an increased ability to metastasize in many cancers. Examples of detection of proteases is described in U.S. patent application Ser. No. 10/072,800, which is incorporated by reference as if fully set forth herein.

Figure 37A:
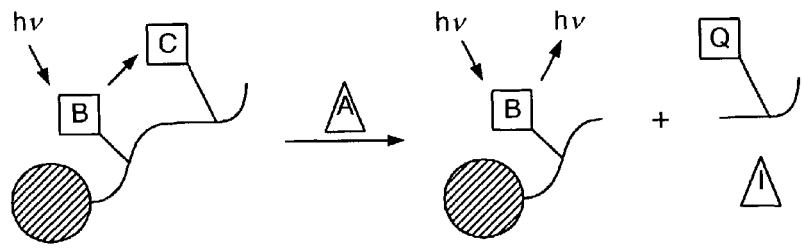
FIGS. 37A-D depict various sensing protocols for receptor-indicator-polymeric resin particles in which a cleavage reaction occurs in an embodiment of a sensor array system.

A variety of signaling mechanisms for the above described cleavage reactions may be used. In an embodiment, a fluorescent dye and a fluorescence quencher may be coupled to the biopolymer on opposite sides of the cleavage site. The fluorescent dye and the fluorescence quencher may be positioned within the Forster energy transfer radius. The Forster energy transfer radius is defined as the maximum distance between two molecules in which at least a portion of the fluorescence energy emitted from one of the molecules is quenched by the other molecule. Forster energy transfer has been described above. Before cleavage, little or no fluorescence may be generated by virtue of the molecular quencher. After cleavage, the dye and quencher are no longer maintained in proximity of one another, and fluorescence may be detected (FIG. 37A). The use of fluorescence quenching is described in U.S. Pat. No. 6,037,137, which is incorporated herein by reference. Further examples of this energy transfer are described in the following papers, all of which are incorporated herein by reference: James, T. D.; Samandumara, K. R. A.; Iguchi, R.; Shinkai, S. *J. Am. Chem. Soc.* 1995, 117, 8982. Murukami, H.; Nagasaki, T.; Hamachi, I.; Shinkai, S. *Tetrahedron Lett.*, 34, 6273. Shinkai, S.; Tsukagohsi, K.; Ishikawa, Y.; Kunitake, T. *J. Chem. Soc. Chem. Commun.* 1991, 1039. Kondo, K.; Shiomi, Y.; Saisho, M.; Harada, T.; Shinkai, S. *Tetrahedron.* 1992, 48, 8239. Shiomi, Y.; Kondo, K.; Saisho, M.; Harada, T.; Tsukagoshi, K.; Shinkai, S. *Supramol. Chem.* 1993, 2, 11. Shiomi, Y.; Saisho, M.; Tsukagoshi, K.; Shinkai, S. *J. Chem. Soc. Perkin Trans* 1 1993, 2111. Deng, G.; James, T. D.; Shinkai, S. *J. Am. Chem. Soc.* 1994, 116, 4567. James, T. D.; Harada, T.; Shinkai, S. *J. Chem. Soc. Chem. Commun.* 1993, 857. James, T. D.; Murata, K.; Harada, T.; Ueda, K.; Shinkai, S. *Chem. Lett.* 1994, 273. Ludwig, R.; Harada, T.; Ueda, K.; James, T. D.; Shinkai, S. *J. Chem. Soc. Perkin Trans* 2. 1994, 4, 497. Sandanayake, K. R. A. S.; Shinkai, S. *J. Chem. Soc., Chem. Commun.* 1994, 1083. Nagasaki, T.; Shinmori, H.; Shinkai, S. *Tetrahedron Lett.* 1994, 2201. Murakami, H.; Nagasaki, T.; Hamachi, I.; Shinkai, S. *J. Chem. Soc. Perkin Trans* 2. 1994, 975. Nakashima, K.; Shinkai, S. *Chem. Lett.* 1994, 1267. Sandanayake, K. R. A. S.; Nakashima, K.; Shinkai, S. *J. Chem. Soc.* 1994, 1621. James, T. D.; Sandanayake, K. R. A. S.; Shinkai, S. *J. Chem. Soc., Chem. Commun.* 1994, 477. James, T. D.; Sandanayake, K. R. A. S.; *Angew. Chem., Int. Ed. Eng.* 1994, 33, 2207. James, T. D.; Sandanayake, K. R. A. S.; Shinkai, S. *Nature*, 1995, 374, 345.

The fluorophores may be linked to the peptide receptor by any of a number of means well known to those of skill in the art. In an embodiment, the fluorophore may be linked directly from a reactive site on the fluorophore to a reactive group on the peptide such as a terminal amino or carboxyl group, or to a reactive group on an amino acid side chain such as a sulfur, an amino, a hydroxyl, or a carboxyl moiety. Many fluorophores normally contain suitable reactive sites. Alternatively, the fluorophores may be derivatized to provide reactive sites for linkage to another molecule. Fluorophores derivatized with functional groups for coupling to a second molecule are commercially available from a variety of manufacturers. The derivatization may be by a simple substitution of a group on the fluorophore itself, or may be by conjugation to a linker. Various linkers are well known to those of skill in the art and are discussed below.

The fluorogenic protease indicators may be linked to a solid support directly through the fluorophores or through the peptide backbone comprising the indicator. In embodiments where the indicator is linked to the solid support through the peptide backbone, the peptide backbone may comprise an additional peptide spacer. The spacer may be present at either the amino or carboxyl terminus of the peptide backbone and may vary from about 1 to about 50 amino acids, preferably from 1 to about 20 and more preferably from 1 to about 10 amino acids in length. The amino acid composition of the peptide spacer is not critical as the spacer just serves to separate the active components of the molecule from the substrate thereby preventing undesired interactions. However, the amino acid composition of the spacer may be selected to provide amino acids (e.g. a cysteine or a lysine) having side chains to which a linker or the solid support itself, is easily coupled. Alternatively, the linker or the solid support itself may be attached to the amino terminus of or the carboxyl terminus.

In an embodiment, the peptide spacer may be joined to the solid support by a linker. The term "linker", as used herein, refers to a molecule that may be used to link a peptide to another molecule, (e.g. a solid support, fluorophore, etc.). A linker is a hetero or homobifunctional molecule that provides a first reactive site capable of forming a covalent linkage with the peptide and a second reactive site capable of forming a covalent linkage with a reactive group on the solid support. Linkers as use din these embodiments are the same as the previously described linkers.

Figure 37B:
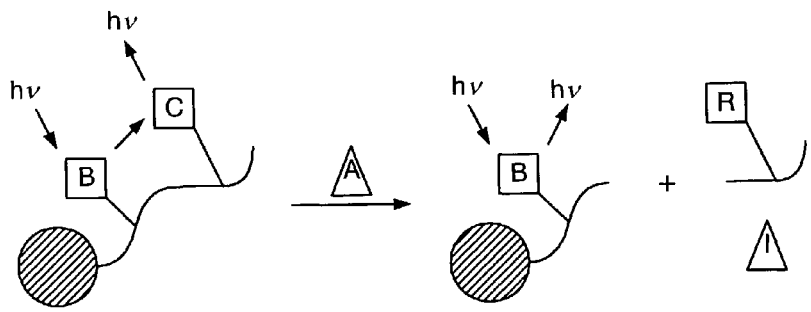

In an embodiment, a first fluorescent dye and a second fluorescent dye may be coupled to the biopolymer on opposite sides of the cleavage site. Before cleavage, a FRET (fluorescence resonance energy transfer) signal may be observed as a long wavelength emission. After cleavage, the change in the relative positions of the two dyes may cause a loss of the FRET signal and an increase in fluorescence from the shorter-wavelength dye (FIG. 37B). Examples of solution phase FRET have been described in Förster, Th. "Transfer Mechanisms of Electronic Excitation:, *Discuss. Faraday Soc.*, 1959, 27, 7; Khanna, P. L., Ullman, E. F. "4',5'-Dimethoxyl6-carboxyfluorescein: A novel dipole-dipole coupled fluorescence energy transfer acceptor useful for fluorescence immunoassays", *Anal. Biochem.* 1980, 108, 156; and Morrison, L. E. "Time resolved Detection of Energy Transfer: Theory and Application to Immunoassays", *Anal. Biochem.* 1998, 174, 101, all of which are incorporated herein by reference.

Figure 37C:
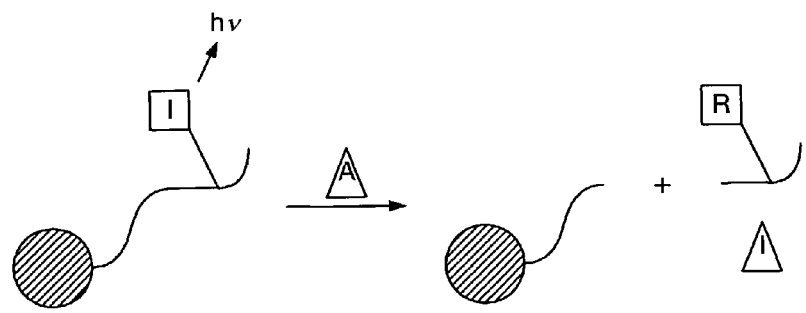
Figure 37D:
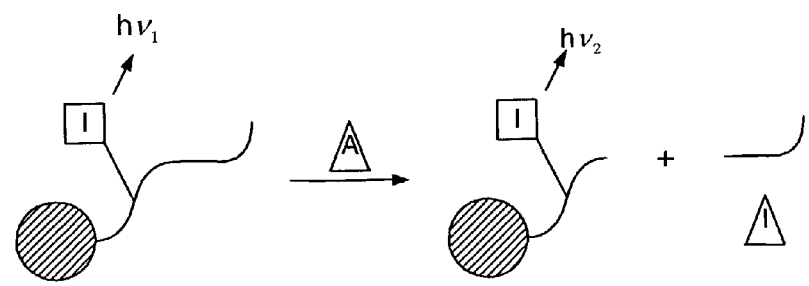

In another embodiment, a single fluorescent dye may be coupled to the peptide on the opposite side of the cleavage site to the polymeric resin. Before cleavage, the dye is fluorescent, but is spatially confined to the attachment site. After cleavage, the peptide fragment containing the dye may diffuse from the attachment site (e.g., to positions elsewhere in the cavity) where it may be measured with a spatially sensitive detection approach, such as confocal microscopy (FIG. 37C). Alternatively, the solution in the cavities may be flushed from the system. A reduction in the fluorescence of the particle would indicate the presence of the analyte (e.g., a protease).

In another embodiment, a single indicator (e.g., a chromophore or a fluorophore) may be coupled to the peptide receptor on the side of the cleavage site that remains on the polymeric resin or to the polymeric resin at a location proximate to the receptor. Before cleavage, the indicator may produce a signal that reflects the microenvironment determined by the interaction of the receptor with the indicator. Hydrogen bonding or ionic substituents on the indicator involved in analyte binding have the capacity to change the electron density and/or rigidity of the indicator, thereby changing observable spectroscopic properties such as fluorescence quantum yield, maximum excitation wavelength, or maximum emission wavelength for fluorophores or absorption spectra for chromophores. When the peptide receptor is cleaved, the local pH and dielectric constants of the beads change, and the indicator may respond in a predictable fashion. An advantage to this approach is that it does not require the dissociation of a preloaded fluorescent ligand (limited in response time by koff). Furthermore, several different indicators may be used with the same receptor. Different beads may have the same receptors but different indicators, allowing for multiple testing for the presence of proteases. Alternatively, a single polymeric resin may include multiple dyes along with a single receptor. The interaction of each of these dyes with the receptor may be monitored to determine the presence of the analyte.

Diagnostic Use of a Sensor Array System To Detect Cardiovascular Risks

The previously described sensor array systems may be used in diagnostic testing. Examples of diagnostic testing are described in U.S. patent application Ser No. 10/072,800 which is fully incorporated herein by reference as if set forth herein.

In many common diagnostic tests, antibodies may be used to generate an antigen specific response. Generally, the antibodies may be produced by injecting an antigen into an animal (e.g., a mouse, chicken, rabbit, or goat) and allowing the animal to have an immune response to the antigen. Once an animal has begun producing antibodies to the antigen, the antibodies may be removed from the animal's bodily fluids, typically an animal's blood (the serum or plasma) or from the animal's milk. Techniques for producing an immune response to antigens in animals are well known.

Once removed from the animal, the antibody may be coupled to a polymeric bead. The antibody may then act as a receptor for the antigen that was introduced into the animal. In this way, a variety of chemically specific receptors may be produced and used for the formation of a chemically sensitive particle. Once coupled to a particle, a number of well-known techniques may be used for the determination of the presence of the antigen in a fluid sample. These techniques include radioimmunoassay (RIA), microparticle capture enzyme immunoassay (MEIA), fluorescence polarization immunoassay (FPIA), and enzyme immunoassays such as enzyme-linked immunosorbent assay (ELISA). Immunoassay tests, as used herein, are tests that involve the coupling of an antibody to a polymeric bead for the detection of an analyte.

ELISA, FPIA and MEIA tests may typically involve the adsorption of an antibody onto a solid support. The antigen may be introduced and allowed to interact with the antibody. After the interaction is completed, a chromogenic signal generating process may be performed which creates an optically detectable signal if the antigen is present. Alternatively, the antigen may be bound to a solid support and a signal is generated if the antibody is present. Immunoassay techniques have been previously described, and are also described in the following U.S. Pat. Nos.: 3,843,696; 3,876,504; 3,709,868; 3,856,469; 4,902,630; 4,567,149 and 5,681,754, all of which are incorporated by reference.

In ELISA testing, an antibody may be adsorbed onto a polymeric bead. The antigen may be introduced to the assay and allowed to interact with an antibody for a period of hours or days. After the interaction is complete, the assay may be treated with a dye or stain, which reacts with the antibody. The excess dye may be removed through washing and transferring of material. The detection limit and range for this assay may be dependent on the technique of the operator.

Microparticle capture enzyme immunoassay (MEIA) may be used for the detection of high molecular mass and low concentration analytes. The MEIA system is based on increased reaction rate brought about with the use of very small particles (e.g., 0.47 μm in diameter) as the solid phase. Efficient separation of bound from unbound material may be captured by microparticles in a glass-fiber matrix. Detection limits using this type of assay are typically 50 ng/mL.

Fluorescence polarization immunoassay (FPIA) may be used for the detection of low molecular mass analytes, such as therapeutic drugs and hormones. In FPIA, the drug molecules from a patient serum and drug tracer molecules, labeled with fluorescein, compete for the limited binding sites of antibody molecules. With low patient drug concentration, the greater number of binding sites may be occupied by the tracer molecules. The reverse situation may apply for high patient drug concentration. The extent of this binding may be measured by fluorescence polarization, governed by the dipolarity and fluorescent capacity.

Cardiovascular risk factors may be predicted through the identification of many different plasma-based factors using immunoassay. In one embodiment, a sensor array may include one or more particles that produce a detectable signal in the presence of a cardiac risk factor. In some embodiments, all of the particles in a sensor array may produce detectable signals in the presence of one or more cardiac risk factors. Particles disposed in a sensor array may use an immunoassay test to determine the presence of cardiovascular risk factors.

As used herein, cardiovascular risk factors include any analytes that can be correlated to an increase or decrease in risk of cardiovascular disease. Many different cardiovascular risk factors are know, including proteins, organic molecules such as cholesterol and carbohydrates, and hormones. Serum lipids (e.g., HDL and LDL) and lipoproteins are the traditional markers associated with cardiovascular disease. Studies, however, have demonstrated that serum lipids and lipoproteins predict less than half of future cardiovascular events and that other factors such as inflammation may contribute to coronary heart disease. Determining if an analyte is a risk factor for coronary heart disease may be achieved through analysis of the interrelationship between epidemiology and serum biomarker concentrations using risk factors. Examples of plasma based cardiovascular risk factors include, but are not limited to, cytokines (e.g., interleukin-6), proteins (e.g., C-reactive protein, lipoproteins, HDL, LDL, lipoprotein-a, VLDL, soluble intercellular adhesion molecule-i, fibrinogens, apolipoprotein A-1, apolipoprotein b), amino acids (e.g., homocysteine), bacteria (e.g., *Helicobacter pylorn, chlamydia pneumoniae*) and/or viruses (e.g., *Herpes virus hominis*, cytomeglovirus).

Inflammation may contribute to the pathogenesis of arteriosclerosis by destabilizing the fibrous cap of artheriosclerotic plaque causing plaque rupture. The destabilization may increase the risk of coronary thrombosis. The inflammatory process may be associated with increased blood levels of cytokines and consequently, acute-phase reactants, such as C-reactive protein (CRP). CRP is a circulating acute phase reactant that reflects active systemic inflammation. Elevated plasma CRP levels may be associated with the extent and severity of arteriosclerosis thus, a higher risk for cardiovascular events. Numerous studies have established CRP as a plasma-based strong risk predictor for cardiovascular disease in men and women. Plasma CRP levels may be associated with the extent and severity of artheriosclerotic vascular disease. In patients with known coronary artery disease, increased levels of CRP may be associated with an increased risk of future coronary events. CRP may be directly related to Interluekin-6 (IL-6) levels. IL-6 is a cytokine that may promote leukocyte adhesion to the vasculature. IL-6 may be a significant component of the inflammatory process.

Soluble Intercellular Adhesion Molecule-1 (ICAM-1) may be another marker of inflammation associated with an increased risk for myocardial infarction. ICAM-1 may mediate adhesion and transmigration of monocytes to the blood vessel wall. Fibrinogen, HDL, homocysteine, triglycerides and CRP levels may be associated with ICAM-1 levels. ICAM-1 may be involved in endothelial cell activation and inflammation processes. ICAM-1 may also serve as a marker of early arteriosclerosis and associated increase in chances for coronary artery disease.

Fibrinogen may mediate proartheriogenic effects by increasing plasma viscosity, platelet aggregability, and by stimulating smooth muscle cell proliferation. In the study "European Concerted action on thrombosis and disabilities Angina Pectoris Study Group", Thompson, et al.; *N. Engl. J. Med.* 1995, pp. 635-611; high concentrations of fibrinogen and CRP were reported to associate with an increased risk for coronary disease. High fibrinogen levels may be elevated, at least in part, because of inflammatory changes that may occur with progressive arteriosclerosis. Once increased, fibrinogen may aggravate underlying vessel wall injury and, by its pro-coagulant actions, predispose to further coronary events. In patients with chronic angina, fibrinogen levels may predict subsequent acute coronary events. People with low fibrinogen levels may have a low risk of coronary events despite increased serum cholesterol levels. Therefore, fibrinogen may be used as a risk factor for artheriosclerotic vascular disease. Fibrinogen levels may be reduced by smoking cessation, exercise, alcohol intake and estrogens. Fibrinogen levels may increase with age, body size, diabetes, LDL-C, leukocyte count and menopause.

Studies have shown that increased levels of blood homocysteine represents an independent risk factor for acute coronary thrombosis, is a predictor of premature coronary disease/atherosclerosis, and is associated with deep vein thrombosis and thromboembolism.

A number of studies have demonstrated elevated levels of the lipoprotein Lp(a) in patients with angiographic evidence of coronary artery stenosis. As the blood Lp(a) level rises above normal, the odds ratio for progression of CAD also rises, such that at greater than or equal to 30 mg/dL, the risk is more than doubled. Other studies have related Lp(a) levels to total cholesterol/HDL-cholesterol (TC/HDL-C) ratios such that when Lp(a) is greater than 50 mg/dL and the plasma TC/HDL-C ratio is greater than 5.8, the relative odds for CAD is 8.0-9.6.

*Chlamydia pneunoniae, Helicobacter pylori* and *Herpesvirus hominis* may be primary etiologic factors or cofactors in the pathogenesis of arteriosclerosis. The pathophysiological mechanisms by which infectious agents may lead to arteriosclerosis may include, but are not limited to, production of proinflammatory mediators, stimulation of smooth muscle proliferation and endothelial dysfunction. Examples of proinflammatory mediators include but are not limited to, cytokines and free radical species. Activation of an infectious organism within a chronic lesion might lead to plaque inflammation, destabilization, and acute syndromes. Infection-induced inflammation may be amplified by outside factors (e.g. cigarette smoke) and so may be the risk for future cardiovascular events.

Diagnostic testing of cardiovascular risk factors in humans may be performed using a sensor array system customized for immunoassay. The sensor array may include a variety of particles that are chemically sensitive to a variety of cardiovascular risk factor analytes. In one embodiment, the particles may be composed of polymeric beads. Attached to the polymeric beads may be at least one receptor. The receptors may be chosen based on its binding ability with the analyte of interest. (See FIG. 13)

The sensor array may be adapted for use with blood. Other body fluids such as, saliva, sweat, mucus, semen, urine and milk may also be analyzed using a sensor array. The analysis of most bodily fluids, typically, will require filtration of the material prior to analysis. For example, cellular material and proteins may need to be removed from the bodily fluids. As previously described, the incorporation of filters onto the sensor array platform, may allow the use of a sensor array with blood samples. These filters may also work in a similar manner with other bodily fluids, especially urine. Alternatively, a filter may be attached to a sample input port of the sensor array system, allowing the filtration to take place as the sample is introduced into the sensor array.

In an embodiment, cardiovascular risk factors may all be analyzed at substantially the same time using a sensor array system. The sensor array may include all the necessary reagents and indicators required for the visualization of each of these tests. In addition, the sensor array may be formed such that these reagents are compartmentalized. For example, the reagents required for an antigen test may be isolated from those for an antibody test. The sensor array may offer a complete cardiovascular risk profile with a single test.

In an embodiment of a sensor array, particles may be selectively arranged in micromachined cavities localized on silicon wafers. The cavities may be created with an anisotropic etching process as described in U.S. application Ser. No. 10/072,800, which is fully incorporated herein by reference as if set forth herein. The cavities may be pyramidal pit shaped with openings that allows for fluid flow through the cavity and analysis chamber and optical access. Identification and quantitation of the analytes may occur using a calorimetric and/or fluorescent change to a receptor and indicator molecules that are covalently attached to termination sites on the polymeric microspheres. Spectral data is extracted from the array efficiently using a charge-coupled device.

In an embodiment of a multiple receptor particle sensor array, different antibody receptors may be coupled to different particles (see FIGS. 13 and 14). The receptor bound particles may be placed in a sensor array as described herein. A stream derived from a bodily fluid isolated from a person may be passed over the array. The receptor specific analyte may interact with the different receptors. An enzyme linked protein visualization agent is added to the fluid phase. Chemical derivatization of the visualization agent with a dye is performed. After binding to the bead-localized antibodies, the visualization agent reveals the presence of complimentary antibodies at specific polymer bead sites. Level of detection of the antibodies concentration may be between about 1 and 10,000 ng/mL. In an embodiment, the level of detection of the CRP antibodies concentration may be less than about 1 ng/mL.

In an embodiment, a mixture of visualization processes may be used. For example, the visualization process may include a protein conjugated with a fluorescent dye. A second visualization process may include a protein conjugated with colloidal gold. The beads that are complexed with particle-analyte-fluorescent dye signal generator may be visualized through illumination at the excitation wavelength maximum of the fluorophore (e.g., 470 nm). Particleanalyte-colloidal gold conjugated protein may be visualized through exposure to a silver enhancer solution.

In an embodiment, a protein and a bacterium known to predict cardiovascular risk may be detected. For example, in a multiple receptor particle sensor array, antibody receptors (e.g., CRP antibody, *chlamydia pneumoniae* antibody) may be coupled to different particles. The receptor bound particles may be placed in a sensor array. A stream containing multiple analytes may be passed over the array. The receptor specific analyte may interact with the CRP and/or *chlamydia pneumonia* bound antibodies. After the interaction is complete, a visualization agent may be added to the sensor array. An optically detectable signal may be detected, if the protein and/or bacterium is present. In an embodiment, the protein and bacterium receptors may be coupled to the same particle.

IL-6 regulates the production of CRP in acute phase inflammatory response. Analysis of IL-6 and CRP in the blood serum may give a better prediction of cardiovascular disease. In an embodiment, the analysis of IL-6 and CRP in blood serum may be accomplished using a sensor array by incorporating particles that interact with CRP and IL-6. The intensity of the signal produced by the interaction of the particles with the analytes may be used to determine the concentration of the CRP and IL-6 in the blood serum. In some embodiments, multiple particles may be used to detect, for example CRP. Each of the particles may produce a signal when a specific amount of CRP is present. If the CPR present is below a predetermined concentration, the particle may not produce a detectable signal. By visually noting which of the particles are producing signals and which are not, a semi-quantitative measure of the concentration of CRP may be determined.

In an embodiment, the particles in the sensor array may be regenerated. A stream containing solutions (e.g., glycine-HCL buffer and/or $MgCl_2$,) efficient in releasing particleAttorney analyte-visualization reagent complex may be passed over the sensor array. Repetitive washings of the particles in the array may be performed until an acceptable background signal using CCD methodology may be produced, in an embodiment. The sensor array may then be treated with a stream of analyte solution, visualization receptor stream, then visualized using a reactant stream and/or fluorescence. Multiple cycles of testing and regeneration may be performed with the same sensor array.

EXAMPLES

Coupling of Antibodies to Particles Using a Sensor Array System

In an embodiment, different particles were manufactured by coupling a different antibody to an agarose bead particle. The agarose bead particles were obtained from XC Corporation, Lowell MA. The particles had an average diameter of about 280 μm. The receptor ligands of the antibodies were attached to agarose bead particles using a reductive amination process between a terminal resin bound gloyoxal and an antibody to form a reversible Schiff Base complex which can be selectively reduced and stabilized as covalent linkages by using a reducing agent such as sodium cyanoborohydride. (See Borch et al. *J. Am. Chem. Soc.* 1971, 93, 2897-2904, which is incorporated fully herein.).

Detection Methods Using a Sensor Array System

Spectrophotometric assays to probe for the presence of the particle-analyte-visualization reagent complex were performed calorimetrically using a CCD device, as previously described. For identification and quantification of the analyte species, changes in the light absorption and light emission properties of the immobilized particle-analyte-visualization reagent complex were exploited. Identification based upon absorption properties are described herein. Upon exposure to the chromogenic signal generating process, color changes for the particles were about 90% complete within about one hour of exposure. Data streams composed of red, green, and blue (RGB) light intensities were acquired and processed for each of the individual particle elements.

Figure 39:
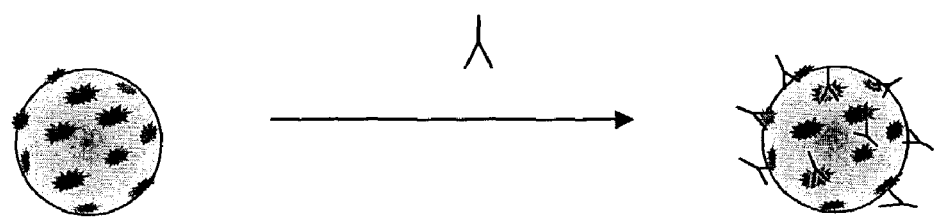
FIGS. 39A-B depict the detection of Hepatitis B HbsAg in the presence of HIV gp41/120 and Influenza A in an embodiment of a sensor array system.
Figure 39:
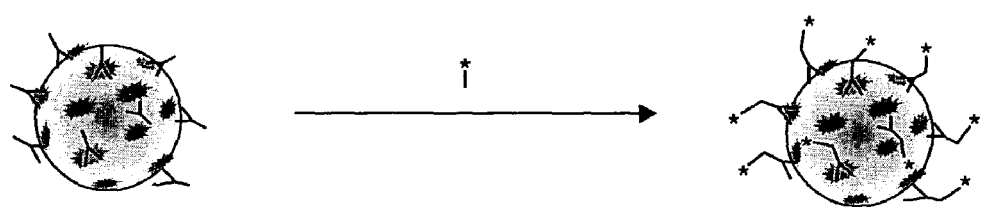

Detection of Hepatitis B HBsAg In the Presence of HIV gp41/120, Influenza A Using A Sensor Array System In an embodiment, three different particles were manufactured by coupling a HIV gp41/120, Influenza A and Hepatitis B (HBsAg) antigens to a bead particle (FIG. 39A). A series of HIV gp41/120 particles were placed within micromachined wells in a column of a sensor array. Similarly, Influenza A and Hepatitis B HBsAg particles are placed within micromachined wells of the sensor array. Introduction of a fluid containing HBsAg specific IgG was accomplished through the top of the sensor array with passage through the openings at the bottom of each cavity. Unbound HBsAg-IgG was washed away using a pH 7.6 TRIS buffer solution. The particle-analyte complex was then exposed to a fluorophore visualization reagent (e.g., CY2, FIG. 39B). A wash fluid was passed over the sensor array to remove the unreacted visualization agent. Spectrophotometric assays to probe for the presence of the particle-analytevisualization reagent complex was performed calorimetrically using a CCD device. Particles that have form complexes with HBsAg specific IgG exhibit a higher fluorescent value than the noncomplexed Influenza A and HIV gp41/120 particles.

Detection of CRP Using a Sensor Array System

In an embodiment, a series of 10 particles were manufactured by coupling a CRP antibody to the particles at a high concentration (6 mg/mL). A second series of 10 particles were manufactured by coupling the CRP antibody to the particles at medium concentration (3 mg/mL). A third series of 10 particles were manufactured by coupling the CRP antibody to particles at a low concentration (0.5 mg/mL). A fourth series of 5 particles were manufactured by coupling an immunoglobulin to the particles. The fourth series of particles were a control for the assay. The particles were positioned in columns within micromachined wells formed in silicon/silicon nitride wafers, thus confining the particles to individually addressable positions on a multi-component chip.

Figure 40:
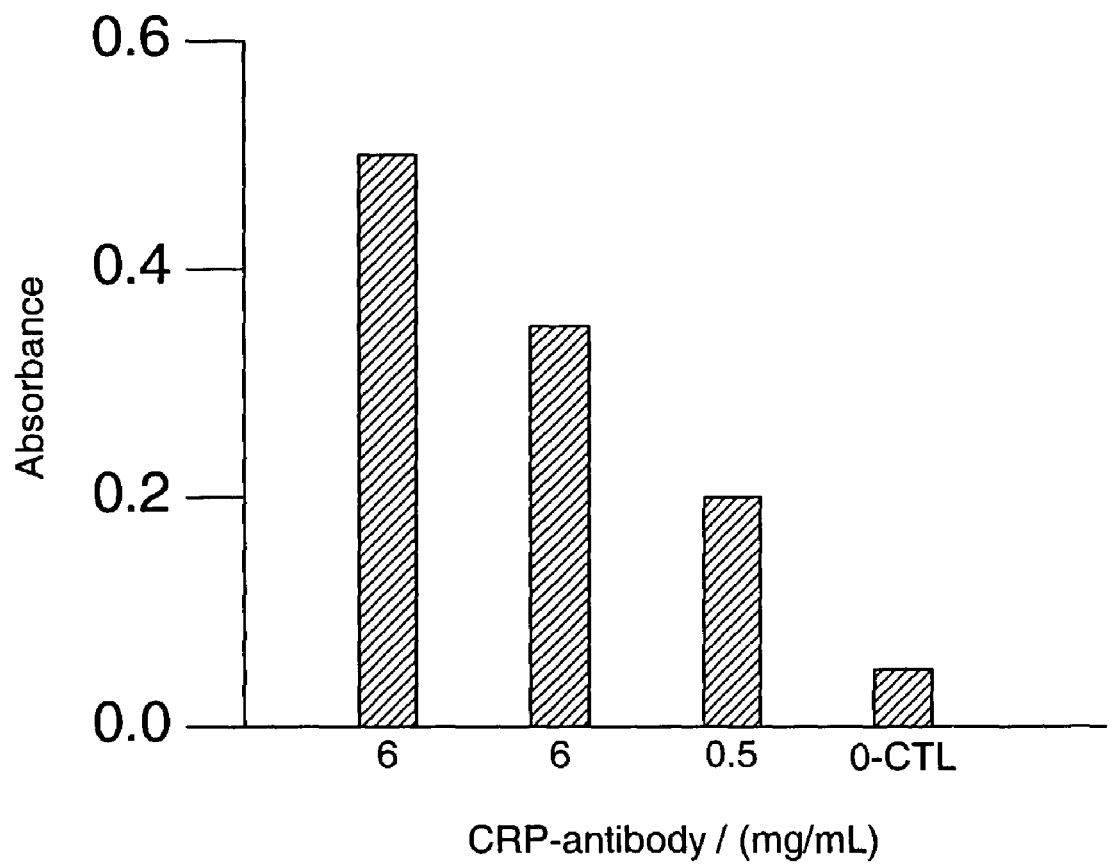
FIG. 40 depict the detection of CRP in an embodiment of a sensor array system.

The sensor array was blocked with 3% bovine serum albumin in phosphate buffered solution (PBS) was passed through the sensor array system. Introduction of the analyte fluid (1,000 ng/mL of CRP) was accomplished through the top of the sensor array with passage through the openings at the bottom of each cavity. The particle-analyte complex was then exposed to a visualization reagent (e.g., horseradish peroxidase-linked antibodies). A dye (e.g., 3-amino-9-ethylcarbazole) was added to the sensor array. Spectrophotometric assays to probe for the presence of the particle-analyte-visualization reagent complex was performed calorimetrically using a CCD device. The average blue responses of the particles to CRP are depicted in FIG. 40. The particles with the highest concentration of CRP-specific antibody (6 mg/mL) exhibited a darker blue color. The control particles (0 mg/mL) exhibited little color.

Dosage Response for CRP Using a Sensor Array System

In an embodiment, a series of 10 particles were manufactured by coupling a CRP antibody to the particles at a high concentration (6 mg/mL). A second series of 10 particles were manufactured by coupling the CRP antibody to the particles at a medium concentration (3 mg/mL). A third series of 10 particles were manufactured by coupling the CRP antibody to the particles at a low concentration (0.5 mg/mL). A fourth series of 5 particles were manufactured by coupling an immunoglobulin to the particles. The fourth series of particles were a control for the assay. The particles were positioned in columns within micromachined wells formed in silicon/silicon nitride wafers, thus confining the particles to individually addressable positions on a multi-component chip.

Figure 41:
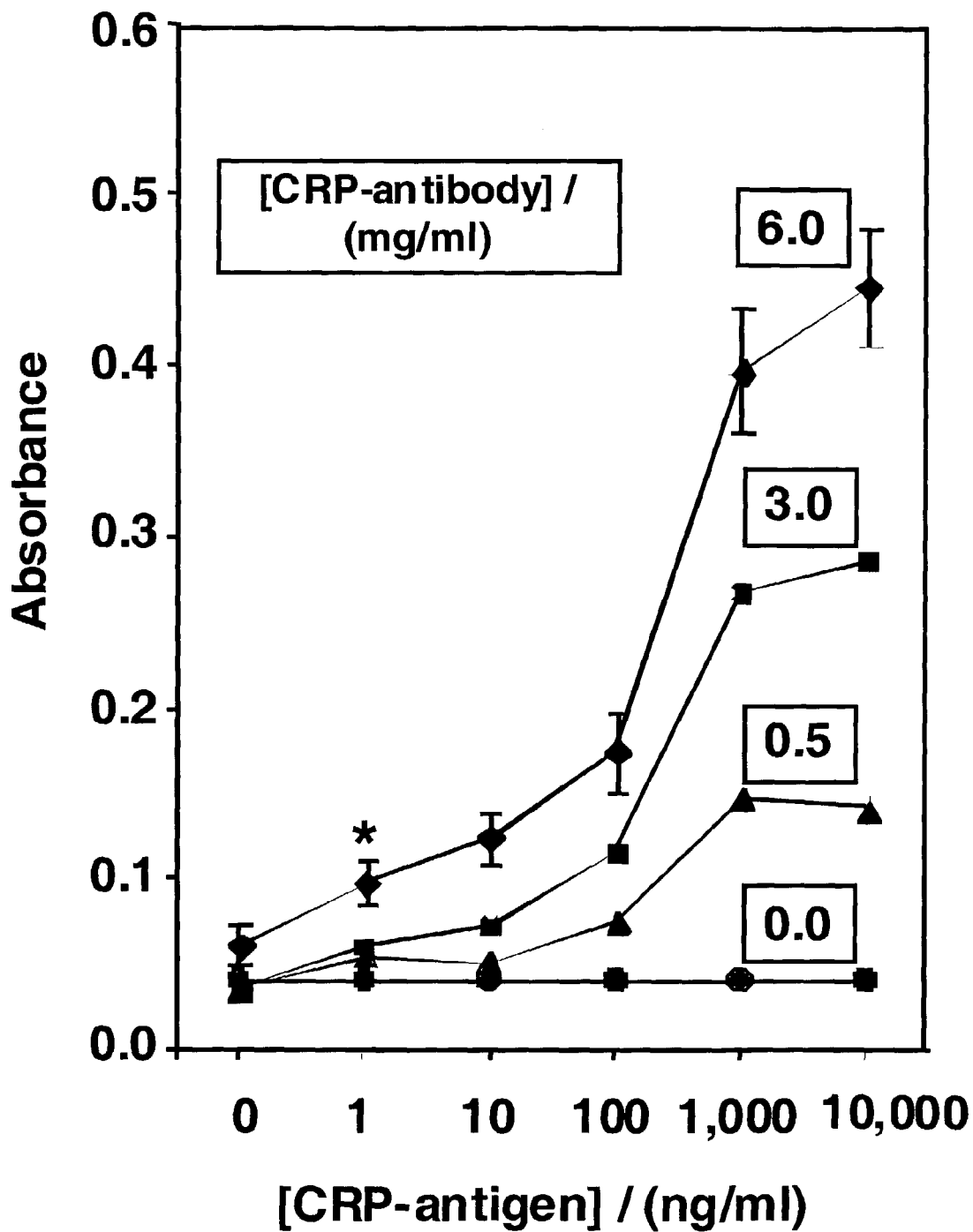
FIG. 41 depicts the dosage response of CRP levels in an embodiment of a sensor array system.

The sensor array was blocked with 3% bovine serum albumin in phosphate buffered solution (PBS) was passed through the sensor array system. Introduction of multiple streams of analyte fluids at varying concentrations (0 to 10,000 ng/mL) were accomplished through the top of the sensor array with passage through the openings at the bottom of each cavity. The particle-analyte complex was then exposed to a visualization reagent (e.g., horseradish peroxidase-linked antibodies). A dye (e.g., 3-amino-9-ethylcarbazole) was added to the sensor array. Spectrophotometric assays to probe for the presence of the particle-analyte-visualization reagent complex was performed calorimetrically using a CCD device. The dose dependent signals are graphically depicted in FIG. 41.

Simultaneous Detection of CRP and IL-6 Using a Sensor Array System

Figure 42A:
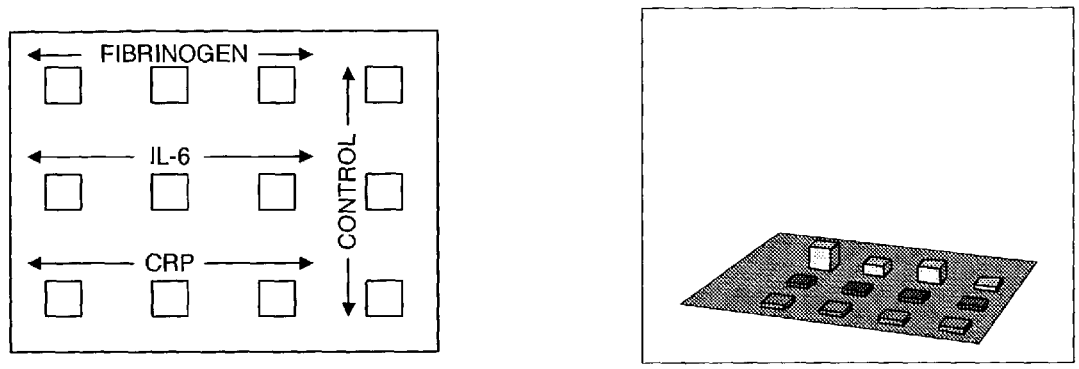
FIGS. 42A-D depict the multi-analyte detection of CRP and IL-6 in an embodiment of a sensor array system.
Figure 42B:
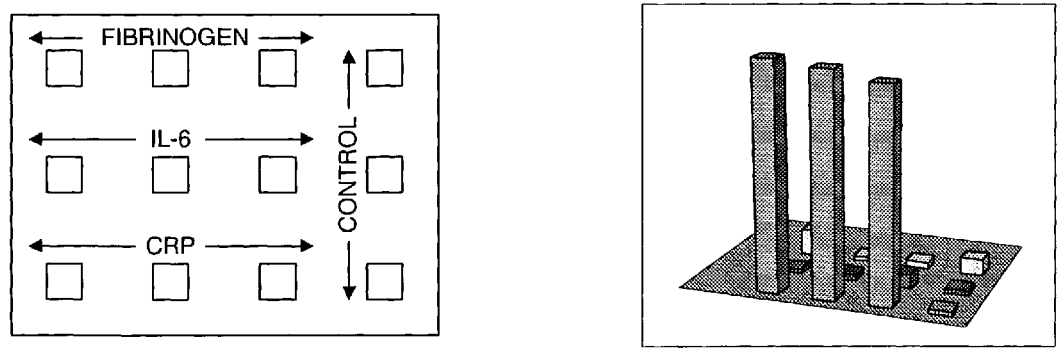
Figure 42C:
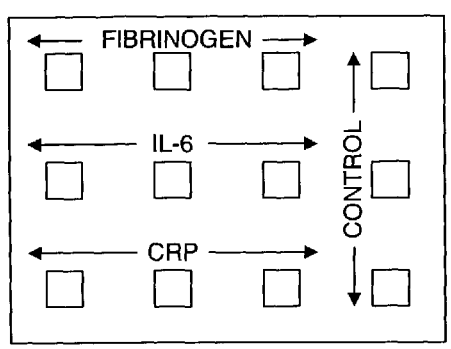
Figure 42C:
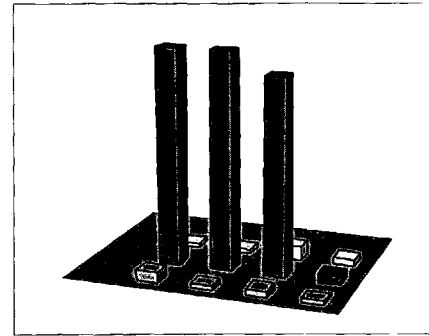
Figure 42D:
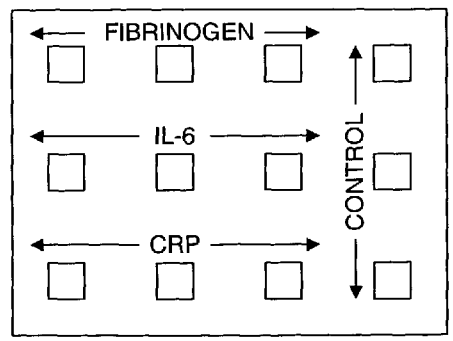
Figure 42D:
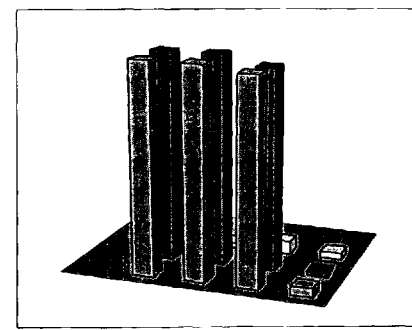

In an embodiment, three different particles were manufactured by coupling Fibrinogen. CRP and IL-6 antibodies to an agarose bead particle. A series of CRP and IL-6 antibodies receptor particles, were positioned within micromachined wells formed in silicon/silicon nitride wafers, thus confining the particles to individually addressable positions on a multi-component chip. A series of control particles were also placed in the sensor array. The sensor array was blocked by passing 3% bovine serum albumin in phosphate buffered solution (PBS) through the sensor array system. Introduction of the analyte fluids was accomplished through the top of the sensor array with passage through the openings at the bottom of each cavity. The particle-analyte complex was then exposed to a visualization reagent (e.g., horseradish peroxidase-linked antibodies). A dye (e.g., 3-amino-9-ethylcarbazole) was added to the sensor array. Spectrophotometric assays to probe for the presence of the particle-analyte-visualization reagent complex was performed calorimetrically using a CCD device. The average blue responses of the particles to a fluid that includes buffer only (FIG. 42A), CRP (FIG. 42B), interluekin-6 (FIG. 42C) and a combination of CRP and interleukin-6 (FIG. 42D) are graphically depicted in FIG. 42.

This example demonstrated a number of important factors related to the design, testing, and functionality of micromachined array sensors for cardiac risk factor analyses. First, derivatization of agarose particles with both antibodies was completed. These structures were shown to be responsive to plasma and a visualization process. Second, response times well under one hour was found for calorimetric analysis. Third, micromachined arrays suitable both for confinement of particles, as well as optical characterization of the particles, have been prepared. Fourth, each bead is a full assay, which allows for simultaneous execution of multiple trials. More trials provide results that are more accurate. Finally, simultaneous detection of several analytes in a mixture was made possible by analysis of the blue color patterns created by the sensor array.

In an embodiment, 35 particles were manufactured by coupling a CRP antibody to the particles. The particles were positioned in columns within micromachined wells formed in silicon/silicon nitride wafers, thus confining the particles to individually addressable positions on a multi-component chip.

Regeneration of Sensor Array for Performing Multiple Tests

Figure 38:
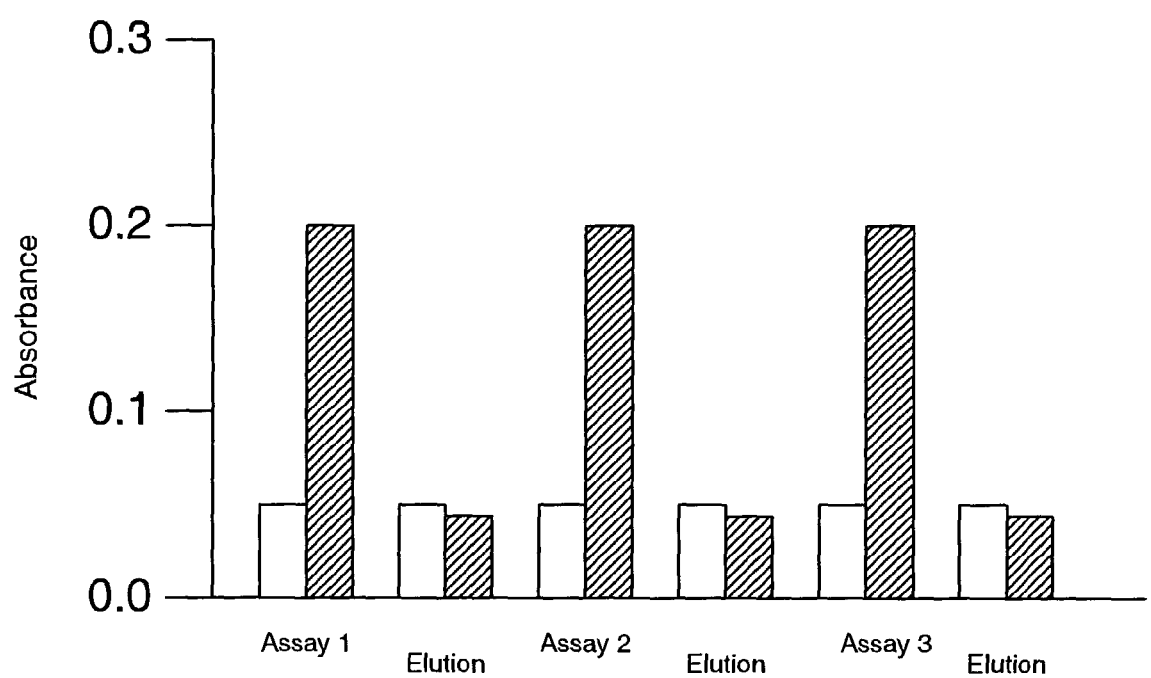
FIG. 38 depicts the regeneration of receptor particles in an embodiment of a sensor array system.

Beads coupled to 3 mg of antibody/ml of beads of either rabbit CRP-specific capture antibody (CRP) or an irrelevant rabbit anti-*H. pylori*-specific antibody (CTL) are tested for their capacity to detect 1,000 ng/ml of CRP in human serum in continuous repetitive runs. FIG. 38 depicts data collected using a colorimetric method. Here each cycle involves: i) injection of 1,000 ng/ml CRP, ii) addition of HRP-conjugated anti-CRP detecting antibody, iii) addition of AEC, iv) elution of signal with 80% methanol, v) wash with PBS, vi) regeneration with glycine-HCl buffer and vii) equilibration with PBS. Results shown in FIG. 38 are for the mean blue absorbance values. The results show that regeneration of the system can be achieved over to allow multiple testing cycles to be performed with a single sensor array.

Other Cardiovascular Risk Factors

Several home testing kits have been developed for cardiac risk factors that rely on the use of an enzyme based testing. These types of tests are well suited to be incorporated as sensor array diagnotistic testing system.

Cholesterol, a common constituent of blood, is cardiac risk factor that is frequently monitored by people. A number of home testing kits have been developed that rely on the use of an enzyme based testing method for the determination of the amount of cholesterol in blood. A method for the determination of cholesterol in blood is described in U.S. Pat. No. 4,378,429, which is incorporated by reference. The assay used in this test may be adapted to use in a bead based sensor array system for analysis of cardiac risk factors.

The triglyceride level in blood is also commonly tested for because it is an indicator of obesity, diabetes, and heart disease. A system for assaying for triglycerides in bodily fluids is described in U.S. Pat. No. 4,245,041, which is incorporated by reference. The assay used in this test may be adapted to use in a bead based sensor array system for analysis of cardiac risk factors.

The concentration of homocysteine may be an important indicator of cardiovascular disease and various other diseases and disorders. Various tests have been constructed to measure the concentration of homocysteine in bodily fluids. A method for the determination of homocysteine in blood, plasma, and urine is described in U.S. Pat. Nos. 6,063,581 and 5,478,729 entitled "Immunoassay for Homocysteine", which is incorporated by reference. The assay used in this test may be adapted to use in a bead based sensor array system for analysis of cardiac risk factors.

Cholesterol, triglyceride, homocysteine, and glucose testing may be performed simultaneously using a sensor array system. Particles that are sensitive to cholesterol, triglyceride, homocysteine, or glucose may be placed in the sensor array. Blood serum passed over the array may be analyzed for glucose, triglyceride, and cholesterol. A key feature of a glucose, triglyceride, homocysteine, and/or cholesterol test is that the test should be able to reveal the concentration of these compounds in a person's blood. This may be accomplished using the sensor array by calibrating the reaction of the particles to cholesterol, triglyceride, or glucose. The intensity of the signal may be directly correlated to the concentration. In another embodiment, multiple particles may be used to detect, for example, glucose. Each of the particles may produce a signal when a specific amount of glucose is present. If the glucose present is below a predetermined concentration, the particle may not produce a detectable signal. By visually noting which of the particles are producing signals and which are not, a semiquantitative measure of the concentration of glucose may be determined. A similar methodology may be used for cholesterol, triglyceride, homocysteine, or any combination thereof (e.g., glucose/cholesterol/triglyceride/homocysteine, cholesterol/triglyceride, glucose/triglyceride, glucose/cholesterol, etc.).

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.eb;normal

What is claimed is

1. A system for detecting cardiovascular risk factor analytes in a fluid, comprising:
   a light source;
   a sensor array, the sensor array comprising a supporting member comprising a plurality of cavities formed within the supporting member;
   a plurality of particles, wherein an individual particle is positioned within an individual cavity and is configured to produce a signal in the presence of a cardiovascular risk factor, wherein the cardiovascular risk factor comprises C-reactive protein, high density lipoprotein, low density lipoprotein, very low density lipoprotein, cholesterol, interleukin-6, intercellular adhesion molecule-1, fibrinogen, homocysteine, folate, calcium, lipoprotein a, apolipoprotein A-1, apolipoprotein B, *Helicobacter pylori, chlamydia pneumoniae, Herpes virus hominis*, and cytomegalovirus; and
   a detector, wherein the detector is configured to detect the signal produced by the particles during use.

2. The system of claim 1, wherein the light source comprises a light emitting diode.

3. The system of claim 1, wherein the light source comprises a white light source.

4. The system of claim 1, wherein the light source comprises a red light emitting diode, a blue light emitting diode, and a green light emitting diode.

5. The system of claim 1, wherein the sensor array further comprises a bottom layer and a cover, wherein the bottom layer is coupled to a bottom surface of the supporting member, and wherein the cover is coupled to a top surface of the supporting member; and wherein both the bottom layer and the cover are coupled to the supporting member such that at least one of the particles is substantially contained within at least one of the cavities by the bottom layer and the cover, and wherein the bottom layer and the cover are substantially transparent to light produced by the light source.

6. The system of claim 1, wherein the sensor array further comprises a bottom layer coupled to the supporting member, and wherein the supporting member comprises silicon, and wherein the bottom layer comprises silicon nitride.

7. The system of claim 1, wherein the sensor array further comprises a cover, the cover being coupled to the supporting member such that at least one of the particles is substantially contained within at least one of the cavities by the cover, and wherein the cover is configured to allow the fluid to pass through the cover to at least one of the particles, and wherein both the supporting member and the cover are substantially transparent to light produced by the light source.

8. The system of claim 1, wherein the sensor array further comprises a cover positioned at a distance above the upper surface of the supporting member such that an opening is formed between the supporting member and the cover to allow the fluid to enter at least one of the cavities via the opening, and wherein the cover inhibits dislodgment of at least one of the particles from at least one of the cavities during use.

9. The system of claim 1, wherein at least one of the cavities is configured such that the fluid entering the cavity passes through the supporting member during use.

10. The system of claim 1, wherein at least one of the cavities is substantially tapered such that the width of the tapered cavity narrows in a direction from a top surface of the supporting member toward a bottom surface of the supporting member, and wherein a minimum width of the tapered cavity is substantially less than a width of at least one of the particles.

11. The system of claim 1, wherein an inner surface of one or more of the cavities is coated with a reflective material.

12. The system of claim 1, wherein the detector comprises a charge-coupled device.

13. The system of claim 1, wherein at least one of the particles comprises a receptor molecule coupled to a polymeric resin.

14. The system of claim 1, wherein at least one of the particles comprises a receptor molecule coupled to a polymeric resin, and wherein the polymeric resin comprises polystyrene-polyethylene glycol-divinyl benzene.

15. The system of claim 1, wherein at least one of the particles comprises a receptor molecule coupled to a polymeric resin, and wherein at least one of the particles further comprises a first indicator and a second indicator, the first and second indicators being coupled to the receptor molecule, wherein the interaction of the receptor molecule with at least one of the cardiac risk factor analytes causes the first and second indicators to interact such that the signal is produced.

16. The system of claim 1, wherein at least one of the particles comprises a receptor molecule coupled to a polymeric resin, and wherein at least one of the particles further comprises an indicator, wherein the indicator is associated with the receptor molecule such that in the presence of at least one of the cardiac risk factor analytes the indicator is displaced from the receptor molecule to produce the signal.

17. The system of claim 1, wherein at least one of the particles comprises a receptor molecule coupled to a polymeric resin, and wherein the receptor molecule comprises a peptide.

18. The system of claim 1, wherein at least one of the particles comprises a receptor molecule coupled to a polymeric resin, and wherein the receptor molecule comprises an enzyme.

19. The system of claim 1, wherein at least one of the particles comprises a receptor molecule coupled to a polymeric resin, and wherein the receptor molecule comprises a synthetic receptor.

20. The system of claim 1, wherein at least one of the particles comprises a receptor molecule coupled to a polymeric resin, and wherein the receptor molecule comprises an antibody.

21. The system of claim 1, wherein at least one of the particles comprises a receptor molecule coupled to a polymeric resin, and wherein the receptor molecule comprises an antigen.

22. The system of claim 1, wherein the supporting member comprises silicon.

23. The system of claim 1, wherein the supporting member comprises a plastic material.

24. The system of claim 1, wherein the supporting member comprises a dry film photoresist material.

25. The system of claim 1, wherein the supporting member comprises a plurality of layers of a dry film photoresist material.

26. The system of claim 1, further comprising a fluid delivery system coupled to the supporting member.

27. The system of claim 1, wherein the sensor array further comprises a pump coupled to the supporting member, wherein the pump is configured to direct the fluid towards at least one of the cavities, and wherein a channel is formed in the supporting member, the channel coupling the pump to the cavity such that the fluid flows through the channel to at least one of the cavities during use.

28. The system of claim 1, further comprising a conduit coupled to the sensor array, wherein the conduit is configured to conduct the fluid sample to and away from the sensor array; and a vacuum chamber coupled to the conduit, wherein the vacuum chamber is configured to pull the fluid through the conduit when the vacuum chamber is activated.

29. The system of claim 1, further comprising a conduit coupled to the sensor array, wherein the conduit is configured to conduct the fluid sample to and away from the sensor array; and a filter coupled to the conduit and the sensor array, wherein the fluid passes through the filter before reaching the sensor array.

30. A system for detecting cardiovascular risk factor analytes in a fluid comprising:
- a light source;
- a sensor array, the sensor array comprising a supporting member comprising a plurality of cavities formed within the supporting member;
- a plurality of particles, wherein an individual particle is positioned within an individual cavity, wherein a particle is configured to produce a signal when the particle interacts with a cardiovascular risk factor analyte during use, the cardiovascular risk factor comprising C-reactive protein, interleukin-6, and one or more of high density lipoprotein, low density lipoprotein, very low density lipoprotein, cholesterol, intercellular adhesion molecule-1, fibrinogen, homocysteine, folate, calcium, lipoprotein a, apolipoprotein A -1, apolipoprotein B, *Helicobacter pylori, chlamydia pneumoniae, Herpes virus hominis*, and cytomegalovirus; and
- a detector, wherein the detector is configured to detect the signals produced by the interaction of the particles with the cardiovascular risk factor analytes during use;
- wherein the system is configured to simultaneously determine the presence of the cardiovascular risk factors.

* * * * *